US012098429B2

United States Patent
Lo et al.

(10) Patent No.: US 12,098,429 B2
(45) Date of Patent: Sep. 24, 2024

(54) DETERMINING LINEAR AND CIRCULAR FORMS OF CIRCULATING NUCLEIC ACIDS

(71) Applicants: The Chinese University of Hong Kong, Shatin (HK); GRAIL, Inc., Menlo Park, CA (US)

(72) Inventors: Yuk-Ming Dennis Lo, Kowloon (CN); Rossa Wai Kwun Chiu, Shatin (CN); Kwan Chee Chan, Kowloon (CN); Peiyong Jiang, Shatin (CN); Lu Ji, Shatin (HK); Tsz Kwan Sin, Kowloon (CN); Haiqiang Zhang, Shatin (HK); Jiaen Deng, Shatin (HK)

(73) Assignees: The Chinese University of Hong Kong, Shatin (HK); GRAIL, Inc., Menlo Park, CA (US)

( * ) Notice: Subject to any disclaimer, the term of this patent is extended or adjusted under 35 U.S.C. 154(b) by 991 days.

(21) Appl. No.: 16/829,771

(22) Filed: Mar. 25, 2020

(65) Prior Publication Data

US 2020/0407799 A1  Dec. 31, 2020

Related U.S. Application Data

(60) Provisional application No. 62/823,567, filed on Mar. 25, 2019.

(51) Int. Cl.
*C12Q 1/6886* (2018.01)
*G16B 20/10* (2019.01)
(Continued)

(52) U.S. Cl.
CPC ...... *C12Q 1/6886* (2013.01); *C12Q 2531/113* (2013.01); *C12Q 2600/118* (2013.01);
(Continued)

(58) Field of Classification Search
CPC ............ C12Q 1/6886; C12Q 2600/118; G16B 20/10; G16B 20/20; G16B 30/10
See application file for complete search history.

(56) References Cited

U.S. PATENT DOCUMENTS 8,741,811 B2  6/2014  Lo et al.
9,892,230 B2  2/2018  Lo et al.
(Continued)

FOREIGN PATENT DOCUMENTS

CN  102421792 A  4/2012
CN  104342453 A  2/2015
(Continued)

OTHER PUBLICATIONS

Zhu, J., Zhang, F., Du, M. et al. Molecular characterization of cell-free eccDNAs in human plasma. Sci Rep 7, 10968 (2017). https://doi.org/10.1038/s41598-017-11368-w (Year: 2017).*
(Continued)

*Primary Examiner* — Lori A. Clow
*Assistant Examiner* — Emilie A Neulen
(74) *Attorney, Agent, or Firm* — Kilpatrick Townsend & Stockton LLP

(57) ABSTRACT

Techniques are provided for analyzing circular DNA in a biological sample (e.g., including cell-free DNA, such as plasma). For example, to measure circular DNA, cleaving can be performed to linearize the circular DNA so that they may be sequenced. Example cleaving techniques include restriction enzymes and transposases. Then, one or more criteria can be used to identify linearized DNA molecules, e.g., so as to differentiate from linear DNA molecules. An example criterion is mapping a pair of reversed end sequences to a reference genome. Another example criterion is identification of a cutting tag, e.g., associated with a restriction enzyme or an adapter sequence added by a
(Continued)

transposase. Once circular DNA molecules (e.g., eccDNA and circular mitochondrial DNA) are identified, they may be analyzed (e.g., to determine a count, size profile, and/or methylation) to measure a property of the biological sample, including genetic properties and level of a disease.

25 Claims, 41 Drawing Sheets
(27 of 41 Drawing Sheet(s) Filed in Color)

(51) Int. Cl.
    *G16B 20/20*     (2019.01)
    *G16B 30/10*     (2019.01)

(52) U.S. Cl.
    CPC ...... *C12Y 301/21004* (2013.01); *G16B 20/10* (2019.02); *G16B 20/20* (2019.02); *G16B 30/10* (2019.02)

(56) References Cited

U.S. PATENT DOCUMENTS

| | | | |
|---|---|---|---|
| 10,319,463 B2 | 6/2019 | Lo et al. | |
| 10,364,467 B2 | 7/2019 | Lo et al. | |
| 2016/0203260 A1 | 7/2016 | Lo et al. | |
| 2020/0199656 A1 | 6/2020 | Lo et al. | |

FOREIGN PATENT DOCUMENTS

| | | |
|---|---|---|
| CN | 105525357 A | 4/2016 |
| WO | 9739149 A1 | 10/1997 |
| WO | 2006119066 A2 | 11/2006 |
| WO | 2014043763 | 3/2014 |
| WO | 2020210802 A1 | 10/2020 |

OTHER PUBLICATIONS

Pankaj Kumar, Laura W. Dillon, Yoshiyuki Shibata, Amir A. Jazaeri, David R. Jones, Anindya Dutta; Normal and Cancerous Tissues Release Extrachromosomal Circular DNA (eccDNA) into the Circulation. Mol Cancer Res Sep. 1, 2017; 15 (9): 1197-1205. https://doi.org/10.1158/1541-7786.MCR-17-0095 (Year: 2017).*

Picelli S, Björklund AK, Reinius B, Sagasser S, Winberg G, Sandberg R. Tn5 transposase and tagmentation procedures for massively scaled sequencing projects. Genome Res. Dec. 2014;24(12):2033-40. doi: 10.1101/gr.177881.114. Epub Jul. 30, 2014. PMID: 25079858; PMCID: PMC4248319. (Year: 2014).*

Stanislav Volik, Miguel Alcaide, Ryan D. Morin, Colin Collins; Cell-free DNA (cfDNA): Clinical Significance and Utility in Cancer Shaped By Emerging Technologies. Mol Cancer Res Oct. 1, 2016; 14 (10): 898-908. https://doi.org/10.1158/1541-7786.MCR-16-0044 (Year: 2016).*

Cohen, S., Houben, A. and Segal, D. (2008), Extrachromosomal circular DNA derived from tandemly repeated genomic sequences in plants. The Plant Journal, 53: 1027-1034. https://doi.org/10.1111/j.1365-313X.2007.03394.x (Year: 2008).*

Alisch, R.S., Wang, T., Chopra, P. et al. Genome-wide analysis validates aberrant methylation in fragile X syndrome is specific to the FMR1locus. BMC Med Genet 14, 18 (2013). https://doi.org/10.1186/1471-2350-14-18 (Year: 2013).*

Chu JS, Johnsen RC, Chua SY, Tu D, Dennison M, Marra M, Jones SJ, Baillie DL, Rose AM. Allelic ratios and the mutational landscape reveal biologically significant heterozygous SNVs. Genetics. Apr. 2012; 190(4):1225-33. doi: 10.1534/genetics.111.137208. Epub Jan. 20, 2012. (Year: 2012).*

Iwasaki, Toshiyasu, Ohki, Rieko, Kiyama, Ryoiti and Oishi, Michio(1995), Analysis of recombination junctions in extrachromosomal circular DNA obtained by in-gel competitive reassociation, FEBS Letters, 363, 239-245, doi: 10.1016/0014-5793(95)00325-4 (Year: 1995).*

Newell et al., Plasma-Derived Cell-free Mitochondrial DNA: A Novel Non-invasive Methodology to Identify Mitochondrial DNA Haplogroups in Humans, Molecular Genetics and Metabolism, vol. 125, No. 4, Dec. 2018, pp. 332-337.

International Application No. PCT/CN2020/081066, International Preliminary Report on Patentability mailed on Oct. 7, 2021, 6 pages.

Shoura et al., Intricate and Cell Type-Specific Populations of Endogenous Circular DNA (eccDNA) in Caenorhabditis Elegans and *Homo sapiens*, G3: Genes, Genomes, Genetics (Bethesda), vol. 7, No. 10, Oct. 5, 2017, pp. 3295-3303.

Verhaak et al., Extrachromosomal Oncogene Amplification in Tumour Pathogenesis and Evolution, Nature Reviews Cancer, vol. 19, No. 5, May 2019, pp. 283-288.

International Search Report and Written Opinion mailed Jun. 23, 2020 in International Patent Application No. PCT/CN2020/081066. 9 pages.

Zhu, Jing et al.; "Molecular characterization of cell-free eccDNAs in human plasma"; Scientific Reports; Sep. 8, 2017; vol. 7; Article No. 10968 (2017); 11 pages.

Zhu, Jing et al.; "Cell-free eccDNAs: a new type of nucleic acid component for liquid biopsy?"; Molecular Diagnosis & Therapy; HHS Public Access Author Manuscript; Oct. 2018; vol. 22, No. 5; pp. 515-522 (manuscript: 13 pages).

Extended European Search Report dated Nov. 29, 2022 in EP Patent Application No. 20776651.0. 11 pages.

Moeller, Henrik Devitt et al.; "Circular DNA elements of chromosomal origin are common in healthy human somatic tissue"; Nature Communications; 2018; vol. 9, No. 1069; 12 pages.

Brennan, Cameron W. et al.; "The Somatic Genomic Landscape of Glioblastoma"; Cell; Oct. 10, 2013; vol. 155, Issue 2; pp. 462-477 (18 total pages).

English translation of Search Report mailed Mar. 19, 2024 in TW Patent Application No. 109110102. 1 page.

Office Action dated Mar. 27, 2024 in CA Patent Application No. 3,130,810. 6 pages.

\* cited by examiner

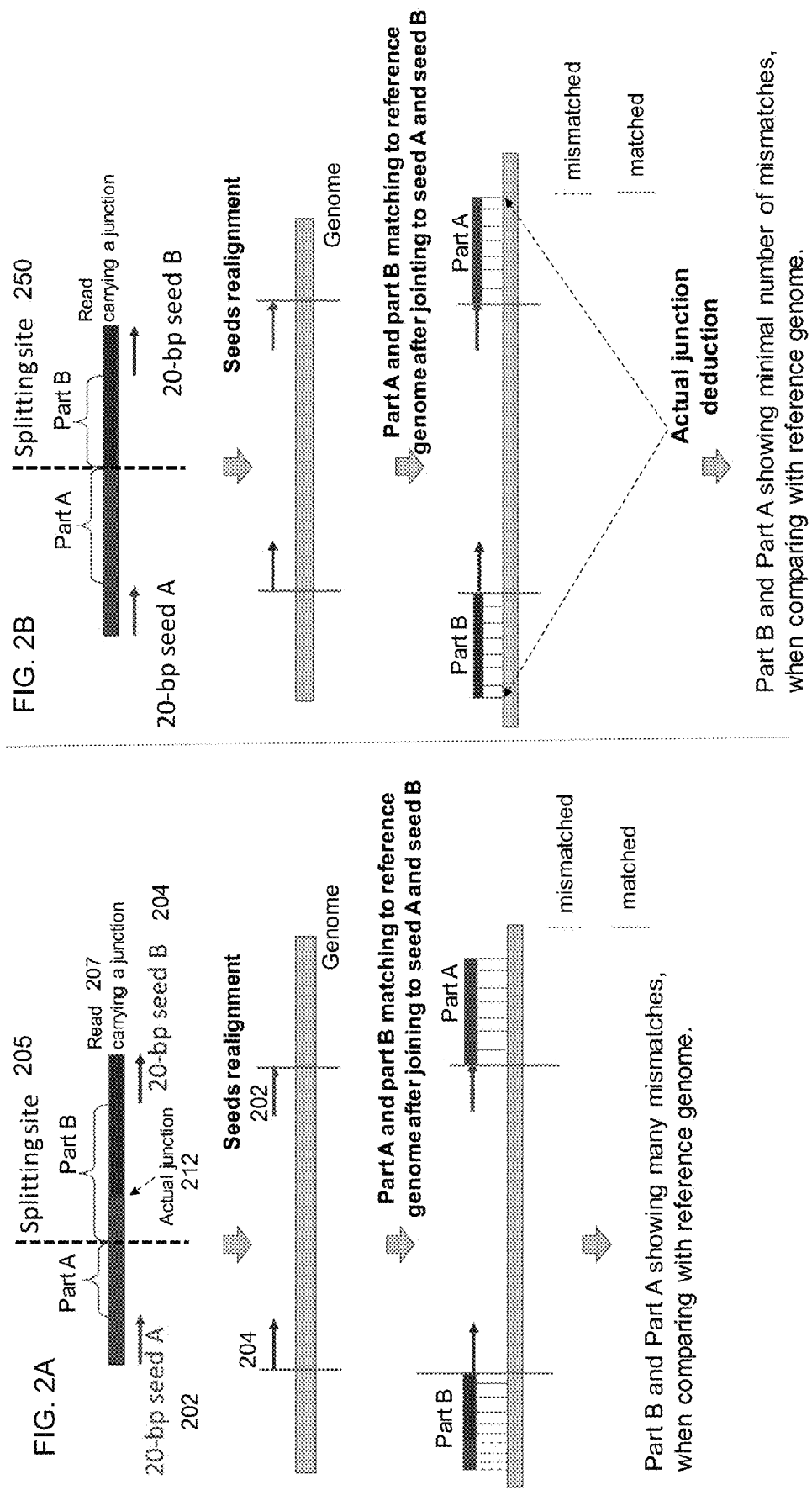

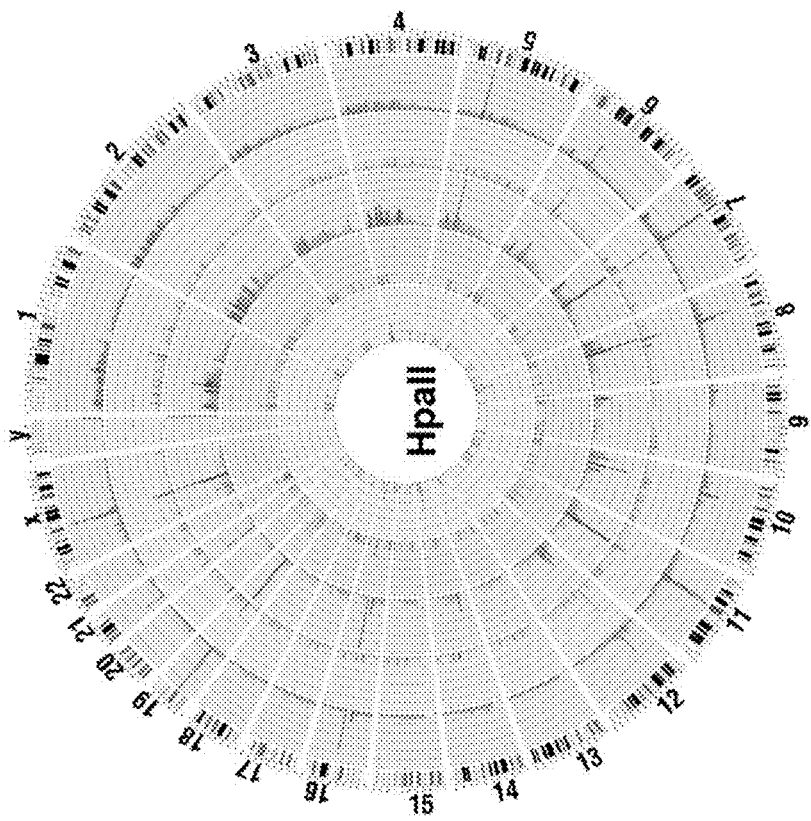
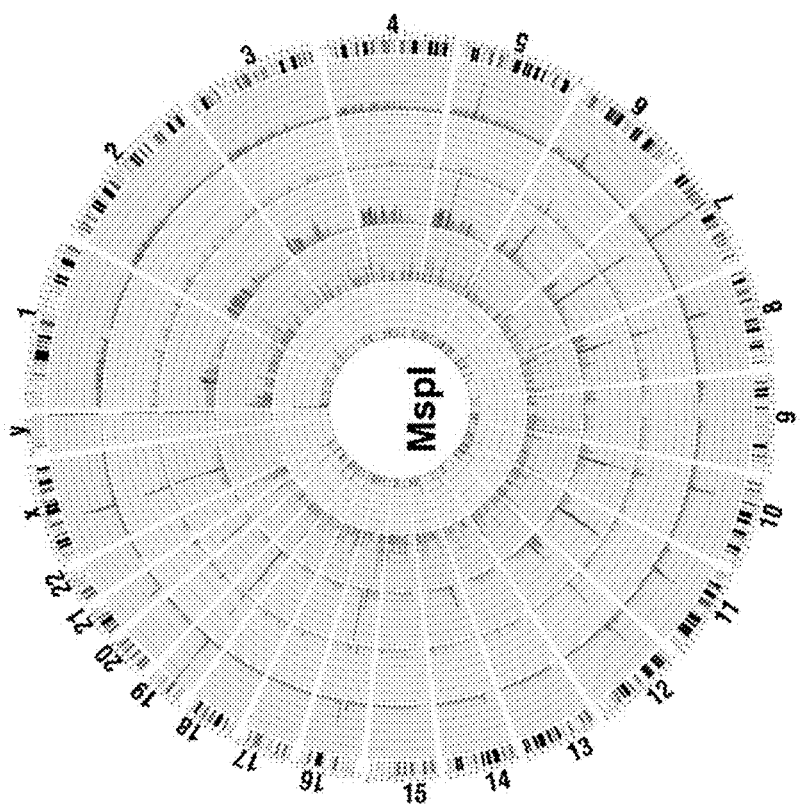
FIG. 9

FIG. 30

| Sample | Liver DNA fraction (fL) deduced by nuclear DNA | mtDNA amount in fragments | Recipient's mtDNA% in | | | Donor's mtDNA% in | | |
|---|---|---|---|---|---|---|---|---|
| | | | All mtDNA | Linear-derived mtDNA | Circular-derived mtDNA | All mtDNA | Linear-derived mtDNA | Circular-derived mtDNA |
| TBR14B (Capture) | | 1.52 | 5.50 | NA | NA | 94.5 | NA | NA |
| TBR14B (BS-Capture) | 38.9 | 3.63 | 51.03 | 10.0 | 41.03 | 48.97 | 47.54 | 1.43 |
| TBR1574 (Capture) | | 0.49 | 12.53 | NA | NA | 57.47 | NA | NA |
| TBR1574 (BS-Capture) | 13.8 | 4.57 | 80.50 | 29.37 | 51.13 | 19.5 | 19.0 | 0.5 |

3000

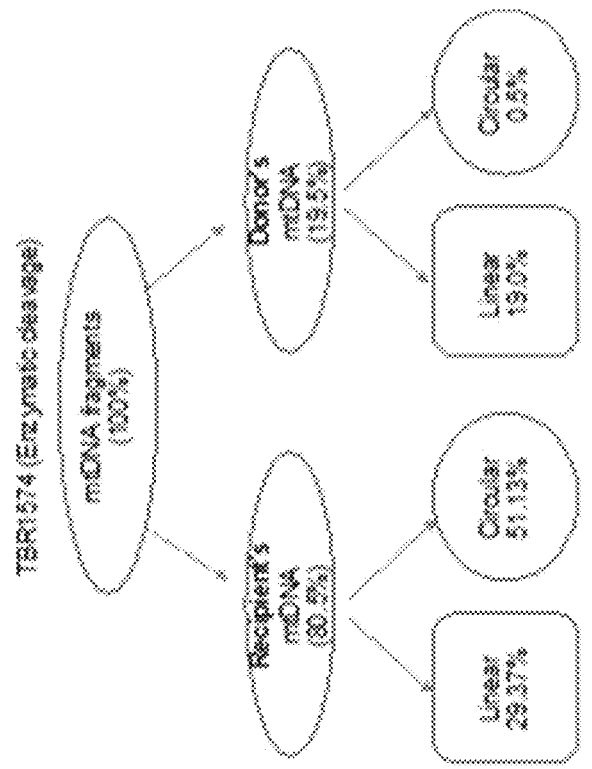
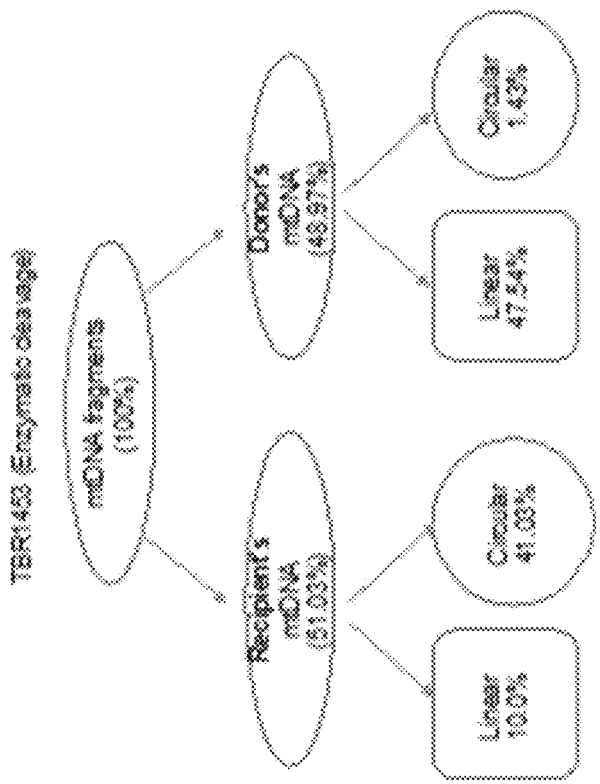
FIG. 31A
FIG. 31B

| Type | Sample | No. of all reads | No. of mtDNA reads | cfmtDNA deaminated/ cfmtDNA (%) | cfmtDNA deamin-d-no-cpg/ cfmtDNA (%) | cfmtDNA methylated/ cfmtDNA (%) | cfmtDNA unchanged/ cfmtDNA (%) |
|---|---|---|---|---|---|---|---|
| Healthy control | TNC80-ez.CS | 40816685 | 663334 | 1.63 | 3.47 | 23.10 | 73.43 |
| | TNC81-ez.CS | 44893686 | 937636 | 2.09 | 3.28 | 24.03 | 72.69 |
| | TNC82-ez.CS | 45406364 | 405953 | 0.89 | 6.98 | 21.23 | 71.79 |
| | TNC83-ez.CS | 62620872 | 201314 | 0.32 | 9.60 | 15.58 | 74.82 |
| | TNC84-ez.CS | 56835735 | 363955 | 0.64 | 5.88 | 15.10 | 79.02 |
| Liver transplant | TBR1453_Ez | 46521154 | 1688136 | 3.63 | 21.31 | 28.61 | 50.08 |
| | TBR1574_Ez | 20417241 | 933953 | 4.57 | 7.65 | 37.37 | 54.98 |

FIG. 33

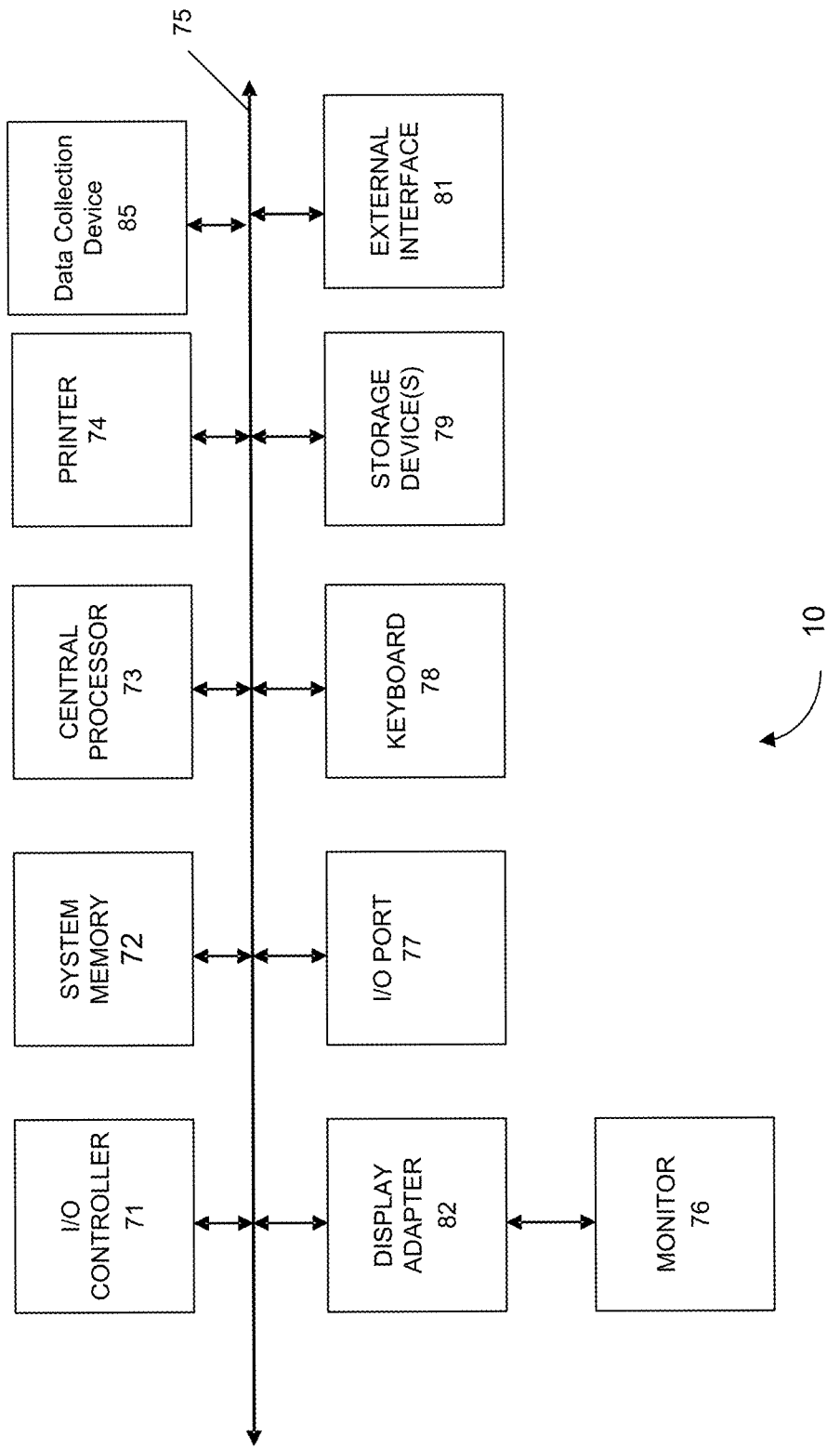

DETERMINING LINEAR AND CIRCULAR FORMS OF CIRCULATING NUCLEIC ACIDS

CROSS-REFERENCES TO RELATED APPLICATION

This application is a nonprovisional of and claims the benefit of U.S. Provisional Patent Application No. 62/823,567, entitled "Determining Linear And Circular Forms Of Circulating Nucleic Acids," filed on Mar. 25, 2019, which is herein incorporated by reference in its entirety for all purposes.

BACKGROUND

Extrachromosomal circular DNAs (eccDNAs) are circular forms of DNA present independent of chromosomal DNA (Zhu et al. Sci Rep. 2017; 7(1):10968). They were first discovered in wheat and boar DNA from electron microscopic observations (Hotta et al. Proc Natl Acad Sci USA. 1965; 53:356-62). Later researchers found that such forms of DNA widely exists in tissues from all organisms (Gaubatz. Mutat Res. 1990; 237(5-6):271-292). Moreover, it has been revealed that eccDNA can be detected in both murine (Kumar et al. Mol Cancer Res. 2017; 15:1197-1205) and human plasma (Zhu et al. Sci Rep. 2017; 7:10968).

Mitochondrial DNA has been detected in the plasma (Chiu et al. Clin Chem 2003; 49: 719-726 and Lo et al. Sci Transl Med 2010; 2: 61-ra91). Measurements have been made of mitochondrial DNA in plasma of cancer patients, but such measurements have not been consistent (Yu M et al. Mitochondrial DNA 2012; 23:329-32; Zachariah R R et al. Obstet Gynecol 2008; 112:843-50; Mehra N et al. Clin Cancer Res 2007; 23:421-6; Kohler et al. Mol Cancer 2009; 8: 105; and Choudhuri et al. Mol Cell Biochem 2014; 386: 259-269).

SUMMARY

Various embodiments of this disclosure can provide techniques for analyzing circular DNA in a biological sample, which may include cellular and/or cell-free DNA, such as plasma. For example, to measure circular DNA, cleaving can be performed to linearize the circular DNA so that they may be sequenced. Example cleaving techniques include restriction enzymes and transposases. Then, one or more criteria can be used to identify linearized DNA molecules, e.g., so as to differentiate from linear DNA molecules. An example criterion is mapping a pair of reversed end sequences to a reference genome. Another example criterion is identification of a cutting tag, e.g., associated with a restriction enzyme or an adapter sequence added by a transposase.

Once circular DNA molecules (e.g., eccDNA and circular mitochondrial DNA) are identified, they may be analyzed (e.g., to determine a count, size profile, and/or methylation) to measure a property of the biological sample. Example properties include detecting copy number aberrations in chromosomal regions, which may in turn be used to detect a level of a disease (e.g., cancer). A level of a disease may be detected directly, with use of aberrations, e.g., using methylation. A further example includes the identification of a tissue type or disease in cellular tissue based on an amount of eccDNA.

Additionally, some embodiments can provide approaches for simultaneously analyzing short linear and circular mtDNA molecules. For example, this disclosure allows (1) quantifying the relative quantity between linear and circular forms of cell-free mtDNA molecules in the plasma DNA pool, e.g., to determine a level of disease; and (2) deducing the tissue of origin of linear and circular mtDNA molecules in the plasma DNA pool, e.g., as part of determining whether a non-hematopoietic tissue or a hematopoietic tissue has the sequence variant. The identification of sequence variants can further be used to identify a disease (e.g., cancer) and original information about the disease.

These and other embodiments of the disclosure are described in detail below. For example, other embodiments are directed to systems, devices, and computer readable media associated with methods described herein.

A better understanding of the nature and advantages of embodiments of the present disclosure may be gained with reference to the following detailed description and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A and 2B show a schematic approach for junction searching approach according to embodiments of the present disclosure.

FIG. 9 shows the genomic locations of eccDNA from one pregnancy plasma sample treated with MspI and HpaII.

FIG. 30 shows a table 3000 illustrating statistics for liver transplant cases according to embodiments of the present disclosure.

FIGS. 31A and 31B show an analysis of linear and circular mtDNA molecules in the plasma of liver transplant cases according to embodiments of the present disclosure.

FIG. 33 shows the difference in the quantity of linear and circular mtDNA between healthy controls and liver transplant patients according to embodiments of the present disclosure.

FIG. 41 shows a block diagram of an example computer system usable with systems and methods according to embodiments of the present disclosure.

TERMS

Figure 1:
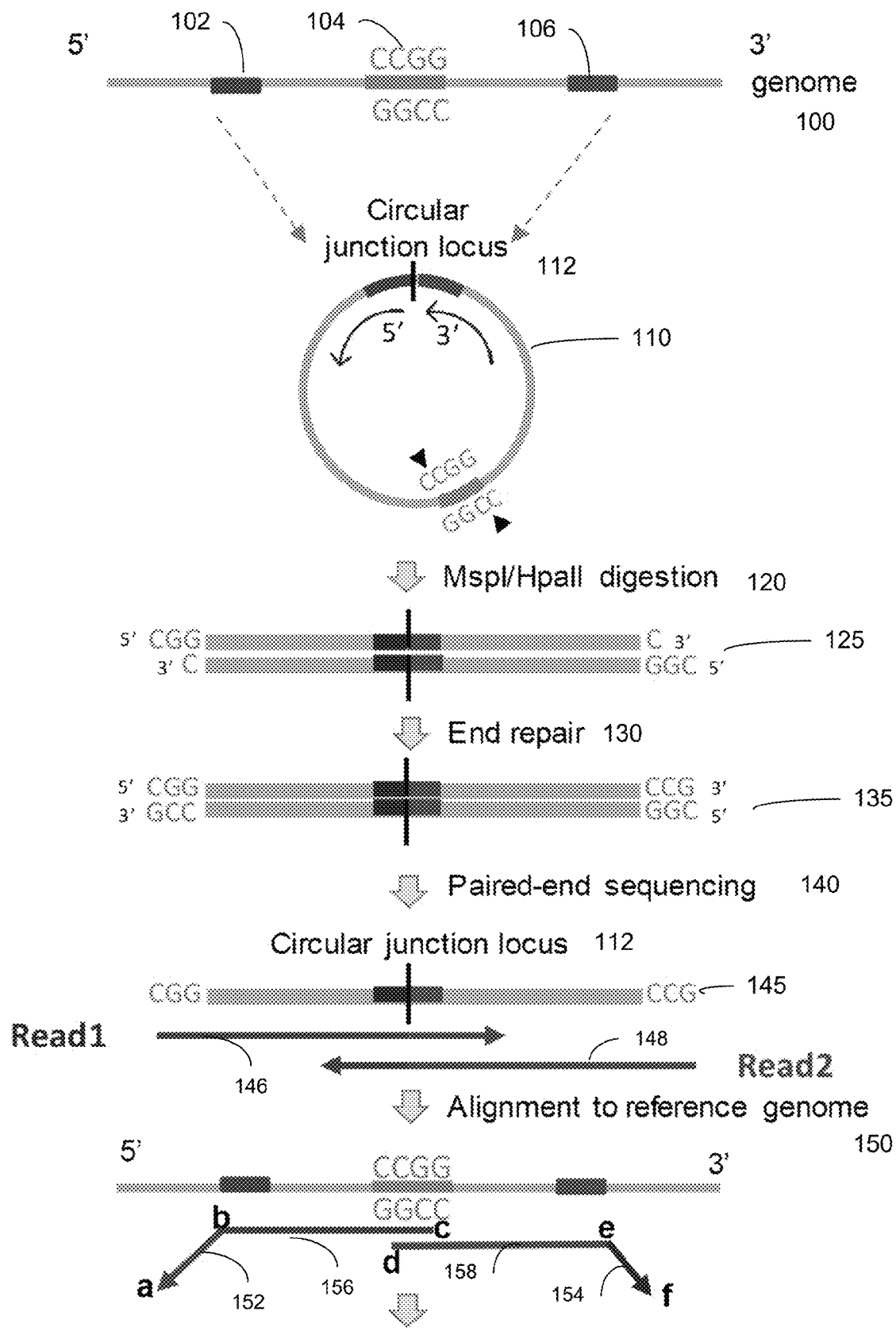
FIG. 1 shows an example technique for eccDNA identification according to embodiments of the present disclosure.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (mother vs. fetus) or to healthy cells vs. tumor cells. "Reference tissues" can correspond to tissues used to determine tissue-specific methylation levels. Multiple samples of a same tissue type from different individuals may be used to determine a tissue-specific methylation level for that tissue type.

A "biological sample" refers to any sample that is taken from a subject (e.g., a human (or other animal), such as a pregnant woman, a person with cancer, or a person suspected of having cancer, an organ transplant recipient or a subject suspected of having a disease process involving an organ (e.g., the heart in myocardial infarction, or the brain in stroke, or the hematopoietic system in anemia) and contains one or more nucleic acid molecule(s) of interest. The biological sample can be a bodily fluid, such as blood, plasma, serum, urine, vaginal fluid, fluid from a hydrocele (e.g. of the testis), vaginal flushing fluids, pleural fluid, ascitic fluid, peritoneal fluid, cerebrospinal fluid, saliva, sweat, tears, sputum, bronchoalveolar lavage fluid, cervical lavage fluid, discharge fluid from the nipple, aspiration fluid from different parts of the body (e.g. thyroid, breast), intraocular fluids (e.g. the aqueous humor), etc. Stool samples can also be used. In various embodiments, the majority of DNA in a biological sample that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at for example, 30,000 g for another 10 minutes to remove residual cells. As part of an analysis of a biological sample, at least 1,000 cell-free DNA molecules can be analyzed. As other examples, at least 10,000 or 50,000 or 100,000 or 500,000 or 1,000,000 or 5,000,000 cell-free DNA molecules, or more, can be analyzed.

The term "fragment" (e.g., a DNA fragment), as used herein, can refer to a portion of a polynucleotide or polypeptide sequence that comprises at least 3 consecutive nucleotides. A nucleic acid fragment can retain the biological activity and/or some characteristics of the parent polypeptide. A nucleic acid fragment can be double-stranded or single-stranded, methylated or unmethylated, intact or nicked, complexed or not complexed with other macromolecules, e.g. lipid particles, proteins. A nucleic acid fragment can be a linear fragment or a circular fragment. A tumor-derived nucleic acid can refer to any nucleic acid released from a tumor cell, including pathogen nucleic acids from pathogens in a tumor cell.

The term "assay" generally refers to a technique for determining a property of a nucleic acid or a sample of nucleic acids (e.g., a statistically significant number of nucleic acids), as well as a property of the subject from which the sample was obtained. An assay (e.g., a first assay or a second assay) generally refers to a technique for determining the quantity of nucleic acids in a sample, genomic identity of nucleic acids in a sample, the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art may be used to detect any of the properties of nucleic acids mentioned herein. Properties of nucleic acids include a sequence, quantity, genomic identity, copy number, a methylation state at one or more nucleotide positions, a size of the nucleic acid, a mutation in the nucleic acid at one or more nucleotide positions, and the pattern of fragmentation of a nucleic acid (e.g., the nucleotide position(s) at which a nucleic acid fragments). The term "assay" may be used interchangeably with the term "method". An assay or method can have a particular sensitivity and/or specificity (e.g., based on selection of one or more cutoff values), and their relative usefulness as a diagnostic tool can be measured using Receiver Operating Characteristic (ROC) Area-Under-the-Curve (AUC) statistics.

A "sequence read" refers to a string of nucleotides sequenced from any part or all of a nucleic acid molecule. For example, a sequence read may be the entire nucleic acid fragment that exists in the biological sample. Also as an example, a sequence read may be a short string of nucleotides (e.g., 20-150 bases) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification, or based on biophysical measurements, such as mass spectrometry. A sequence read may be obtained from a single-molecule sequencing. As part of an analysis of a biological sample, at least 1,000 sequence reads can be analyzed. As other examples, at least 10,000 or 50,000 or 100,000 or 500,000 or 1,000,000 or 5,000,000 sequence reads, or more, can be analyzed. A sequence read can be aligned (mapped) to a reference genome to determine its location in the reference genome. Various software packages can be used to perform such alignment.

"Single-molecule sequencing" refers to sequencing of a single template DNA molecule to obtain a sequence read without the need to interpret base sequence information from clonal copies of a template DNA molecule. The single-molecule sequencing may sequence the entire molecule or only part of the DNA molecule. A majority of the DNA molecule may be sequenced, e.g., greater than 50%, 55%, 60%, 65%, 70%, 75%, 80%, 85%, 90%, 95%, or 99%. A sequence read (or reads from both ends) can be aligned to a reference genome. When both ends are aligned (e.g., as part of a read of the entire fragment or for paired-ends), greater accuracy can be achieved in the alignment and a length of the fragment can be obtained.

A sequence read can include an "ending sequence" (or "end sequence") associated with an end of a fragment. The ending sequence can correspond to the outermost N bases of the fragment, e.g., 2-30 bases at the end of the fragment. If a sequence read corresponds to an entire fragment, then the sequence read can include two ending sequences. When paired-end sequencing provides two sequence reads that correspond to the ends of the fragments, each sequence read can include one ending sequence.

A "sequence motif" (or just "motif") may refer to a short, recurring pattern of bases in DNA fragments (e.g., cell-free DNA fragments). A sequence motif can occur at an end of a fragment, and thus be part of or include an ending sequence. An "end motif" can refer to a sequence motif for an ending sequence that preferentially occurs at ends of DNA fragments, potentially for a particular type of tissue. An end motif may also occur just before or just after ends of a fragment, thereby still corresponding to an ending sequence.

A "cutting tag" may refer to a short sequence at an end of a DNA fragment, indicating that DNA had been cut at that position. As examples, a cutting tag may be generated from enzyme digestion (restriction enzyme or transposase) and may be either a distinct tag or duplicated sequence. A "cutting tag" may be an "end motif" when a restriction enzyme is used.

As used herein, the term "locus" or its plural form "loci" is a location or address of any length of nucleotides (or base pairs). A locus may have a variation across genomes.

An "ending position" or "end position" (or just "end") can refer to the genomic coordinate or genomic identity or nucleotide identity of the outermost base, i.e., at the extremities, of a cell-free DNA molecule, e.g., plasma DNA molecule. The end position can correspond to either end of a DNA molecule. In this manner, if one refers to a start and end of a DNA molecule, both may correspond to an ending position. In practice, one end position is the genomic coordinate or the nucleotide identity of the outermost base on one extremity of a cell-free DNA molecule that is detected or determined by an analytical method, such as but not limited to massively parallel sequencing or next-generation sequencing, single molecule sequencing, double- or single-stranded DNA sequencing library preparation protocols, polymerase chain reaction (PCR), or microarray. Such in vitro techniques may alter the true in vivo physical end(s) of the cell-free DNA molecules. Thus, each detectable end may represent the biologically true end or the end is one or more nucleotides inwards or one or more nucleotides extended from the original end of the molecule e.g., 5' blunting and 3' filling of overhangs of non-blunt-ended double stranded DNA molecules by the Klenow fragment. The genomic identity or genomic coordinate of the end position may be derived from results of alignment of sequence reads to a human reference genome, e.g., hg19. It may be derived from a catalog of indices or codes that represent the original coordinates of the human genome. It may refer to a position or nucleotide identity on a cell-free DNA molecule that is read by but not limited to target-specific probes, mini-sequencing, DNA amplification. The term "genomic position" can refer to a nucleotide position in a polynucleotide (e.g., a gene, a plasmid, a nucleic acid fragment, a viral DNA fragment, or a genome). The term "genomic position" is not limited to nucleotide positions within a genome (e.g., the haploid set of chromosomes in a gamete or microorganism, or in each cell of a multicellular organism).

The term "alleles" refers to alternative DNA sequences at the same physical genomic locus, which may or may not result in different phenotypic traits. In any particular diploid organism, with two copies of each chromosome (except the sex chromosomes in a male human subject), the genotype for each gene comprises the pair of alleles present at that locus, which are the same in homozygotes and different in heterozygotes. A population or species of organisms typically include multiple alleles at each locus among various individuals. A genomic locus where more than one allele is found in the population is termed a polymorphic site. Allelic variation at a locus is measurable as the number of alleles (i.e., the degree of polymorphism) present, or the proportion of heterozygotes (i.e., the heterozygosity rate) in the population. As used herein, the term "polymorphism" refers to any inter-individual variation in the human genome, regardless of its frequency. Examples of such variations include, but are not limited to, single nucleotide polymorphism, simple tandem repeat polymorphisms, insertion-deletion polymorphisms, mutations (which may be disease causing) and copy number variations. The term "haplotype" as used herein refers to a combination of alleles at multiple loci that are transmitted together on the same chromosome or chromosomal region. A haplotype may refer to as few as one pair of loci or to a chromosomal region, or to an entire chromosome or chromosome arm.

The term "fractional fetal DNA concentration" is used interchangeably with the terms "fetal DNA proportion" and "fetal DNA fraction," and refers to the proportion of fetal DNA molecules that are present in a biological sample (e.g., maternal plasma or serum sample) that is derived from the fetus (Lo et al, Am J Hum Genet. 1998; 62:768-775; Lun et al, Clin Chem. 2008; 54:1664-1672). Similarly, tumor fraction or tumor DNA fraction can refer to the fractional concentration of tumor DNA in a biological sample.

The terms "size profile" and "size distribution" generally relate to the sizes of DNA fragments in a biological sample. A size profile may be a histogram that provides a distribution of an amount of DNA fragments at a variety of sizes. Various statistical parameters (also referred to as size parameters or just parameter) can distinguish one size profile to another. One parameter is the percentage of DNA fragment of a particular size or range of sizes relative to all DNA fragments or relative to DNA fragments of another size or range.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter. A separation value is an example of a parameter. A "separation value" (or relative abundance) corresponds to a difference or a ratio involving two values, e.g., two amounts of DNA molecules, two fractional contributions, or two methylation levels, such as a sample (mixture) methylation level and a reference methylation level. The separation value could be a simple difference or ratio. As examples, a direct ratio of x/y is a separation value, as well as x/(x+y). The separation value can include other factors, e.g., multiplicative factors. As other examples, a difference or ratio of functions of the values can be used, e.g., a difference or ratio of the natural logarithms (ln) of the two values. A separation value can include a difference and/or a ratio. A "methylation level" is an example of a relative abundance, e.g., between methylated DNA molecules (e.g., at particular sites) and other DNA molecules (e.g., all other DNA molecules at particular sites or just unmethylated DNA molecules). The amount of other DNA molecules can act as a normalization factor. As another example, an intensity of methylated DNA molecules (e.g., fluorescent or electrical intensity) relative to intensity of all or unmethylated DNA molecules can be determined. The relative abundance can also include an intensity per volume.

A "classification" can refer to any number(s) or other characters(s) that are associated with a particular property of a sample. For example, a "+" symbol (or the word "positive") could signify that a sample is classified as having deletions or amplifications. In another example, the term "classification" can refer to an amount of tumor tissue in the subject and/or sample, a size of the tumor in the subject and/or sample, a stage of the tumor in the subject, a tumor load in the subject and/or sample, and presence of tumor metastasis in the subject. The classification can be binary (e.g., positive or negative) or have more levels of classification (e.g., a scale from 1 to 10 or 0 to 1).

The term "cutoff" and "threshold" can refer to a predetermined number used in an operation. A threshold or cutoff value may be a value above or below which a particular classification applies, e.g., a classification of a condition, such as whether a subject has a condition or a severity of the condition. A cutoff or threshold may be "a reference value" or derived from a reference value that is representative of a particular classification or discriminates between two or more classifications. A cutoff may be predetermined with or without reference to the characteristics of the sample or the subject. For example, cutoffs may be chosen based on the age or sex of the tested subject. A cutoff may be chosen after and based on output of the test data. For example, certain cutoffs may be used when the sequencing of a sample reaches a certain depth. As another example, reference subjects with known classifications of one or more conditions and measured characteristic values (e.g., a methylation level, a statistical size value, or a count) can be used to determine reference levels to discriminate between the different conditions and/or classifications of a condition (e.g., whether the subject has the condition). A reference value can be selected as representative of one classification (e.g., a mean) or a value that is between two clusters of the metrics (e.g., chosen to obtain a desired sensitivity and specificity). As another example, a reference value can be determined based on statistical simulations of samples. Any of these terms can be used in any of these contexts.

A "non-hematopoietic tissue source" refers to any organ other than the blood system. Examples include the liver, lung, heart, brain, a non-hematopoietic cancer, the placenta, etc.

The term "nuclear DNA" refers to DNA originating from the nucleus of a cell. A "nuclear genome" corresponds to the nuclear DNA originating from the nucleus of a cell. The "mitochondrial genome" corresponds to the DNA originating from the mitochondria of a cell.

The term "level of cancer" (or more generally "level of disease" or "level of condition" or "level of disorder") can refer to whether cancer exists (i.e., presence or absence), a stage of a cancer, a size of tumor, whether there is metastasis, the total tumor burden of the body, the cancer's response to treatment, and/or other measure of a severity of a cancer (e.g. recurrence of cancer). The level of cancer may be a number (e.g., a probability) or other indicia, such as symbols, alphabet letters, and colors. The level may be zero. The level of cancer may also include premalignant or precancerous conditions (states). The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a patient dying of cancer, or the chance of the cancer progressing after a specific duration or time, or the chance of cancer metastasizing. Detection can mean 'screening' or can mean checking if someone, with suggestive features of cancer (e.g. symptoms or other positive tests), has cancer.

The term "sequence imbalance" or "aberration" as used herein means any significant deviation as defined by at least one cutoff value in a quantity of the clinically relevant chromosomal region from a reference quantity. A sequence imbalance can include chromosome dosage imbalance, allelic imbalance, mutation dosage imbalance, copy number imbalance, haplotype dosage imbalance, and other similar imbalances. As an example, an allelic imbalance can occur when a tumor has one allele of a gene deleted or one allele of a gene amplified or differential amplification of the two alleles in its genome, thereby creating an imbalance at a particular locus in the sample. As another example, a patient could have an inherited mutation in a tumor suppressor gene. The patient could then go on to develop a tumor in which the non-mutated allele of the tumor suppressor gene is deleted. Thus, within the tumor, there is mutation dosage imbalance. When the tumor releases its DNA into the plasma of the patient, the tumor DNA will be mixed in with the constitutional DNA (from normal cells) of the patient in the plasma. An aberration can include a deletion or amplification of a chromosomal region.

"DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as N6-methyladenine, has also been reported.

A "site" (also called a "genomic site") corresponds to a single site, which may be a single base position or a group of correlated base positions, e.g., a CpG site or larger group of correlated base positions. A "locus" may correspond to a region that includes multiple sites. A locus can include just one site, which would make the locus equivalent to a site in that context.

The "methylation index" for each genomic site (e.g., a CpG site) can refer to the proportion of DNA fragments (e.g., as determined from sequence reads) showing methylation at the site over the total number of reads covering that site. A "read" can include information (e.g., methylation status at a site) obtained from a DNA fragment. A read can be obtained using reagents (e.g. primers or probes) that preferentially hybridize to DNA fragments of a particular methylation status. Typically, such reagents are applied after treatment with a process that differentially modifies or differentially recognizes DNA molecules depending of their methylation status, e.g. bisulfite conversion, or methylation-sensitive restriction enzyme, or methylation binding proteins, or anti-methylcytosine antibodies, or single molecule sequencing techniques that recognize methylcytosines and hydroxymethylcytosines.

The "methylation density" of a region can refer to the number of reads at sites within the region showing methylation divided by the total number of reads covering the sites in the region. The sites may have specific characteristics, e.g., being CpG sites. Thus, the "CpG methylation density" of a region can refer to the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g. 500 bp, 5 kb, 10 kb, 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" can refer the number of cytosine sites, "C's", that are shown to be methylated (for example unconverted after bisulfite conversion) over the total number of analyzed cytosine residues, i.e. including cytosines outside of the CpG context, in the region. The methylation index, methylation density and proportion of methylated cytosines are examples of "methylation levels." Apart from bisulfite conversion, other processes known to those skilled in the art can be used to interrogate the methylation status of DNA molecules, including, but not limited to enzymes sensitive to the methylation status (e.g. methylation-sensitive restriction enzymes), methylation binding proteins, single molecule sequencing using a platform sensitive to the methylation status (e.g. nanopore sequencing (Schreiber et al. Proc Natl Acad Sci USA 2013; 110: 18910-18915) and by the Pacific Biosciences single molecule real time analysis (Flusberg et al. Nat Methods 2010; 7: 461-465)). A methylation metric of a DNA molecule can correspond to a percentage of sites (e.g., CpG sites) that are methylated. The methylation metric can be specified as an absolute number or a percentage, which may be referred to as a methylation density of a molecule.

"Methylation-aware sequencing" refers to any sequencing method that allows one to ascertain the methylation status of a DNA molecule during a sequencing process, including, but not limited to bisulfite sequencing, or sequencing preceded by methylation-sensitive restriction enzyme digestion, immunoprecipitation using anti-methylcytosine antibody or methylation binding protein, or single molecule sequencing that allows elucidation of the methylation status. A "methylation-aware assay" or "methylation-sensitive assay" can include both sequencing and non-sequencing based methods, such as MSP, probe based interrogation, hybridization, restriction enzyme digestion followed by density measurements, anti-methylcytosine immunoassays, mass spectrometry interrogation of proportion of methylated cytosines or hydroxymethylcytosines, immunoprecipitation not followed by sequencing, etc.

The terms "control", "control sample", "reference", "reference sample", "normal", and "normal sample" may be interchangeably used to generally describe a sample that does not have a particular condition, or is otherwise healthy. In an example, a method as disclosed herein may be performed on a subject having a tumor, where the reference sample is a sample taken from a healthy tissue of the subject. In another example, the reference sample is a sample taken from a subject with the disease, e.g. cancer or a particular stage of cancer. A reference sample may be obtained from the subject, or from a database. The reference generally refers to a reference genome that is used to map sequence reads obtained from sequencing a sample from the subject. A reference genome generally refers to a haploid or diploid genome to which sequence reads from the biological sample and the constitutional sample can be aligned and compared.

For a haploid genome, there is only one nucleotide at each locus. For a diploid genome, heterozygous loci can be identified, with such a locus having two alleles, where either allele can allow a match for alignment to the locus. A reference genome may correspond to a virus, e.g., by including one or more viral genomes.

The phrase "healthy," as used herein, generally refers to a subject possessing good health. Such a subject demonstrates an absence of any malignant or non-malignant disease. A "healthy individual" may have other diseases or conditions, unrelated to the condition being assayed, that may normally not be considered "healthy".

The terms "cancer" or "tumor" may be used interchangeably and generally refer to an abnormal mass of tissue wherein the growth of the mass surpasses and is not coordinated with the growth of normal tissue. A cancer or tumor may be defined as "benign" or "malignant" depending on the following characteristics: degree of cellular differentiation including morphology and functionality, rate of growth, local invasion, and metastasis. A "benign" tumor is generally well differentiated, has characteristically slower growth than a malignant tumor, and remains localized to the site of origin. In addition, a benign tumor does not have the capacity to infiltrate, invade, or metastasize to distant sites. A "malignant" tumor is generally poorly differentiated (anaplasia), has characteristically rapid growth accompanied by progressive infiltration, invasion, and destruction of the surrounding tissue. Furthermore, a malignant tumor has the capacity to metastasize to distant sites. "Stage" can be used to describe how advance a malignant tumor is. Early stage cancer or malignancy is associated with less tumor burden in the body, generally with less symptoms, with better prognosis, and with better treatment outcome than a late stage malignancy. Late or advanced stage cancer or malignancy is often associated with distant metastases and/or lymphatic spread.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" or "approximately" can mean within an order of magnitude, within 5-fold, and more preferably within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

The terminology used herein is for the purpose of describing particular cases only and is not intended to be limiting. As used herein, the singular forms "a", "an" and "the" are intended to include the plural forms as well, unless the context clearly indicates otherwise. The term "based on" is intended to mean "based at least in part on." Furthermore, to the extent that the terms "including", "includes", "having", "has", "with", or variants thereof are used in either the detailed description and/or the claims, such terms are intended to be inclusive in a manner similar to the term "comprising."

DETAILED DESCRIPTION

Since the discovery of extrachromosomal circular DNA (eccDNA), researchers have tried various approaches to gain knowledge of this special form of DNA. Earlier reports utilized electron microscopy and Southern blotting in the visualization and quantification of eccDNA (Gaubatz. Mutat Res. 1990; 237:271-292). Such methods could only gain limited information about the number and parts of the sequences (as informed by the hybridization of probes) of eccDNA. More detailed information, such as the exact complete sequences and the genomic locations of eccDNAs were not readily available. And, the use of eccDNAs to measure properties of the biological sample (e.g., for diagnostic purposes) has been limited. Through some embodiments of this disclosure, we have advanced the approaches for eccDNA analysis.

In contrast to plasma DNA fragments originating from nuclear DNA molecules, cell-free mitochondrial DNA (mtDNA) fragments derived from the mitochondrial genome displayed completely different size characteristics (Lo et al., Sci Transl Med. 2010; 2:61ra91; Jiang et al., Proc Natl Acad Sci USA. 2015; 112:E1317-E1325). For circulating mitochondrial DNA, there was a much higher proportion of shorter DNA molecules, when compared with the situation for nuclear DNA in plasma. Furthermore, the 166-bp modal peak and 10-bp periodic small peaks are no longer shown in the size profile of mitochondrial DNA in plasma. Such disappearance of the nucleosomal features for plasma mitochondrial DNA molecules might be due to the lack of histone packing in the mitochondrial genome (Lo et al., Sci Transl Med. 2010; 2:61ra91; Jiang et al., Proc Natl Acad Sci USA. 2015; 112:E1317-E1325).

Using massively parallel sequencing, Jiang et al. reported that the increase of cell-free mtDNA molecules was associated with patients with hepatocellular carcinoma (HCC) in comparison with healthy controls, HBV carriers and cirrhosis subjects (Jiang et al., Proc Natl Acad Sci USA. 2015; 112:E1317-E1325). However, such massively parallel sequencing is only able to efficiently sequence the linearly fragmented DNA such as naturally fragmented cell-free nuclear and mitochondrial DNA, and artificially sheared or cleaved genomic DNA. The mitochondrial genome is known to be a form of naturally occurring circularized double-stranded DNA with ~16.5 kb in size. Here, we hypothesized that cell-free mtDNA analyzed by Jiang et al (Jiang et al., Proc Natl Acad Sci USA. 2015; 112:E1317-E1325) was likely to be degraded linear mtDNA, rather than circular mtDNA.

Through some embodiments of this disclosure, we have advanced the analysis of circular mtDNA. For example, this disclosure can provide techniques for analyzing circular DNA in a biological sample (e.g., including cell-free DNA, such as plasma). For instance, to measure circular DNA, cleaving can be performed to linearize the circular DNA so that they may be sequenced. Example cleaving techniques include restriction enzymes and transposases. Then, one or more criteria can be used to identify linearized DNA molecules, e.g., so as to differentiate from linear DNA molecules. An example criterion is mapping a pair of reversed end sequences to a reference genome. Another example criterion is identification of a cutting tag, e.g., associated with a restriction enzyme or an adapter sequence added by a transposase. Once circular DNA molecules (e.g., eccDNA and circular mitochondrial DNA) are identified, they may be analyzed (e.g., to determine a count, size profile, and/or methylation) to measure a property of the biological sample, including genetic properties and level of a disease.

I. Circular Nuclear DNA

According to some embodiments, a work flow first reduces (e.g., to essentially eliminate) linear DNA in the plasma DNA samples by exonuclease digestion (e.g. using exonuclease V). Other techniques can also be used to reduce linear DNA, e.g., cesium chloride-ethidium bromide (CsCl-EB) density gradient centrifugation.

We then followed up this with an approach to open up the circles (e.g., of eccDNA or mitochondrial DNA) to form linearized DNA molecules. The linearization of the eccDNA can be performed in various ways. In one example, we utilize restriction enzyme digestion to open up the circles at particular cleavage sites having a cutting sequence motif, which is a type of cutting tag. In another example, we use a transposase (e.g., via tagmentation) for opening up the circles, e.g., to insert a cutting tag that is recognizable like the cutting sequence motif for restriction enzyme digestion. Library preparation and next-generation sequencing of the resultant linearized DNA can then be performed.

Among the various examples using enzyme digestion, one implementation can use the restriction enzyme MspI (cutting of CCGG sequence; methylation-insensitive). In another implementation, we used the restriction enzyme HpaII (cutting of CCGG sequence; methylation-sensitive). In yet another implementation, we combined data generated through the use of MspI and HpaII to arrive at novel insights of eccDNA.

Restriction enzymes other than MspI and HpaII can be used. As an illustration, DpnI and DpnII, both recognize GATC sequence, could also be used. DpnI cleaves only when the recognition site (A base) is methylated. On the other hand, DpnII is not sensitive to methylation status. The number of bases recognized and cut can vary. For example, both MspI and HpaII are 4-base cutters. Restriction enzymes other than a 4-base cutter can be used, such as 6-base cutters.

When compared to rolling circle amplification of eccDNA (Shibata et al. Science. 2012; 336:82-86) and shearing (e.g., by a nebulizer) to form linearized DNA, an approach using cutting tags (e.g., restriction enzyme or transposase approach) can provide more stringent criteria in the definition (identification) of eccDNA reads. For example, an eccDNA molecule can be accurately identified using two more anchors comprising the known sequence (cutting tag) where a cut has been made (e.g., CCGG fragment ends) and the absence of a gap between the two end sequences of the sequence read(s). Such a signature anchors can be used to accurately identify eccDNA reads and for determining their location in a reference genome. The absence of a gap can be determined using the reference genome via an alignment procedure, as described in more detail below.

This information from the cutting tag (e.g., CCGG read ends) not only facilitates more accurate identification of eccDNA, the complementing information provided by the number of eccDNA detected from methylation-insensitive and methylation-sensitive restriction enzymes also allows one to deduce the methylation levels of the eccDNA. Such information was not available through previously documented approaches. Moreover, the in existence of CCGG fragment ends in the eccDNA fragments (or other recognition sequences specific for other types of restriction enzymes, i.e., other types of cutting tags) can provide insights of the pre-existence of eccDNA damage, which refers to linearization of eccDNA prior to restriction enzyme cutting. Such linearization might result from mechanical shearing during DNA processing, nuclease attacks in blood stream, etc. Such eccDNA molecules, although detected with junctional sites, often lack restriction enzyme cutting motifs at one or both ends of the fragment. Such cases can be referred to as "pre-existent eccDNA damage." Such information was also not obtainable by previously documented approaches. Such information could provide valuable knowledge for the biological mechanisms of eccDNA generation and processing in vivo.

The use of restriction enzyme digestion has been used in the creation of recombinant plasmids for molecular cloning. However, there are clear differences between such an application and the present disclosure. Firstly, eccDNA molecules are generated from the genome of organisms with clear start and end positions when mapped to the genome, whereas such concepts do not exist in a bacterial plasmid. Secondly, the restriction enzyme approaches for eccDNA study can provide insights of the host genome sequences. But for the bacterial plasmid DNA, restriction enzyme digestion approaches only allow one to peek into the plasmid DNA information and not the host genome itself (Shintani et al. Front Microbiol. 2015; 31; 6:242).

The restriction enzyme approach uses the presence of specific recognition sites on the eccDNA in order for its digestion and linearization. A tagmentation approach, which makes use of random cutting of DNA by a transposase, does not require specific DNA sequences. Therefore, the tagmentation approach could potentially provide a higher number of linearized eccDNA for library construction and sequencing. In a previous report, the use of tagmentation for eccDNA analysis in tissues was described (Shoura et al. G3 (Bethesda). 2017; 7(10):3295-3303). Shoura et al used cesium chloride-ethidium bromide density gradient centrifugation to enrich eccDNA from tissue genomic DNA. In contrast, such a step does not need to be performed. Therefore, a tagmentation approach of the present disclosure can be more suitable for plasma DNA and other bodily fluids or stool that include circulating DNA.

A. Principle and Bioinformatics Approach for eccDNA Identification

FIG. 1 shows an example technique for eccDNA identification according to embodiments of the present disclosure. The "blue" bar 102 and the "red" bar 106 in genome 100 indicate two regions that are assumed to be joint together to form extrachromosomal circular DNA (eccDNA). The "cyan" bar indicates a restriction enzyme recognition site 104, which act as cutting tags. For example, the MspI restriction enzyme could recognize and cleave CCGG sites. Such specific cutting would linearize the original circular DNA molecules. The resulting linearized molecules would carry staggered ends, which can be repaired though the end-repair step to form blunt-end molecules. Such blunt DNA ends would carry the cutting tag (i.e. 5' CGG and 3' CGG motifs). Subsequently, the blunt-end DNA could be sequenced using different sequencing technologies including, but not limited to, the Illumina platform, Ion Torrent sequencing, etc.

An eccDNA 110 is shown having a circular junction locus 112 that includes the two regions 102 and 106 from genome 100. The ends of region 102 and 106 include nucleotides at two separated genomic locations that are immediately adjacent to one another in eccDNA 110 to form circular junction locus 112. At step 120, digestion is performed at site 104 to generate linearized DNA molecule 125. At step 130, end repair is performed, e.g., as described above, repaired linearized DNA molecule 135. At step 140, sequencing (e.g., paired-end sequencing or single molecule sequencing) is performed to obtain sequence 145, which includes circular junction locus 112. As shown, sequence 145 can include read1 and read2.

If we sequenced read1 and read2 with a sufficient read length, there is a high likelihood to have sequence reads across the circular junction locus 112 (indicated by the chimeric arrows) in the step of paired-end sequencing. Read1 extends from the left end of linearized DNA molecule 125, where read1 is blue on the left side of circular junction locus 112 and red to the right of circular junction locus 112. Read2 extends from the right end of linearized DNA molecule 125, where read2 is red on the right side of circular junction locus 112 and blue to the left of circular junction locus 112.

At step 150, alignment is performed to the reference genome. When read1 and/or read2 cover the circular junction locus 112, in the alignment results, we would observe read1 and read2 sequences of linearized molecules (e.g., cutting by MspI) mapping to a reference genome in unique mapping directionalities. For illustration purpose, we define an unmapped segment 152 (red arrow after the alignment step, "b→a" segment) in read1, which would correspond the sequence across the junction derived from the other genomic region being joint to form a circular DNA. Similarly, we define an unmapped segment 154 (blue arrow after the alignment step, "e→f" segment) in read2, which would correspond the sequence across the junction derived from the other genomic region being joint to form a circular DNA molecule.

Such unique mapping directionalities are covered by the below two scenarios that involve a reversed direction between the read and the reference genome:
  a. Read1 would be aligned in a reversed strand and read2 would be aligned in a forward strand when read1 smallest mapping coordinate of segment "b→c" (i.e. b) is equal to or smaller than read2 smallest mapping coordinate of segment "d→e" (i.e. d).
  b. Read1 would be aligned in a forward strand and read2 would be aligned in a reversed strand when read2 smallest mapping coordinate is equal to or smaller than read1 smallest mapping coordinate (not shown in FIG. 1).

Such unique mapping directionalities were different from conventional mapping directions for a pair of paired-end reads originating from an initially linear DNA. Thus, such criteria can be used to identify a circular molecule. For example, read1 is fully aligned in a forward strand and read2 is fully aligned in a reversed strand when read1 smallest mapping coordinate is equal to or smaller than read2 smallest mapping coordinates; or read1 is fully aligned in a reversed strand and read2 is fully aligned in a forward strand when read2 smallest mapping coordinates are equal to or smaller than read1 smallest mapping coordinates. Bioinformatically, searching the mapping sites in the reference genome of the unmapped segments present in read1 and/or read2 would allow for delineating the junctions. The distance between junction sites deduced from the unmapped segments from a fragment would indicate the size of a circular DNA. For example, the distance between regions 102 and 104 provide the size of the circular DNA.

Another feature is that there were two nucleotides overlapped between the mapped read1 and read2 if a circular DNA was cut only once. Such two nucleotides overlapped sequence between read1 and read2 was introduced by the staggered ends (i.e. jagged end) created by MspI or HpaII, or other digestion enzyme. MspI or HpaII would make two staggered single-stranded breaks and the distance between two breaks would be 2 bp. Such 5' protruding 2-nt single-stranded ends (complementary to each other) would be filled to form blunt ends during the end-repair step. Therefore, the resultant DNA sequences would carry 2 bp overlap between ends of read1 and read2 sequences. In other words, during the library preparation step, there will be an "end repair" step, which will complete the jagged ends into blunt ends by adding two nucleotides to each end. Therefore, the resultant DNA sequences will have two blunt ends instead of two jagged ends. When the two sequencing reads are aligned to the genome, the two nucleotides added during the end repair steps will appear as two extra base pairs that overlap between two reads, which can be used in addition or alternatively to identify a circular NDA molecule.

Taken together, in an example eccDNA identification approach, there can be four "diagnostic features", including:
  a. Circular DNA specific mapping directions (directionality), as provided in (a) and (b) above;
  b. Junction-aware reads (only a portion of an ending sequence mapping to the reference genome);
  c. Restriction enzyme cutting tags;
  d. Two overlapped bases in 5' ends of read1 and read2 sequences.

Such diagnostic features can greatly improve the specificity in identifying the genome-wide eccDNA molecules in plasma DNA. In some implementations, sequencing reads fulfilling at least one of these "diagnostic features" can be defined as a candidate circular DNA. For a circular DNA being cut multiple times by a restriction enzyme, read1 and read2 would not bear repeated sequences (overlapped bases) between each other. In other implementations, only one read from a pair might cross the junction site and the other would not carry the junction. As another example, both reads from a pair would not carry a junction, but show unique mapping directions implying a circular DNA. In yet another example, even though one could not directly observe the complete restriction enzyme cutting tags in the sequencing reads, one could retrieve the reference sequence from the reference genome between these deduced junction sites of one circular DNA. Then one could bioinformatically investigate if any restriction enzyme cutting tags (motifs) exists in such a retrieved reference sequence. Such inferred restriction enzyme cutting motifs would increase the confidence that the identification of a circular DNA species was indeed correct.

Accordingly, a method can use a restriction enzyme as part of analyzing eccDNA. Such a technique can be used in combination with other methods described herein, e.g., for analysis of eccDNA as well as mtDNA. Downstream analysis can include measurement of properties of the sample using the detection of the circular DNA.

In step 1, a biological sample of an organism can be received. Examples of biological samples are provided herein, such as plasma and serum. The biological sample includes a plurality of extrachromosomal circular DNA (eccDNA) molecules. The eccDNA may be from any number of chromosomes, including the autosomes and/or sex chromosomes. Each of the plurality of eccDNA molecules includes a junction at which nucleotides at two separated genomic locations are immediately adjacent to one another. Junction 112 is an example of such a junction with regions 102 and 106 including such two separated genomic locations that are immediately adjacent to one another.

In step 2, digestion is performed using a restriction enzyme. In some implementations, more than one type of restriction enzyme can be used. Digesting the plurality of eccDNA molecules can form a set of linearized DNA molecules that each includes the junction. Each restriction enzyme can cut at a different motif, with the resulting linearized DNA fragments having a different cutting tag. The term "linearized DNA fragments" differs from a "linear DNA fragment," which was already linear before any digestion.

In step 3, for each of the linearized DNA molecules, sequencing of at least both ends of the linearized DNA molecules can be performed to obtain one or more sequence reads. The one or more sequence reads may or may not include the junction. If a read does not include the junction, an eccDNA molecule can still be identified using the directionality of the mapping, as described in table 1. In some embodiments, two sequence reads (one for each end) can be obtained. In other embodiments, a single sequence read of the entire linearized DNA molecule can include both ends, as is described herein.

After the sequence reads are obtained, the sequence reads can be mapped (aligned) to a reference genome, e.g., to see if they map in a reverse orientation. If they do map in a reverse orientation (example criterion), then the correspond linearized DNA molecule can be identified as originally being circular. Accordingly, for each of the linearized DNA molecules, a pair of end sequences for the linearized DNA molecule from the one or more sequence reads can be selected. The pair of end sequences do not include the junction. An example of such end sequences are end sequence 146 and end sequence 148 in FIG. 1. A direction of each of the pair of end sequences is reversed to obtain a pair of reversed end sequences. An example of such reversed end sequences are reversed end sequence 156 and reversed end sequence 158. The pair of reversed end sequences can then be mapped to a reference genome.

The mapped reversed end sequences can be analyzed to measure a property of the biological sample. Examples of such measurements are provided herein. Such analysis can use a collective value (e.g., count, size, or methylation) of the detected eccDNA. Accordingly, the method can further include identifying the linearized DNA molecule as originating from an eccDNA molecule based on the pair of reversed end sequences mapping to the reference genome (other criterion provided in table 1 below), and determining a collective value of the identified eccDNA molecules, wherein analyzing the mapped reversed end sequences to measure the property of the biological sample uses the collective value.

B. Identification Technique

As explained above, various criteria can be used to identify the circular DNA molecules. Additionally, various procedures may be used in the analysis of the raw sequence reads (e.g., read1 and read2 from FIG. 1) to identify one or more of the properties of circular DNA.

The raw sequence reads can be pre-processed. For example, the duplicated reads, sequencing adapters, and low-quality bases on the 3' end of a sequencing read can be removed. Further, a specified number of bases of paired-end reads (or from the ends of a single-molecule read) can be selected for alignment.

1. Putative eccDNA Identification

The bioinformatically truncated read1 and read2 consisting of the first 50 bp of read1 and read2 in pre-processed paired-end reads can be used for alignment to a human reference genome using an alignment procedure, e.g., Bowtie 2 (Langmead et al. Nat Methods. 2012; 9:357-9) in a paired-end mode. Other alignment techniques can also be used. Other lengths of each read may be used besides 50 bp, e.g., at least 20, 25, 30, 35, 40, or 45 bp. A first pass at alignment can try a standard orientation, e.g., read1 is aligned with the left end at a lower genomic position than the last based in the read. For those paired-end reads that are aligned normally (i.e., in a forward direction), the mapping directionality regarding read1 and read2 would be determined in a first pass. In contrast to conventionally properly mapped paired ends, if a fragment's read1 and read2 corresponded to circular DNA, the forward orientation would not provide proper alignment of the pair, as such reads have circular DNA specific mapping directions (FIG. 1).

If the pair of reads are not aligned with a forward orientation, a reverse orientation can be tried in a second alignment pass. As shown in FIG. 1, read1 and read2 are reversed. If the truncated reads can be aligned in a reverse orientation, then the corresponding reads before truncating can be re-aligned to the reference genome. The non-truncated reads may be needed so that they cover the junction. If the read does cover a junction, then it would not fully align to the reference genome, even in a reverse direction, e.g., as shown in FIG. 1. The paired-end reads with at least one read which was not able to be aligned to the reference genome in its full length can be used for the downstream detailed analysis of "diagnostic features" (e.g., 4 above) for eccDNA because such a read that was not able to align the reference genome in an end-to-end mode suggests a junction. These paired-end reads can be deemed as putative reads originating from circular DNA molecules.

2. Probing the Junctions of eccDNA Molecules

To accurately locate the genomic location of an eccDNA with single base resolution, some implementations fine-tuned the realignment for putative read, separately. Taking read1 as an example, the first 20 bp and the last 20 bp from read1 sequences were used as seeds (seed A and seed B, respectively) to determine the candidate genomic regions perhaps carrying a junction. The shortened reads used for searching candidate locations helped to minimize the likelihood a read contained a junctions, which would affect the alignment accuracy and the precise determination of a junction site. In this step, multiple hits (e.g., no more than 10 hits for each seed) may be allowed, so as to maximize the sensitivity to detect the junctions. If seed B sequence was not placed in the downstream of seed A mapping position in the same direction, it would suggest that such read1 would carry a junction.

Next, we used a searching approach to probe the junction in a single base resolution for the read1 that was identified as potentially carrying a junction.

FIGS. 2A and 2B show a schematic approach for junction searching approach according to embodiments of the present disclosure. The search is performed within a read after alignment to the reference genome, e.g., as shown after step 150 in FIG. 1. The read 207 carrying the junction contains two segments (red and blue) of opposite mapping directions, e.g., as shown in FIG. 1.

In FIGS. 2A and 2B, the searching was conducted in a "splitting and matching" manner. We used "splitting site" 205 (as indicated by black dash line) to divide the original read1 sequence into two parts, namely, part A and part B. We iteratively slid the "splitting site" 205 along the whole read except for seed regions 202 and 204 (e.g., of length 20 bp), so as to exhaust all combinations of part A and part B. The sequence to the left of "splitting site" 205, but not including the seed region 202, is part A. The sequence to the right of "splitting site" 205, but not including the seed region 204, is part B. The minimum length for each of part A and part B can be constrained, e.g., not less than 18 bp.

FIG. 2A shows an example where "splitting site" 205 does not overlap with the actual junction 212. After splitting the read, the seed regions 202 and 204 can be realigned, as shown. Then, the part A and part B can respectively be joined, as shown. When the "splitting site" 205 did not overlap with the actual junction 212, part A and part B would show many mismatches if we compared part A and part B to a reference genome after part A and part B were pasted to seed A and seed B, respectively.

FIG. 2B shows an example when the "splitting site" did exactly overlap with the actual junction 212. Part A and part B would show zero mismatch in theory if we compared part A and part B to a reference genome after part A and part B were pasted to seed A and seed B, respectively. Therefore, the "splitting site" 250 in read1 sequence giving a minimum of mismatch among all combinations of part A and part B was identified as a junction. Such a minimum can satisfy a mismatch condition. In other implementations, a seed can be extended until a specified number (e.g., two or more) consecutive positions mismatch with the reference.

Such searching was also applied to read2 sequences independently. The read2 sequence would be used for further improving the specificity. For example, the read2 sequence would have two scenarios: (1) read2 sequence carried a junction as read1. Such junction information should be compatible with the results deduced from read1 sequence. (2) read2 sequence did not carry a junction. In this case, read2 sequence should be fully aligned within the regions demarcated by the sequences at either end of the junction site, which was deduced from the read1 sequences (i.e., part A and part B). The processing orders for read1 and read2 would be exchangeable. In yet another embodiment, the total number of mismatches along the whole read carrying the deduced junction was required to be no more than a specified number (e.g., 2).

3. Classification of eccDNA

According to the diagnostic features for eccDNA including directionality, completeness of cutting tags (e.g., for use of restriction enzyme and transposase), and the distance between 5' ends of read1 and read2) of each queried fragment, the eccDNA can be classified into different groups (Table 1).

Table 1 shows classifications of eccDNA sequencing reads. With a restriction enzyme digestion approach, we identified eccDNA reads with different characteristics and categorized them into 3 types and 3 subtypes. We made use of four criteria for classification, namely: (i) junction (the joining position of the start and the end of the original genomic sequence forming eccDNA), (ii) directionality of the two sequencing reads, (iii) CCGG tag and (iv) the absence of a gap between the two sequencing reads. All of the types satisfy directionality. Such typings could also occur for tagmentation with the presence of a cutting tag (e.g., a 9-bp duplicated sequence, or other sized sequence) at fragment ends as the mark of single/multiple cuttings Type 1 has a complete fragment and the junction is detected. The status of a complete fragment indicates that the cutting tag is intact, i.e., the ends are not damaged, and so the cutting tag can be identified.

Type 2 has an incomplete fragment and the junction is detected. The status of an incomplete fragment indicates that the cutting tag is not intact, i.e., the ends are damaged, and so the cutting tag cannot be identified. For type 2-A, a gap can occur, e.g., when there was further breaking of DNA after restriction enzyme cutting, which would leave a gap between the actual fragment end and the original enzyme cutting site, thereby causing an incomplete fragment. The cutting tag can be inferred in the following manner. For type 2, the 5' ends of reads may not carry full enzyme cutting patterns due to the fragment being incomplete. After the junction site is identified, we can retrieve the reference sequence from the reference genome between these junction sites of one circular DNA. Then, the reference sequence can be analyzed to determine if any CCGG motifs existing in such a retrieved reference sequence. If there exist CCGG motifs, we call them inferred CCGG.

Type 2-A and 2-C can be distinguished in the following manner. For some of the eccDNA fragments, attacks (either physical or chemical) on the molecules might have happened more than once, which would generate not one, but

TABLE 1

| | | Criteria | | | |
|---|---|---|---|---|---|
| Types | Subtypes | Junction | Directionality | CCGG tag | Gap between two ends |
| Type 1: Complete fragment and junction detected | A: circle opened due to one enzyme cut | ✓ | ✓ | Single; complete | x |
| | B: circle opened due to multiple enzyme cuts | ✓ | ✓ | Multiple; complete | ✓ |
| | C: circle opened due to other mechanisms | ✓ | ✓ | None | x |
| Type 2: Incomplete fragment and junction detected | A: circle opened due to one enzyme cut | ✓ | ✓ | Single; inferred | ✓ |
| | B: circle opened due to multiple enzyme cuts | ✓ | ✓ | Multiple; inferred | ✓ |
| | C: circle opened due to other mechanisms | ✓ | ✓ | None | ✓ |
| Type 3: No junction detected | A: circle opened due to one enzyme cut | x | ✓ | Single | — |
| | B: circle opened due to multiple enzyme cuts | x | ✓ | Multiple | ✓ |
| | C: circle opened due to other mechanisms | x | ✓ | None | — | two or more breakings on the DNA molecules. In this case, a small fragment might have fallen out of the original molecule, leaving a gap between two ends of the original fragment. One can look at the eccDNA sequence of a complete molecule. We looked at the sequences between the start and end positions where a molecule was generated from the genome. If there was supposed to be a CCGG site within a 100-bp radius of the fragment ends (or other specified distance), but we could not see it in the sequencing reads, we assumed this molecule was likely to be first cut by the restriction enzyme and then further broken by some other unknown mechanisms, which we classified as 2-A reads. On the other hand, if there was not supposed to be a CCGG site within the 100-bp distance of the fragment end, we assumed that this eccDNA was unlikely to be linearized by restriction enzyme cut.

Type 3 has no junction detected. Each of the types have subtypes: (A) circle opened due to one enzyme cut, (B) circle opened due to multiple enzyme cuts, and (C) circle opened due to other mechanisms. The symbol "---" implies both "yes" and "no" are possible. As for Type 3 reads, we do not distinguish between complete and incomplete fragments. Type 3-A fragments could resemble either Type 1-A or Type 2-A, except that we could not detect the junctional sites. A junction might not be detected if the paired-end 250 bp sequencing length is not be long enough to reach the junctional site, as may happen if that molecule is too long and the junctional site is somewhere in the middle of the fragment. Such an example would occur when there is a 1000 bp eccDNA fragment, and the junctional site is at the 400th bp position. In this case, neither read 1 nor read 2 could reach that junctional site. But, there is still a good reason to believe this is indeed an eccDNA molecule since the mapping directions of read 1 and read 2 would be different from that of a linear molecule.

FIG. 1 shows an example of type 1-A. For type 1-B, there is a gap between the two ends, due to the multiple cuts. For type 1-C, there are no cutting tags identified, but the directionality would cause putative reads to be identified as possibly including a junction, as well as the two ends having a common overhang. And, any of the techniques described above can be used to identify a junction. The analysis for type 2 can be performed in a similar manner as for type 1-C as cutting tags are not identified, but may be inferred. For type 3, the analysis can be performed in a similar manner as the corresponding type 1, but no junction is detected at that step. In such instances, the DNA fragment can be excluded from a downstream analysis. Other implementations can quantify the amount of eccDNA in plasma DNA, which would use knowledge of the number of type C molecules.

C. Uses of Circular DNA

The circular nature of eccDNA means that they will be more resistant to exonuclease clearance in vivo. In addition, exonuclease digestion naturally shortens the length of the digestion target. On the other hand, the circular form of eccDNA molecules exempts them from exonuclease digestion and the resultant shortening. Therefore, eccDNA would be expected to have a longer size distribution than linear DNA and hence would contain more genetic information per molecule. Hence, this special type of DNA might be a more stable and informative biological marker than linear DNA for the detection of genomic abnormalities and non-invasive diagnosis of genetic diseases.

One application of such a technology is for noninvasive prenatal testing (NIPT). However, it was previously not known whether eccDNA of fetal origin is present in maternal plasma. Through the use of the methods described in this disclosure, we have demonstrated, for the first time, that fetal eccDNA is present in maternal plasma. Through the use of such fetal eccDNA, one can perform NIPT. Such eccDNA-based NIPT has the potential advantage that the amount of fetal genetic information obtainable per molecule of fetal eccDNA may be higher than the fetal non-eccDNA in maternal plasma.

Fetal non-eccDNA in maternal plasma is known to have a very short size distribution, with a modal size of around 143 bp (Lo et al Sci Transl Med 2010; 2: 61ra91). Using methods described in this disclosure, we have shown that fetal eccDNA has a longer size distribution than fetal non-eccDNA. This characteristic is highly desirable for NIPT. As an example, the fragile X syndrome is a genetic disorder that is caused by a CGG triplet repeat expansion in the Fragile X mental retardation 1 gene region. Such repeats can occur over 200 times in Fragile X patients, while for normal people, this number is under 40 (Garber et al. Eur J Hum Genet. 2008; 16:666-72). As fetal non-eccDNA molecules in plasma are mainly DNA fragments shorter than 200 bp (Yu et al. Proc Natl Acad Sci USA. 2014; 111: 8583-8588), it will be difficult to find a molecule that contains sequences of more than 200 CGG triplet repeats (over 600 bp). However, the larger sizes of eccDNA will allow higher chances for such molecules to contain a 600 bp-long DNA sequence. Therefore, eccDNAs represent a valuable resource for NIPT (and indeed for other applications outside of the pregnancy context).

In our current study, we sequenced 5 pregnancy cases from the $3^{rd}$ trimester of pregnancy. Upon the successful implementation of our new approaches, we believe that such design could also be used in other pregnancy stages (e.g.: $1^{st}$ and $2^{nd}$ trimesters).

Table 2 shows the numbers of eccDNA molecules detected from different types of reads in one pregnancy case (13007). In Table 2, the numbers are in units of CPM, which is circular DNA per million mapped reads. The measurements were performed for untreated plasma and plasma treated with MspI and HpaII. Plasma DNA without Exonuclease V or restriction enzyme treatment showed very low numbers of eccDNA detected (undetectable in some of the types), whereas plasma DNA from the same case treated with Exonuclease V, followed by MspI digestion or HpaII digestion greatly enhanced the counts of eccDNA molecules detected. This data shows that eccDNA can be detected in plasma.

TABLE 2

|  | 13007 (untreated) | | | 13007 (MspI) | | | 13007 (HpaII) | | |
| --- | --- | --- | --- | --- | --- | --- | --- | --- | --- |
| CPM | A | B | C | A | B | C | A | B | C |
| Type 1 | 0 | 0 | 0 | 6474 | 2207 | 2 | 911 | 402 | 3 |
| Type 2 | 1 | 30 | 3 | 690 | 235 | 156 | 241 | 124 | 201 |
| Type 3 | 0 | 0 | 3 | 4957 | 799 | 79 | 823 | 84 | 87 |

Samples were further analyzed to determine various properties of eccDNA, such as size, genomic location, and methylation. Such analysis is provided below.

1. Size Profiling

FIGS. 3A-5B show size profiling of one pregnancy case (MspI treated) according to embodiments of the present disclosure. The horizontal axis is the size of a fragment, and the vertical axis is the frequency percentage at a given size. The frequency is measured within a given type and subtype.

Plasma DNA from these cases were treated with Exonuclease V to eliminate linear DNA. The resultant DNA molecules were digested with either MspI or HpaII, followed by library construction and paired-end sequencing. These figures demonstrate the size profiling of eccDNAs using read types 1-A, 1-B, 1-C, 2-A, 2-B and 2-C. For type 3, size determination was not available due to undetected junctions. The size profiles of eccDNA showed obvious clustering at around 200 bp and 340 bp. When zoomed-in to 100-500 bp range (see insets), a clear 10 bp periodicity was also demonstrated.

Figure 3A:
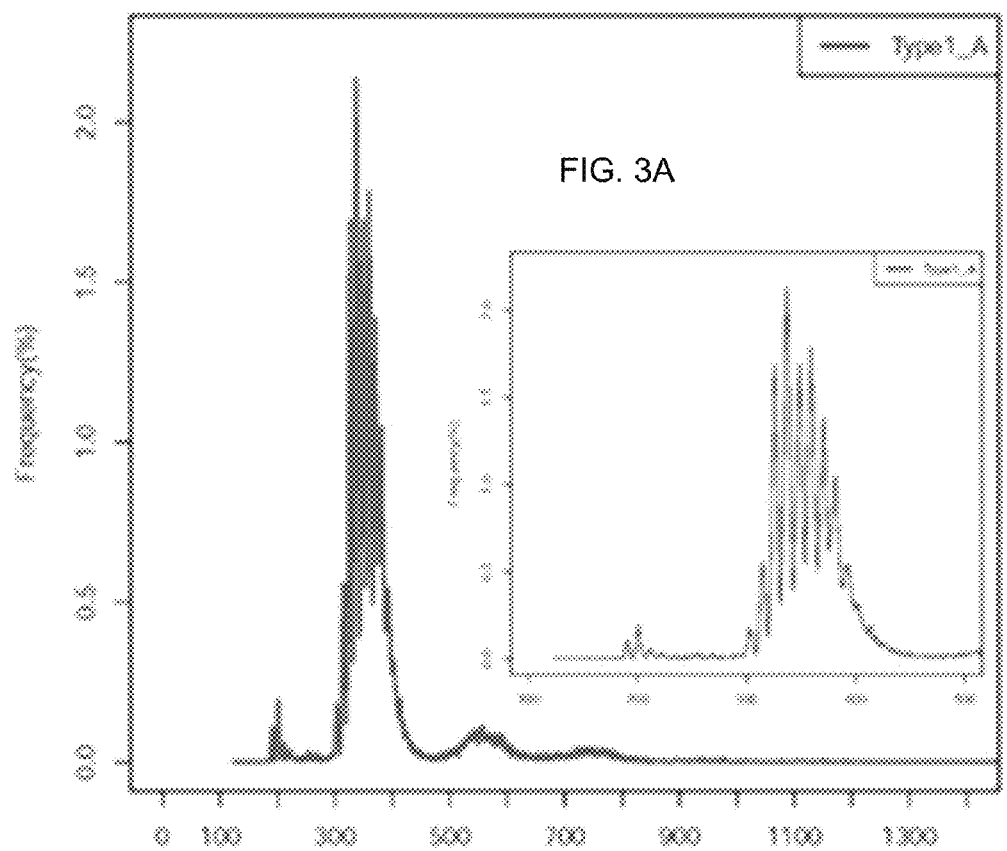
FIGS. 3A-5B show size profiling of one pregnancy case (MspI treated) according to embodiments of the present disclosure.
Figure 3B:
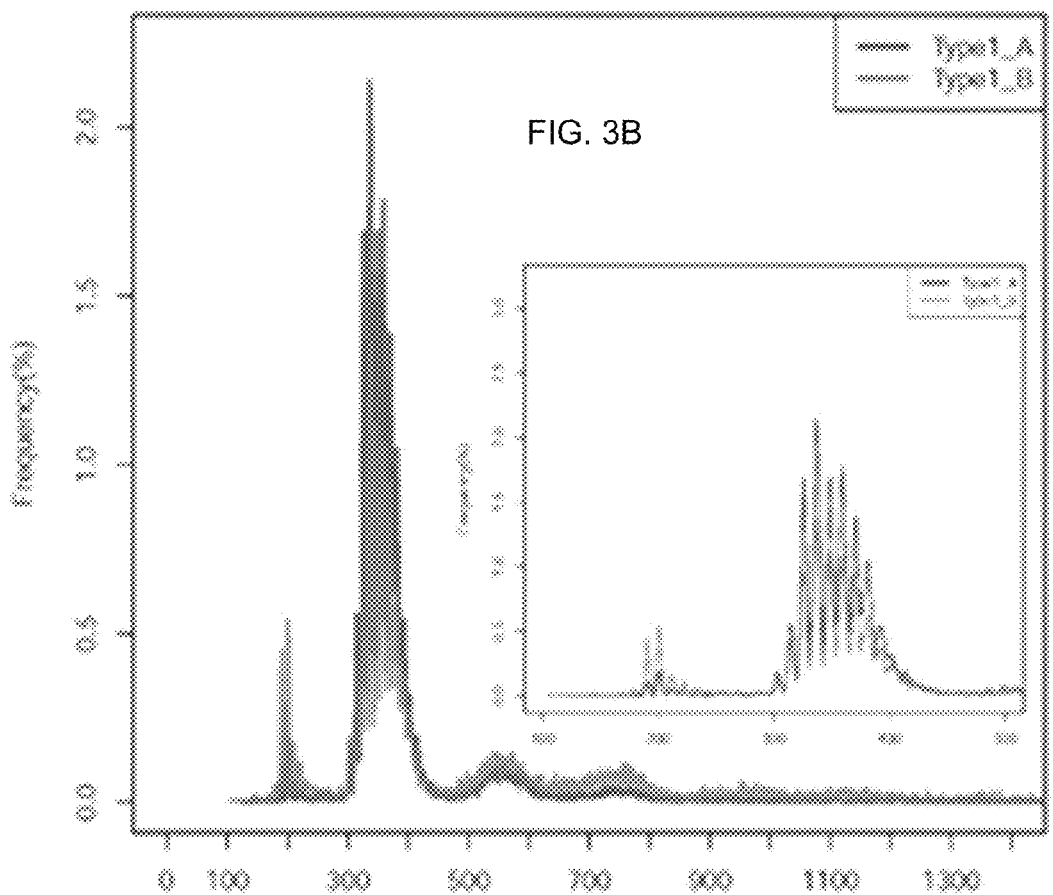

FIG. 3A shows the size profile of type 1-A eccDNA. The inset shows the same plot but zoomed into the 100-500 bp range. Besides the clustering around 200 bp and 340 bp, additional peaks can be seen around 580 bp and 750 bp. The distance between such peaks can relate to nucleosome size. FIG. 3B shows the size profile of type 1-A and 1-B eccDNA. The inset shows the same plot but zoomed into the 100-500 bp range. For 1-B, the peak at 340 bp is shorter, but the other peaks are increased, particularly at 200 bp. The peak around 200 bp can be caused by this length being easy to bend into circular DNA.

Figure 4A:
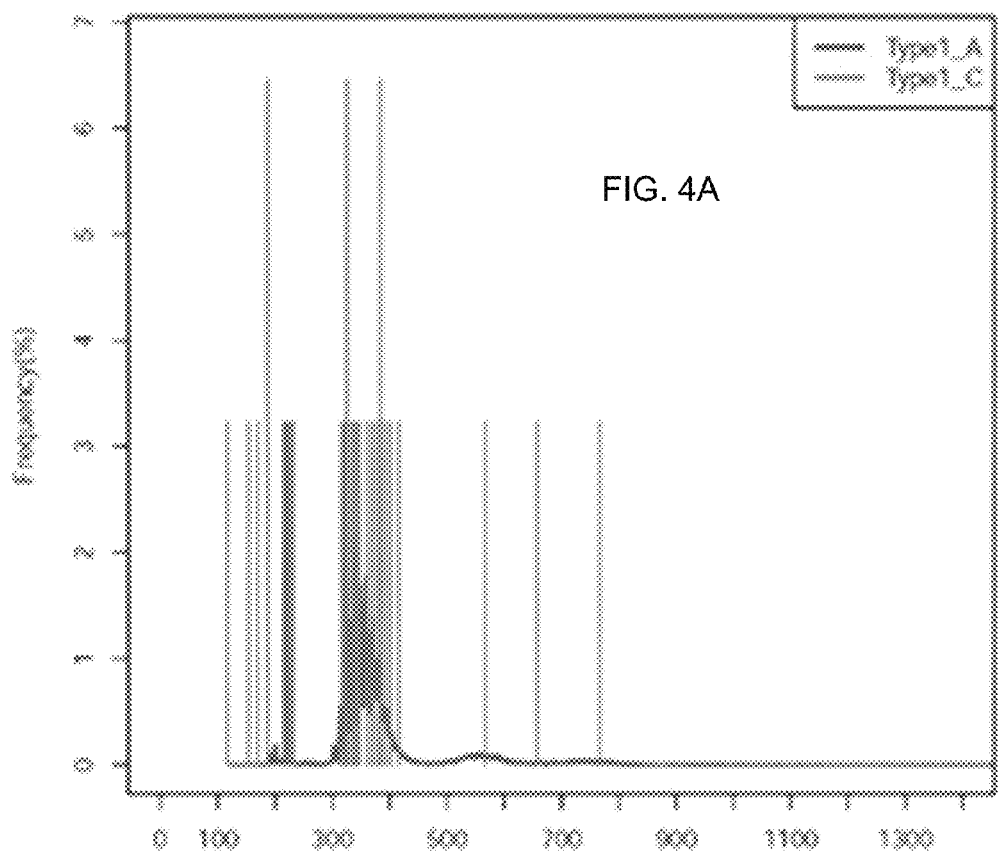
Figure 4B:
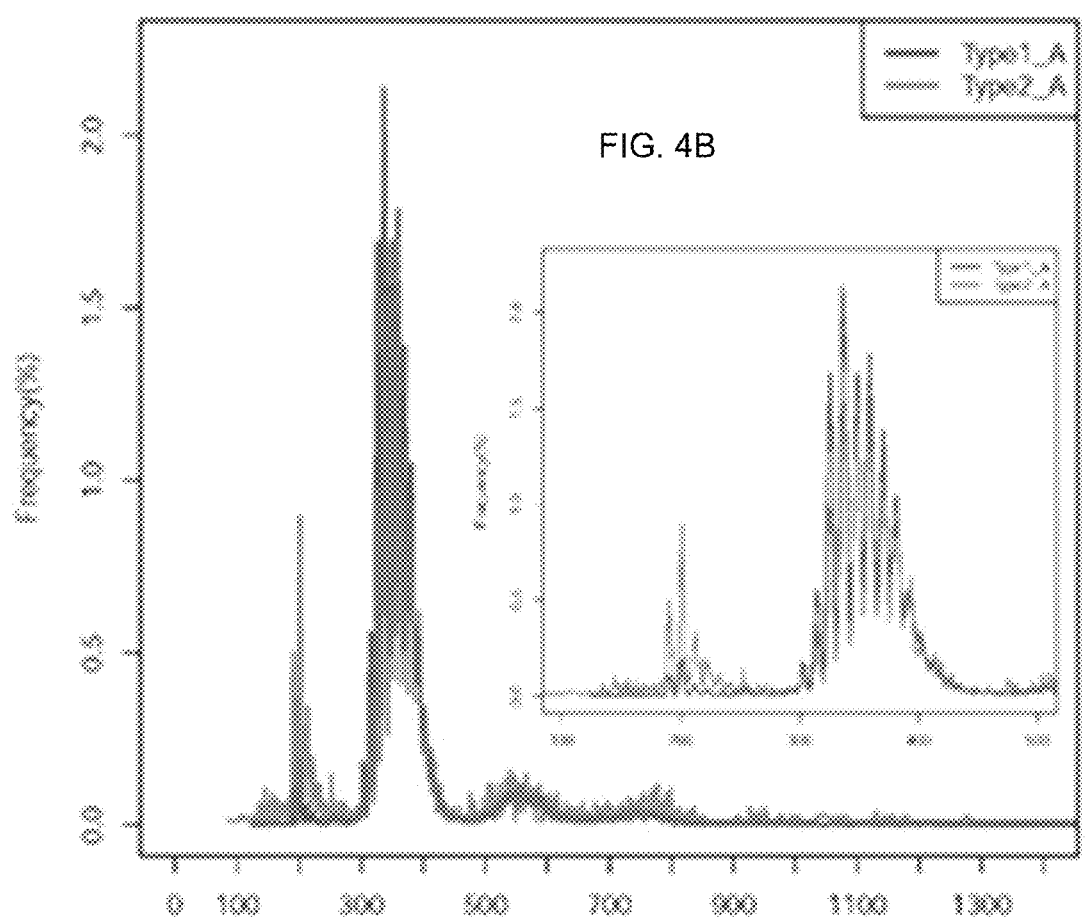

FIG. 4A shows the size profile of type 1-A and 1-C eccDNA. The number of type 1-C eccDNA is much smaller, and thus those plot shows spikes at particular numbers as opposed to a smother statistical distribution. FIG. 4B shows the size profile of type 1-A and 2-A eccDNA. The inset shows the same plot but zoomed into the 100-500 bp range. For 2-A, the peak at 200 bp is significantly increased.

Figure 5A:
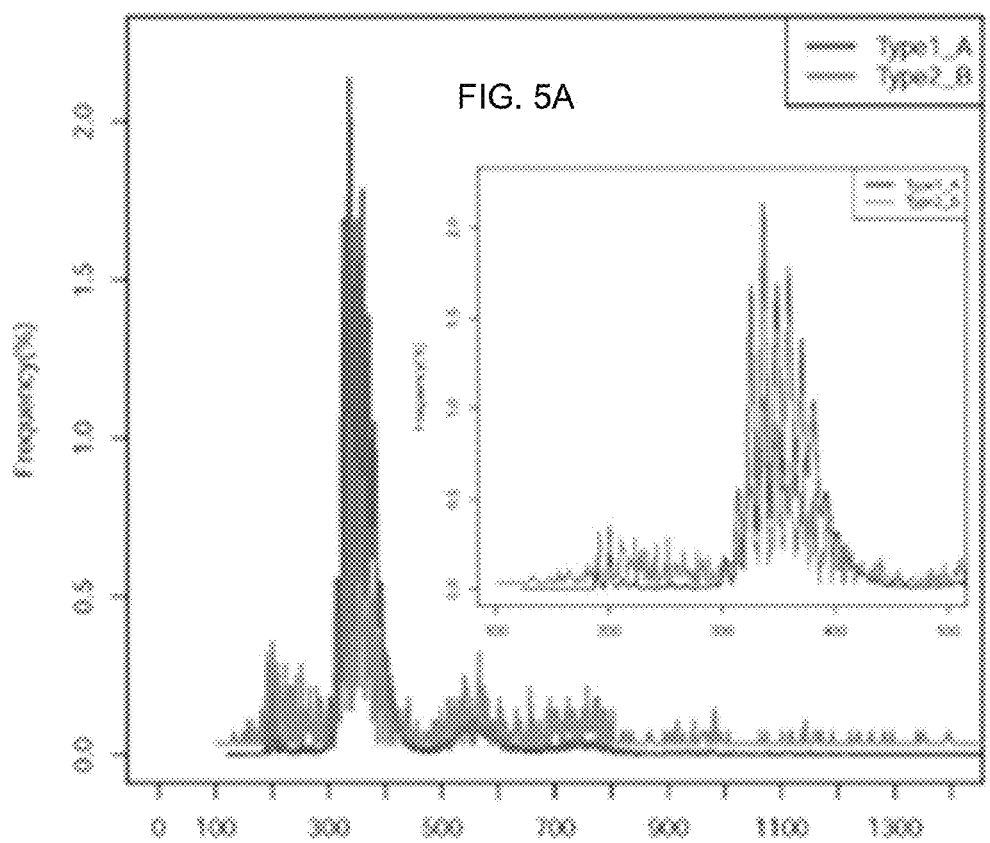
Figure 5B:
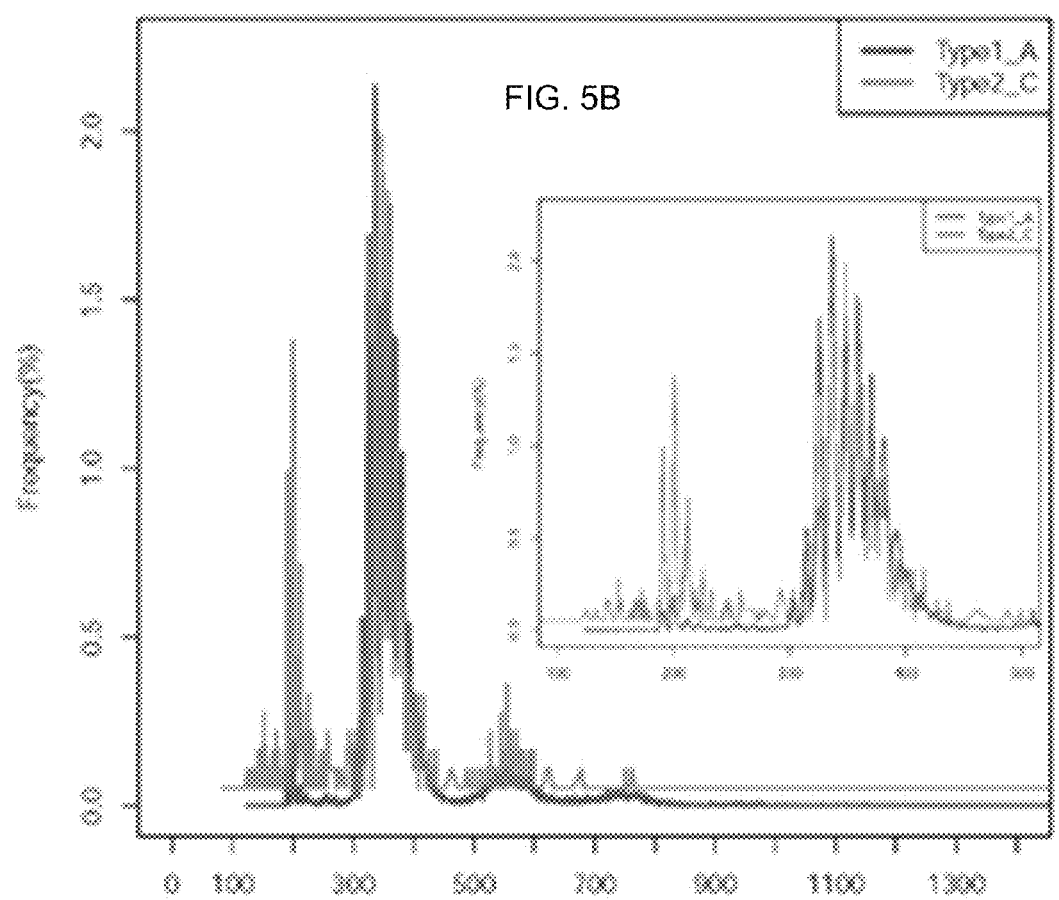

FIG. 5A shows the size profile of type 1-A and 2-B eccDNA. The size profile for 2-B is more spread out compared to 1-A. The spread can be due to sampling variations of the small number of molecules in 2-B. The inset shows the same plot but zoomed into the 100-500 bp range. FIG. 5B shows the size profile of type 1-A and 2-C eccDNA. The inset shows the same plot but zoomed into the 100-500 bp range. For 2-C, the peak at 200 bp is significantly increased.

Figure 6A:
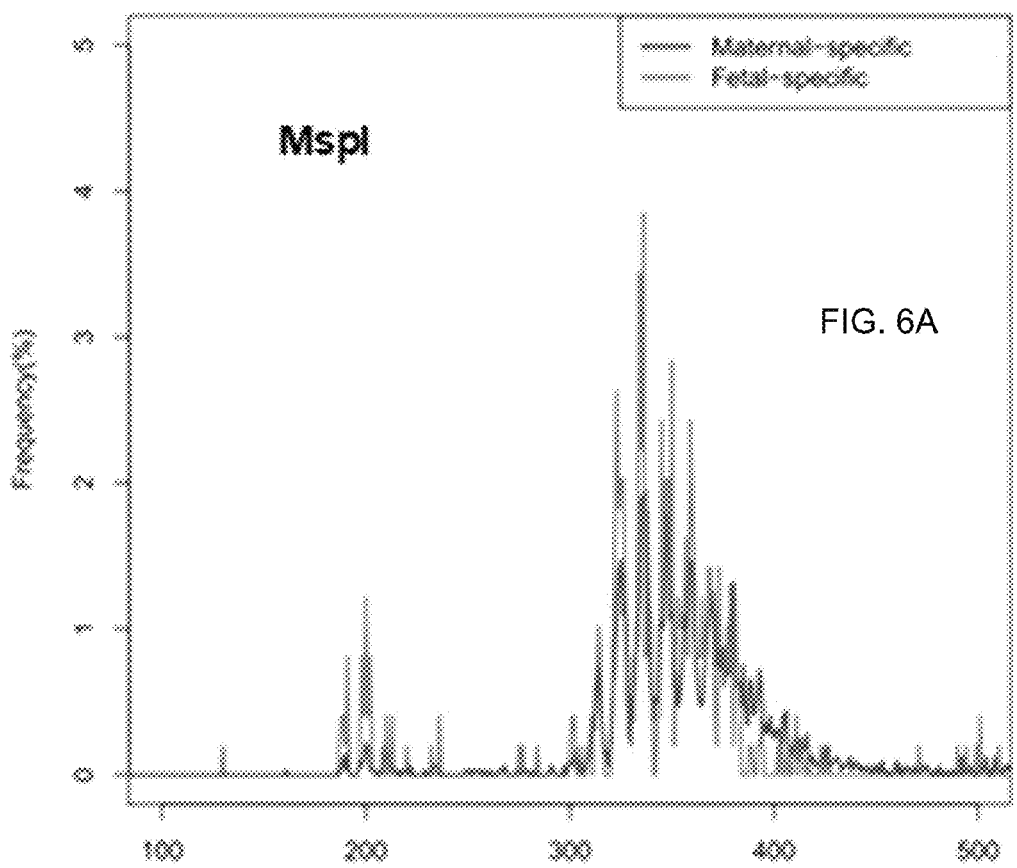
FIGS. 6A-7B show size profiling of maternal- and fetal-specific eccDNAs (5 cases pooled).

FIGS. 6A-7B show size profiling of maternal- and fetal-specific eccDNAs (5 cases pooled) for MspI and HpaII treatments, respectively. The size data is across types 1 and 2. Genotyping of maternal and fetal DNA was accomplished by Illumina iScan technology, which provides information on maternal- and fetal-specific SNPs. In FIGS. 6A and 7A, the frequency graphs of both maternal and fetal eccDNA showed clustering around 200 bp and 340 bp, with fetal eccDNA being more enriched at both peaks.

Figure 6B:
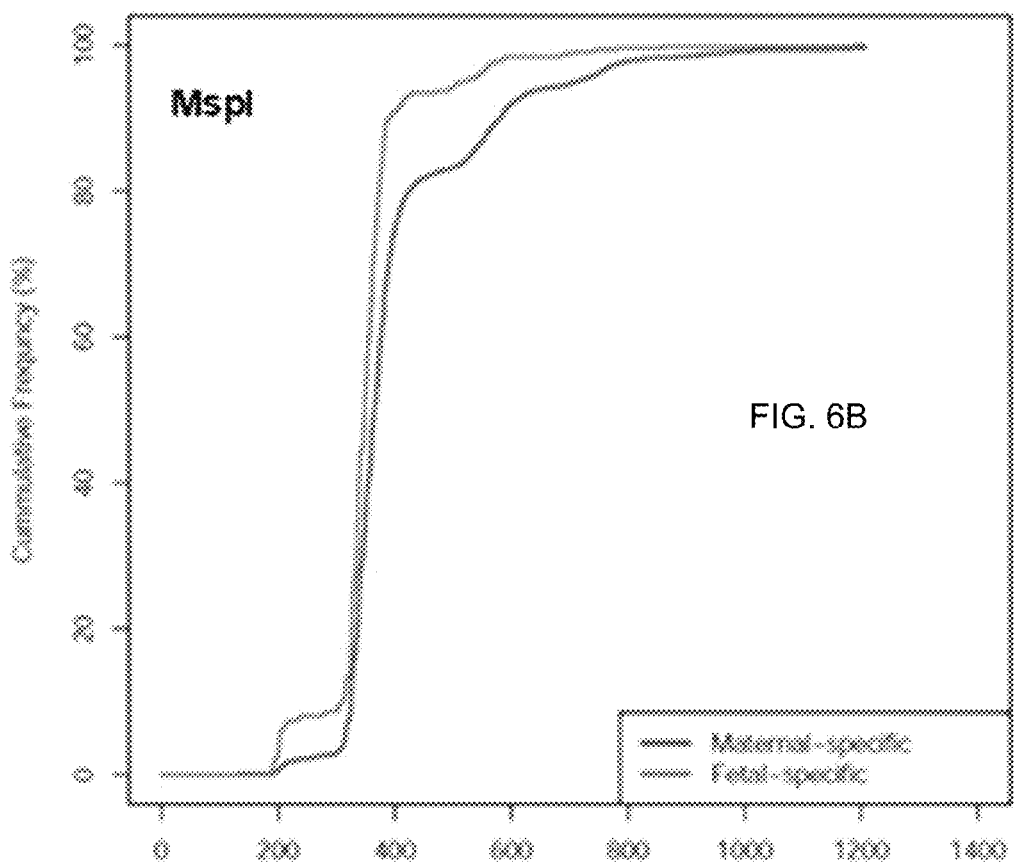
Figure 7A:
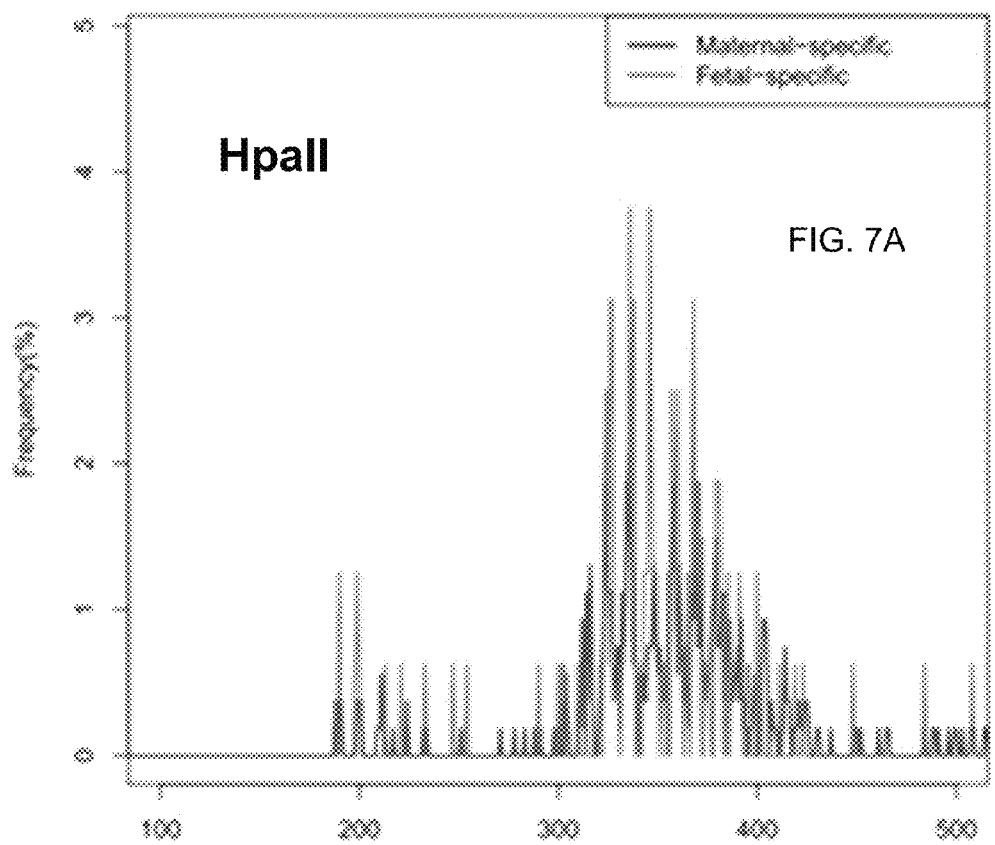
Figure 7B:
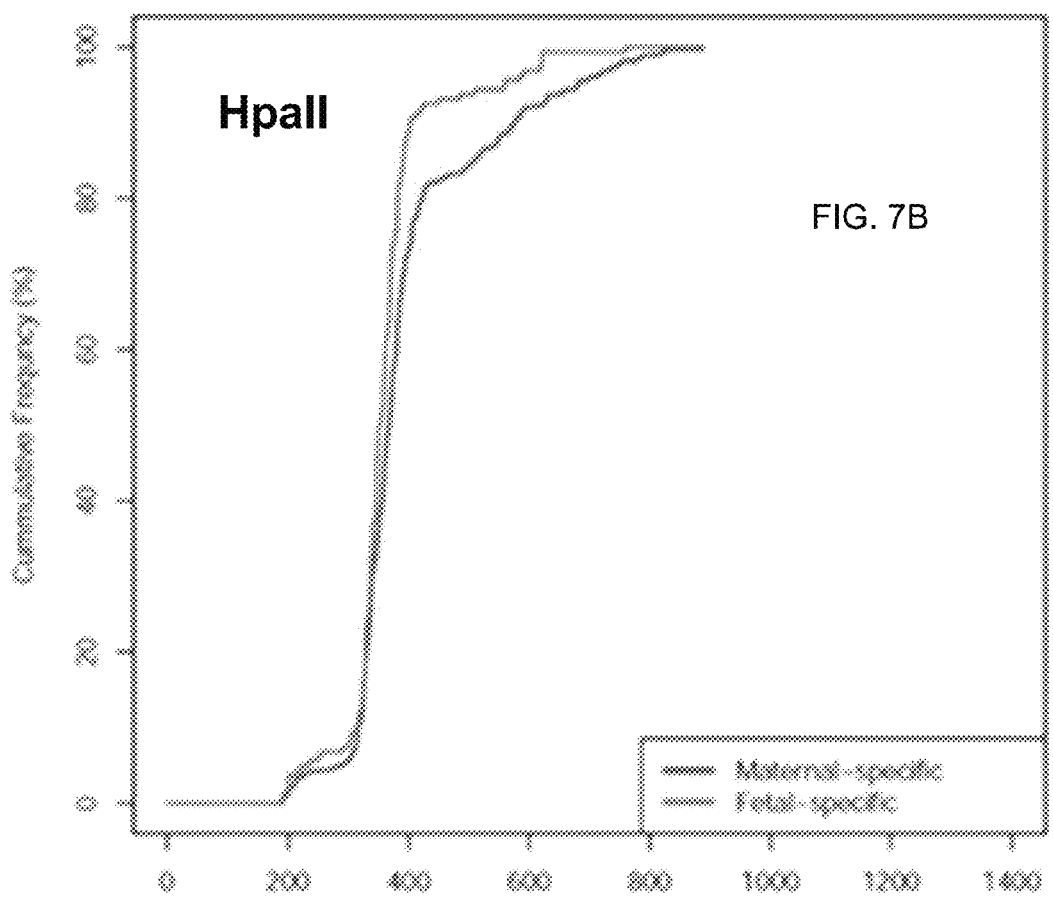

In FIGS. 6B and 7B, the cumulated frequency graphs showed that fetal-specific eccDNA molecules were relative shorter than maternal-specific ones. This phenomenon was observed for both MspI and HpaII treatments. As an example, this difference in the size of fragments can be used to detect sequence imbalances (e.g., amplification and deletions) in a chromosomal region for the fetus or a tumor, e.g., as described in U.S. Patent Publication Nos. 2011/0276277, 2016/0217251, 2013/0040824, 2016/0201142, and 2016/0217251, which are incorporated by reference in their entirety. For example, an amplified region in a fetus or a tumor will increase the release of eccDNA into plasma because of the dosage effect, resulting in more eccDNA with shorter sizes compared with unaffected regions. A deleted region will decrease the release of eccDNA into plasma because of the dosage effect, resulting in less eccDNA with shorter sizes compared with unaffected regions.

The dosage effect can be used directly as well to detect sequence imbalances (e.g., amplification and deletions) in a chromosomal region for the fetus or a tumor, e.g., as described in U.S. Patent Publication Nos. 2009/0087847, 2009/0029377, 2011/0105353, 2013/0040824, 2016/0201142, and 2016/0217251, which are incorporated by reference in their entirety. For cancer, published data for tumor cells suggest that more eccDNA are released from genomic regions with oncogenes due to amplifications. (Verhaak, R. G. W., Bafna, V. & Mischel, P.S. Extrachromosomal oncogene amplification in tumour pathogenesis and evolution. Nat Rev Cancer 19, 283-288 (2019)). Once such cells undergo apoptosis or necrosis, such eccDNA will become cell-free in plasma or other bodily fluids.

2. Genomic Locations of Circular DNA

For the 5 pregnancy cases, the genomic locations of the circular DNA was determined by alignment to a reference genome. The genomic locations were determined for different types of locations.

Figure 8:
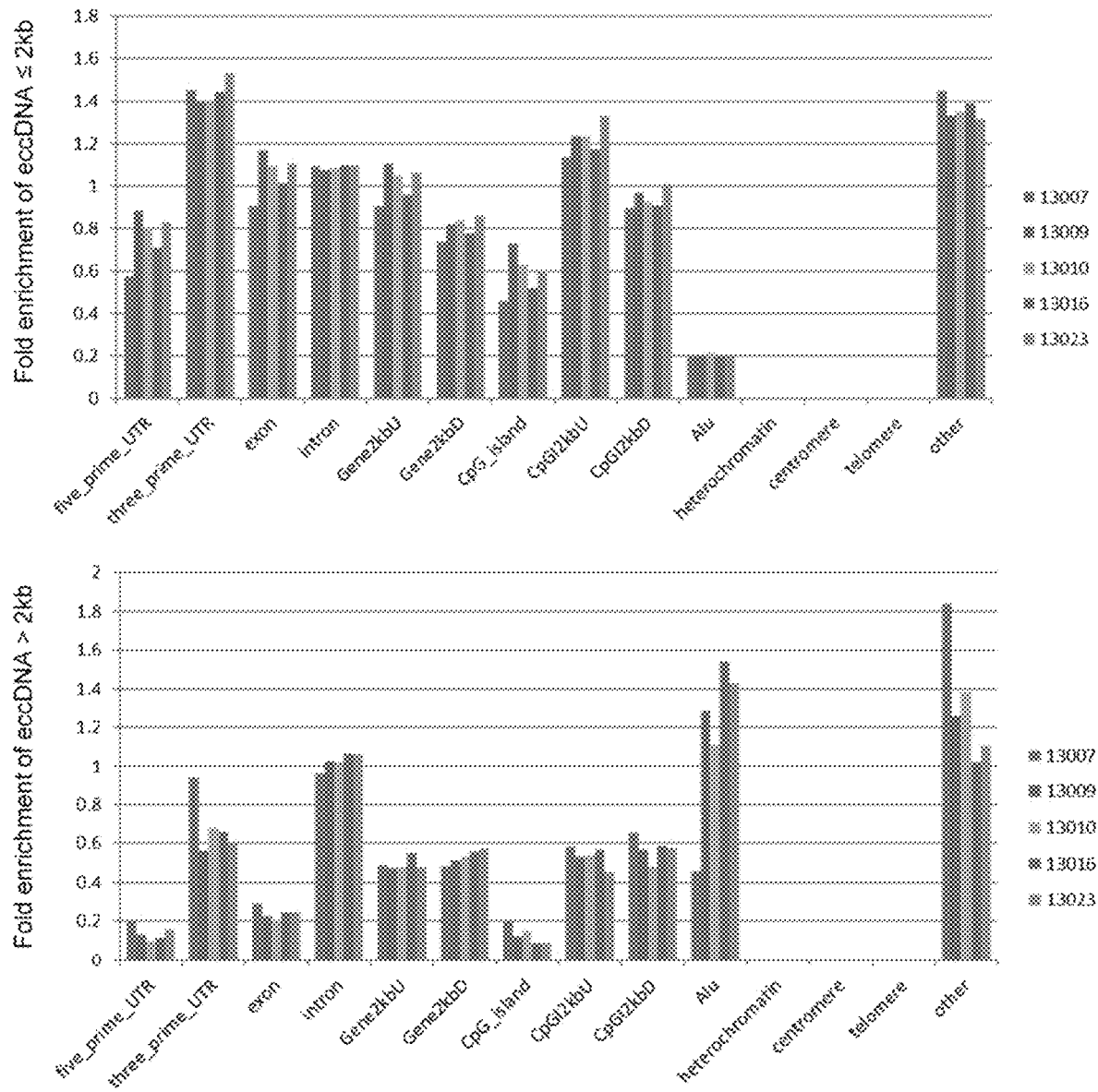
FIG. 8 shows annotation for genomic locations of eccDNA.

FIG. 8 shows annotation for genomic locations of eccDNA. The genomic locations of eccDNA from the 5 pregnancy cases demonstrated similar patterns. The eccDNA molecules of up to 2 kb in size were relatively enriched in 3' untranslated regions (UTR) and CpG islands compared to other regions. The eccDNA molecules longer than 2 kb in size were relatively enriched in Alu regions.

FIG. 9 shows the genomic locations of eccDNA from one pregnancy plasma sample treated with MspI and HpaII. From outside to inside: 1) all eccDNA; 2) eccDNA≤2 kb; 3) eccDNA>2 kb; 4) maternal-specific eccDNA; 5) fetal-specific eccDNA. Red: >95% confidence interval; grey: between confidence interval. The eccDNA treated with MspI and HpaII showed similar distribution patterns. The eccDNA were generated from a broad scale of genomic regions with specific hotspots on different chromosomes. FIG. 9 shows that both MspI and HpaII treatment could detect eccDNA generated from similar regions across the genome. This provides a mutual-validation for the two treatment methods.

As described in the previous section, an amount of eccDNA in a region (e.g., in combination with linear DNA) can be used to identify a copy number aberration. The use of eccDNA (e.g., in a size or count analysis) can increase accuracy, e.g., due to more DNA being analyzed. For cancer, the amount of aberrant regions can be used to detect cancer and the aberrations can be tracked to monitor cancer over time, as described in 2013/0040824.

3. Methylation

Methylation status of linear DNA molecules in human plasma has been leveraged for the detection and diagnosis of various diseases such as cancer (Chan et al. Proc Natl Acad Sci USA. 2013; 110: 18761-18768; Liu et al. Ann Oncol 2018; 29: 1445-1453). Given such biological application values of the methylation information of linear cell-free DNA, the characterization of eccDNA methylation status in human plasma could provide new possibilities for clinical applications. However, there is no published report for the analysis of eccDNA methylation.

As explained above, the restriction enzymes MspI (methylation-insensitive) and HpaII (methylation-sensitive) can provide methylation information. The complementing information provided by the number of eccDNA detected from methylation-insensitive and methylation-sensitive restriction enzymes allows one to deduce the methylation levels of the eccDNA. For example, the methylation levels of eccDNA can be deduced using the numbers of eccDNA detected in MspI- and HpaII-treated samples from the same case. The percentage of methylated CpG sites in the CCGG sequences (M) were deduced by the following formula:

$$M(\%) = \frac{E_M - E_H}{E_M} \times 100\%$$

where $E_M$ stands for the eccDNA counts in MspI-treated samples and $E_H$ the eccDNA counts in HpaII-treated samples.

Table 3 shows methylation levels of eccDNA. eccDNA counts from MspI and HpaII treated plasma DNA samples were used to deduce the methylation levels of those DNA. Data from the five cases demonstrated DNA methylation levels comparable to linear DNA as previously documented (Lun et al. Clin Chem. 2013; 59:1583-94).

TABLE 3

| Case ID | 13007 | | 13009 | | 13010 | | 13016 | | 13023 | |
|---|---|---|---|---|---|---|---|---|---|---|
| Treatment | MspI | HpaII | MspI | HpaII | MspI | HpaII | MspI | HpaII | MspI | HpaII |
| No. of eccDNA (CPM) | 6474 | 911 | 1061 | 356 | 1462 | 328 | 1510 | 316 | 844 | 223 |
| Deduced methylation level | 85.93% | | 66.45% | | 77.56% | | 79.07% | | 72.22% | |

As shown in the next section, the methylation patterns of eccDNA for a particular tissue (e.g., fetal or tumor) can mirror the methylation patterns in linear DNA for the same tissue. Thus, techniques used for linear DNA can also be used for eccDNA. For example, methylation levels of linear DNA and eccDNA can be used to detect cancer by comparing one or more methylation levels to a reference value, e.g., as described in U.S. Patent Publication No. 2014/0080715. As another example, the difference in methylation for fetal DNA can be used to determine an inherited haplotype, e.g., as described in U.S. Patent Publication No. 2017/0029900. As another example, methylation patterns can be used to determine a percentage of eccDNA from a particular tissue type (such as fetal or tumor), e.g., as described in U.S. Patent Publication No. 2016/0017419 and 2017/0349948. These publications are incorporated by reference in their entirety.

4. Fetal Fraction

Chromosomal fetal DNA is generally hypomethylated relative to maternal DNA. This behavior persists for cell-free linear DNA. We analyzed the relation between a fetal DNA fraction determined using linear DNA and using eccDNA for methylation sensitive and insensitive restriction enzymes. The results indicate a hypomethylation for fetal eccDNA relative to maternal eccDNA.

Table 4 shows fetal DNA portion as deduced by linear and eccDNA. As previously documented, fetal linear DNA molecules are relatively hypomethylated when compared to maternal linear DNA in plasma (Tong et al. Clin Chem. 2007; 53:1906-14). In our study, HpaII treated samples in four of the five cases were detected with higher portion of fetal linear DNA, which difference can be explained by the hypomethylated status of fetal DNA. When we analyzed fetal portion using eccDNA, similar results were obtained. Fetal eccDNA portions were detected to be higher in HpaII treated samples than that in the MspI treated samples.

TABLE 4

| Case ID | Treatment | Fetal DNA fraction (linear DNA) | Fetal DNA fraction (eccDNA) |
|---|---|---|---|
| 13007 | untreated | 35.66% | |
| | MspI | 33.70% | 15.77% |
| | HpaII | 35.80% | 23.33% |
| 13009 | untreated | 38.70% | |
| | MspI | 32.69% | 18.35% |
| | HpaII | 35.55% | 22.13% |
| 13010 | untreated | 22.73% | |
| | MspI | 20.36% | 17.97% |
| | HpaII | 25.83% | 24.91% |

TABLE 4-continued

| Case ID | Treatment | Fetal DNA fraction (linear DNA) | Fetal DNA fraction (eccDNA) |
|---|---|---|---|
| 13016 | untreated | 21.73% | |
| | MspI | 20.00% | 7.36% |
| | HpaII | 18.35% | 18.98% |
| 13023 | untreated | 19.68% | |
| | MspI | 18.68% | 7.59% |
| | HpaII | 19.46% | 12.35% |

Accordingly, fetal eccDNA exhibits hypomethylation relative to maternal eccDNA. This difference between tissue types enables analysis techniques developed for cell-free linear DNA to be used for eccDNA.

D. Tagmentation

As mentioned above, after exonuclease treatment to remove linear DNA, a transposase may be used to cut circular DNA. Transposases (e.g. Tn5) can be used to mediate the fragmentation of circular DNA and ligate the synthetic oligonucleotides at both ends to the linearized fragments in a single reaction. The workflow is achieved by taking advantage of the fact that transposases have a 'cut-and-paste' property. Such a 'cut-and-paste' function can cut double-stranded DNA and paste a synthetic oligonucleotide into a target sequence. The complex of Tn5 dimer with synthetic adaptors can enable the adaptor sequences to be end-jointed to the 5'-end of the target DNA by the transposase 'cut-and-paste' catalytic activity (Adey et al. Genome Biol. 2010; 11:R119). The targeted DNA ligated with adaptors can facilitate the incorporation of full sequencing adaptors for a particular sequencing platform, for example, but not limited to, the Illumina sequencing-by-synthesis platform, the Pacific Biosciences Single Molecule, Real-Time (SMRT) system, nanopore sequencing, and semiconductor sequencing (e.g. Ion Proton and the GenapSys Gene Electronic Nano-Integrated Ultra-Sensitive (GENIUS)), etc. The Tn5-mediated fragmentation of double-stranded DNA is believed to be generally random. Therefore, such Tn5-mediated fragmentation would make it possible to sequence circular DNA molecules. The way that transposase catalyzes in vitro DNA fragmentation and adaptor incorporation simultaneously can improve the efficiency for sequencing library construction.

1. Overview

Figures 10A, 10B:
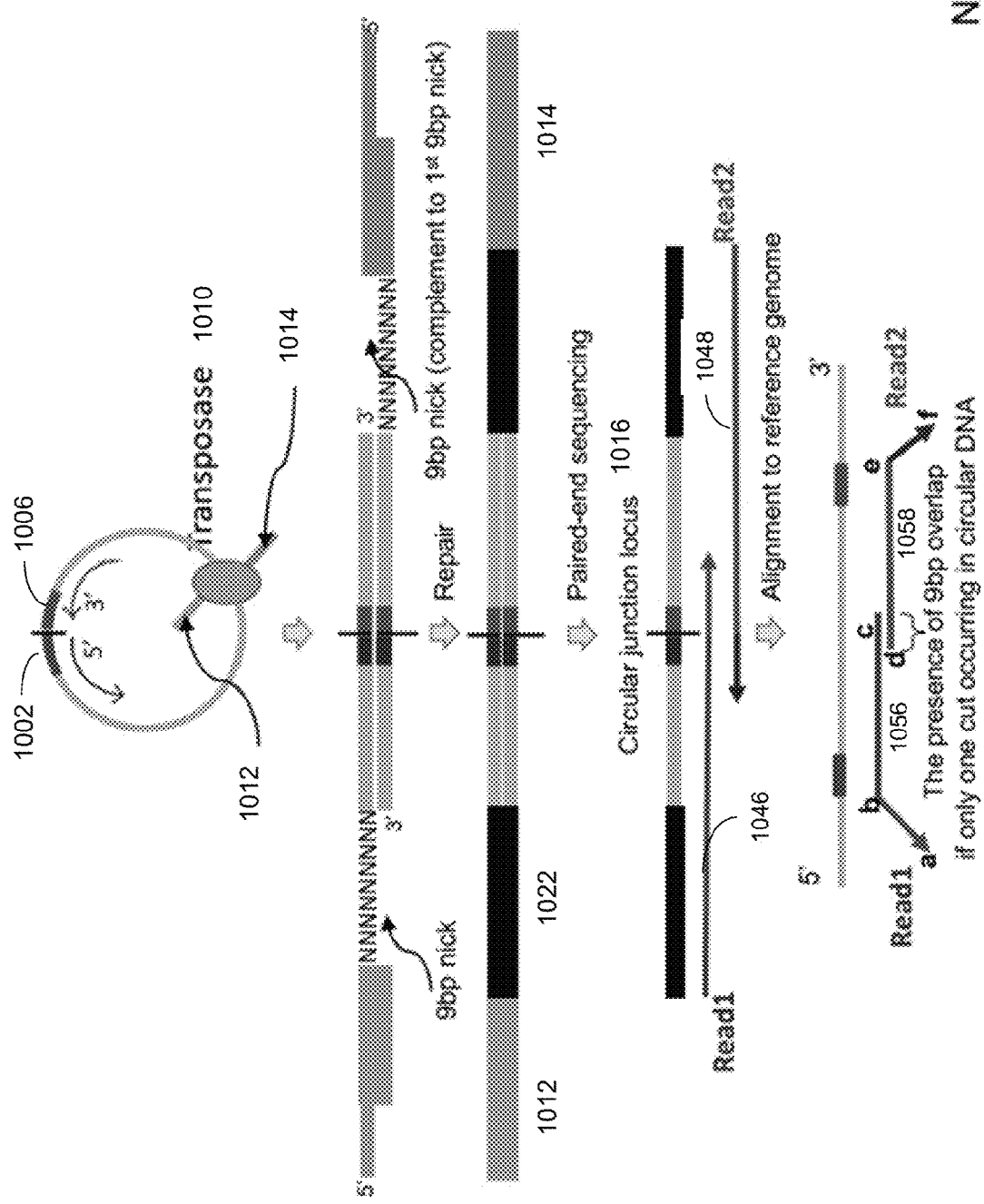
FIGS. 10A and 10B show an example of the principle for eccDNA identification with the use of transposase based tagmentation according to embodiments of the present disclosure.

FIG. 10A shows an example of the principle for eccDNA identification with the use of transposase based tagmentation according to embodiments of the present disclosure. As shown in FIG. 10A, we developed a protocol to analyze extracellular circular DNA with the use of transposases. The "blue" bar 1002 and the "red" bar 1006 in the genome indicate two regions that are assumed to be joint together to form a piece of extrachromosomal circular DNA (eccDNA). The "yellow oval" indicated a transposase dimer 1010. The "green" bar 1012 and the "cyan" bar 1014 linked to the transposase dimer represent synthetic oligonucleotides (adapter sequences) that facilitate the sequencing. For example, such synthetic oligonucleotides could be hybridized by Illumina sequencing adaptors (e.g., the P7 and P5 adaptors). Tn5 can initiate non-specific cleavages on plasma DNA molecules including linear and circular DNA and ligate the synthetic oligonucleotides to both ends of cleaved fragments. Such Tn5 cleavage can introduce a 9 bp nick nearby the cleavage site. Such nicks and single strand probes on adaptors can filled to form double-stranded DNA before sequencing.

The sequencing and alignment can then be performed as described for FIG. 1. As shown in FIG. 10A, the 9 bp nick can result in the presence of 9 bp overlap if only one cut occurred. If more than one cut occurred, there might be no overlap as the sequence at the two cuts can be different.

Because the majority of spontaneously occurring linear DNA molecules in plasma would be around 166 bp, we could adjust the concentration of Tn5 and treatment duration to create reaction conditions whereby most of the spontaneously occurring linear plasma DNA would be cut only once. As shown in FIG. 10B, we would not be able to sequence (using paired-end sequencing) the cleaved fragments originating from a linear DNA that is cut once. In contrast, if the cleaved fragments originate from a piece of circular DNA, then they would be sequenceable because both ends of linearized fragments would be linked to synthetic adaptors for sequencing. This strategy allows skipping a step of removal of linear DNA (e.g., exonuclease is not needed) or a step of enriching circular DNA. The use of Tn5, or similar enzymes, has the advantage over the use of restriction enzymes with specific recognition sites because the former would make it possible to sequence potentially any circular DNA and not require specific sequence motifs for cutting.

Subsequently, the blunt-end DNA could be sequenced using different sequencing technologies including, but not limited to, the Illumina platform, Ion Torrent sequencing, etc. In one embodiment, if we sequenced read1 and read2 with a sufficient read length, we would have a chance to have sequence reads across the junction (indicated by the chimeric arrows) in the step of paired-end sequencing. Therefore, in the alignment results, we would observe read1 and read2 sequences of linearized molecules mapping to a reference genome in unique mapping directionalities as shown in FIG. 10A, as was described for FIG. 1. For illustration purpose, we define an unmapped segment (red arrow after the alignment step, "b→a" segment) in read1, which corresponds to the sequence across the junction derived from the other genomic region being joint to form a circular DNA. Similarly, we define an unmapped segment (blue arrow after the alignment step, "e→f" segment) in read2, which corresponds to the sequence across the junction derived from the other genomic region being joint to form a circular DNA molecule. Such unique mapping directionalities can include the below two scenarios:

(a) Read1 would be aligned in a reversed strand and read2 would be aligned in a forward strand when read1 smallest mapping coordinate of segment "b→c" (i.e. b) is equal to or smaller than read2 smallest mapping coordinate of segment "d→e" (i.e. d).

(b) Read1 would be aligned in a forward strand and read2 would be aligned in a reversed strand when read2 smallest mapping coordinate is equal to or smaller than read1 smallest mapping coordinate (not shown in the schematic).

Such unique mapping directionalities were different from conventional mapping directions for a pair of paired-end reads originating from an initially linear DNA. For example, read1 is fully aligned in a forward strand and read2 is fully aligned in a reversed strand when read1 smallest mapping coordinate is equal to or smaller than read2 smallest mapping coordinates; or read1 is fully aligned in a reversed strand and read2 is fully aligned in a forward strand when read2 smallest mapping coordinates are equal to or smaller than read1 smallest mapping coordinates. Bioinformatically, searching the mapping sites in the reference genome of the unmapped segments (e.g. "b→a" and "e→f") present in read1 and/or read2 would allow for delineating the junctions. The distance between junction sites deduced from the unmapped segments from a fragment would indicate the size of a circular DNA.

Another feature would be that there may be possible to observe ~9 nucleotides overlapped between the mapped read1 and read2 if a circular DNA is cut only once. Such 9 bp overlapped sequence between read1 and read2 was introduced by the staggered ends created by Tn5. Tn5 would make two staggered single-stranded breaks and the distance between two breaks would be 9 bp ("N" letters in FIG. 10A). Each break would be joined with read1 and read2 adaptors, respectively. After repairing, the 9 bp gaps would be filled in by the DNA polymerase, which would generate a repeat sequence in read1 and read2 ("black" bar 1022 in FIG. 10A). Taken together, in this eccDNA identification approach based on tagmentation, there are four "diagnostic features", including:

i. Circular DNA specific mapping directions (directionality);
ii. Junction-aware reads;
iii. cutting tags corresponding to the adapter sequences;
iv. Nine overlapped bases in 5' ends of read1 and read2 sequences when a circular DNA is cut only once.

In other embodiments, if we use a sequencing platform that can generate long reads, e.g., Pacific Biosciences SMRT sequencing, nanopore sequencing, etc., then we can potentially see junctional information from just one read.

Sequencing reads fulfilling at least one of diagnostic features can be defined as a candidate circular DNA. For a circular DNA cutting multiple times by Tn5, read1 and read2 would not bear repeated sequences (overlapped bases) between each other. In some instances, only one read from a pair might cross the junction site while the other would not carry the junction. Even if both reads from a pair do not carry a junction, unique mapping directions would imply a circular DNA.

With the use of transposase-based tagmentation, the bioinformatics approach for detecting the eccDNA could model after that used in the restriction enzyme-based method. For example, we could skip the steps that involve the analysis of the presence of cutting motifs introduced by a restriction enzyme. The mapping directionality and the presence of junction in a read would be two main "diagnostic features" for determining whether a particular fragment could be classified as circular DNA.

2. Plasma Results

Table 5 shows eccDNA detection by tagmentation approach. CPM corresponds to circular DNA per million mapped reads. Plasma samples from $3^{rd}$ trimester pregnancies were treated with Exonuclease V, followed by tagmentation and library preparation using Illumina XT DNA library Preparation Kit. Sequencing results showed that high numbers of eccDNA were detected using this method. Also, the amounts of eccDNA detected by this approach were much higher than that of the restriction enzyme treatment approach.

TABLE 5

| Treatment duration | Raw fragments | Properly mapped reads | Mappability (%) | Putative eccDNA (CPM) | Putative eccDNA with detected junctions (CPM) |
|---|---|---|---|---|---|
| 1 min | 3,335,865 | 1,583,086 | 47.46 | 26,107.43 | 9626 |
| 2 min | 3,537,736 | 1,710,527 | 48.35 | 27,148.17 | 8726 |
| 3 min | 3,695,279 | 1,787,577 | 48.37 | 30,270.02 | 8021 |
| 4 min | 3,264,694 | 1,609,613 | 49.3 | 29,004.36 | 7950 |
| 5 min | 3,171,903 | 1,544,666 | 48.7 | 26,814.14 | 8964 |

Figure 11:
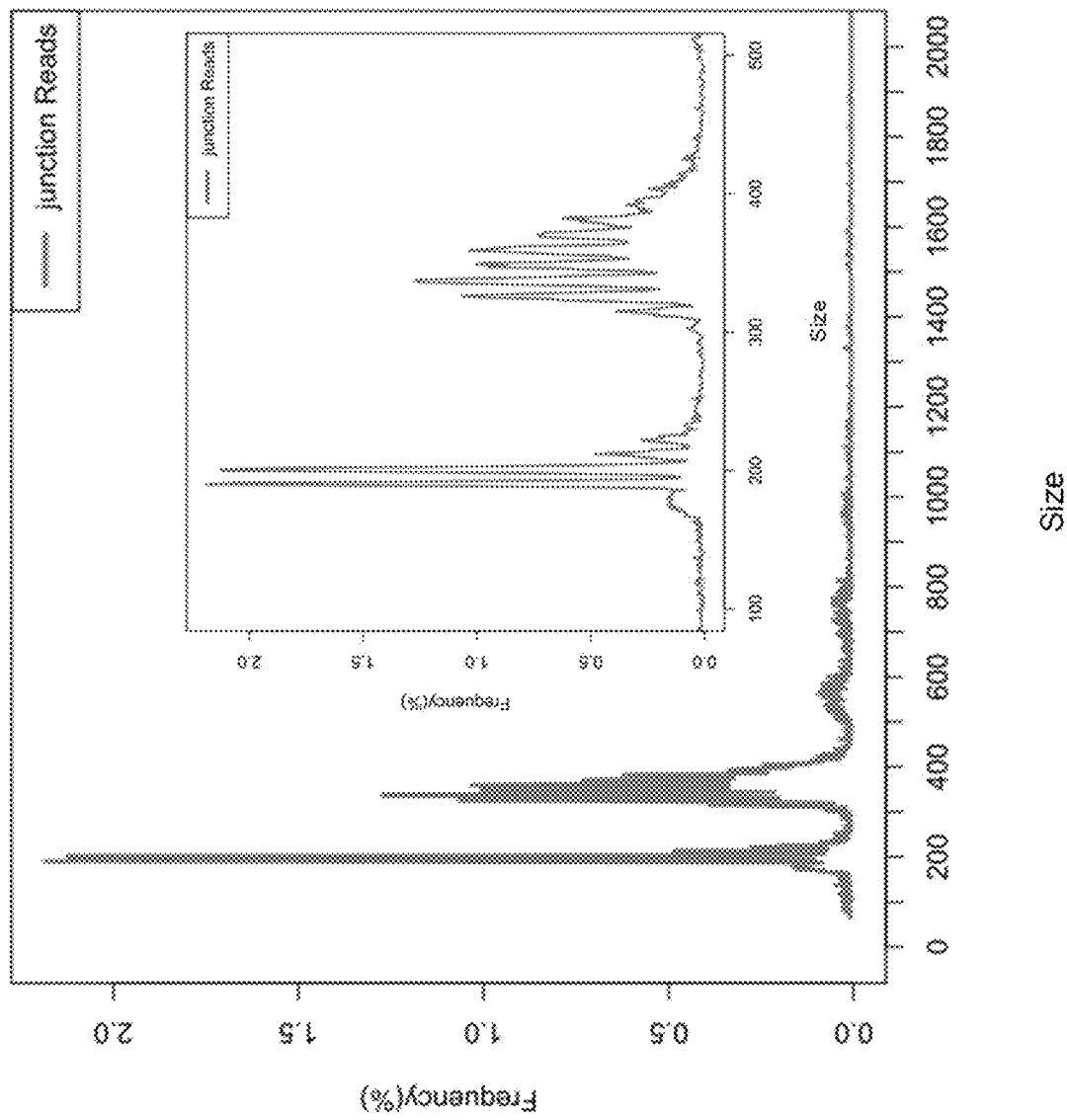
FIG. 11 shows size profiling of eccDNA using a tagmentation protocol according to embodiments of the present disclosure.

FIG. 11 shows size profiling of eccDNA using tagmentation protocol according to embodiments of the present disclosure. The sizes of plasma eccDNA detected using tagmentation protocol showed a clear clustering at around 200 bp and 340 bp. When zoomed-in to the range of 100 bp to 500 bp, a sharp 10 bp periodicity was also demonstrated. The size profile in FIG. 11 resembles the size profiles for techniques using restriction enzymes. Thus, tagmentation can used in a same manner as the restriction enzyme techniques for analyzing various properties of eccDNA, along with diagnostic applications.

3. Cellular Results

Additionally, the Tn5 transposase has been used to develop an assay for transposase-accessible chromatin using sequencing (ATAC-seq) (Buenrostro et al. Nat Methods. 2013; 10:1213-8). Such a method is based on direct in vitro transposition of sequencing adaptors into native chromatin. Chromatin compaction states would affect the efficiency of inserting the sequencing adaptors into the chromatin. Thus, the resulting sequencing coverage would reflect chromatin accessibility. Because ATAC-seq involves the use of the Tn5 transposase, we predict that the sequences originating from circular DNA species (e.g. eccDNA and mitochondrial DNA) in the samples that have been subjected to ATAC-seq would be sequenced and present in ATAC-seq sequencing dataset. There are a number of publicly-available ATAC-seq datasets in ENCODE (encyclopedia of DNA elements, www.encodeproject.org/), including data from a variety of tissues. We downloaded ATAC-seq FASTQ files of 9 tissues from the ENCODE database, including the sigmoid colon, transverse colon, breast epithelium, gastroesophageal sphincter, stomach, omental fat pad, spleen, subcutaneous adipose tissue and tibial artery. All samples were analyzed using non-strand-specific ATAC-seq on an Illumina HiSeq 4000 platform. Such experimental data passed the stringent quality metrics established by the ENCODE consortium (median: 92.6 million reads; range: 76.8-103 million reads).

We used the Tn5-based bioinformatics pipeline developed in this disclosure to analyze ATAC-seq sequencing results. Table 6 shows the number of eccDNA molecules identified across different tissues. Some organs such as the spleen were found to be relatively abundant in eccDNA molecules. These results demonstrate a degree of variation of eccDNA across different organs or tissues. We predict that one could use such a variation for tissue typing and for detection or monitoring of diseases. Because ATAC-seq could be performed at a single cell level (Chen et al. Nat Commun. 2018; 9:5345), the analysis of eccDNA could be achieved at the level of a single cell using the approaches invented in this disclosure.

TABLE 6

EccDNA identified across different tissues using ATAC-seq datasets.

| Tissues | eccDNA detected in ATAC-seq datasets | Normalized eccDNA abundance (CPM) |
|---|---|---|
| Breast epithelium | 782 | 12.96 |
| Gastroesophageal sphincter | 978 | 13.77 |
| Omental fat pad | 763 | 12.19 |
| Sigmoid colon | 978 | 13.51 |
| Spleen | 2913 | 54.00 |
| Stomach | 1648 | 25.03 |
| Subcutaneous adipose tissue | 1080 | 14.33 |
| Tibial artery | 847 | 12.55 |
| Transverse colon | 793 | 11.04 |

CPM is Circular DNA Per Million mapped reads.

For tissue typing of one or more cells, the DNA from the one or more cells can be analyzed using the techniques described above to count the number of eccDNA molecules. Depending on the count per cell, one or more tissue types can be identified. For example, a measurement of 2,900 eccDNA per cell can indicate the tissue type is spleen. Whereas, a measurement of 787 eccDNA per cell can indicate the tissue type is either breast epithelium or transverse colon.

If the tissue type is already known for one or more cells, a significant deviation in the measurement count of eccDNA per cell from a normal reference value (e.g., as provided above) can indicate a disorder. Such a cutoff between disorder and healthy can be determined from measuring a statistical distribution of measured eccDNA per cell for healthy cells and a statistical distribution of measured eccDNA per cell for diseased cells, which may have different diseases. Such a detection method can detect whether a cell is healthy based on the measurement of the number of eccDNA molecules in the cell. For example, cancerous cells would have more eccDNA molecules.

4. Methylation Analysis Using Tagmentation

We further describe new methods that could achieve both the identification and methylation analysis of eccDNA in one go. As explained above, efficient eccDNA identification can be achieved by coupling exonuclease V (exo V) digestion with either restriction enzyme or Tn5 transposase treatments. To bring such methods one step ahead to identification and methylation analysis of eccDNA at the same time, we combined the use of exo V and Tn5, followed by enzymatic conversion of unmethylated cytosine to uracil.

In this embodiment, plasma DNA was first extracted from human plasma. 50 ng of DNA was then treated with exo V to largely eliminate the linear forms of plasma DNA in the samples. The remaining DNA was then incubated with modified Tn5 transposomes constructed in-house [all cytosine bases on the adaptor sequences were substituted by methylated cytosine (5-mC) to protect the adaptors from downstream cytosine to uracil conversion]. Upon 5-mC-Tn5 treatment, the circular DNA molecules were cut open with adaptors attached to the fragment ends. Enzymatic conversion and PCR amplifications would convert unmethylated cytosine (C) bases to thymine (T) bases, which was followed by Illumina sequencing. Bioinformatic pipelines were developed to identify eccDNA molecules and to obtain information of their sequences, size profiles and methylation status.

Figure 12:
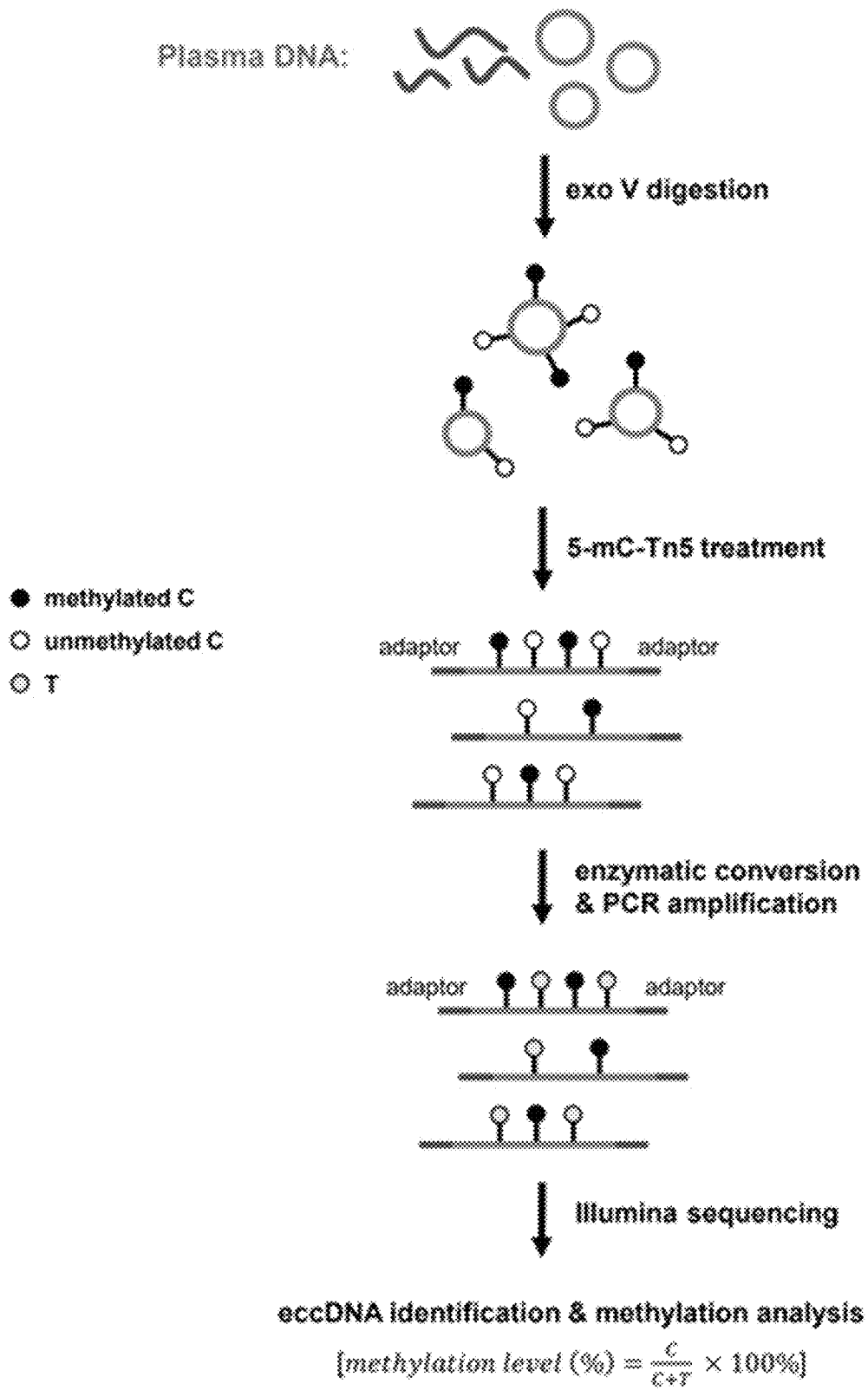
FIG. 12 shows an example workflow of the identification and methylation analysis of eccDNA by enzymatic conversion according to embodiments of the present disclosure.

FIG. 12 shows an example workflow of the identification and methylation analysis of eccDNA by enzymatic conversion according to embodiments of the present disclosure. Plasma DNA is extracted and then incubated with exo V to over-digest the linear DNA in the sample. The remaining DNA was then treated with 5-mC-Tn5 to open up the circles and to ligate the sequencing adaptors (all C were substituted with 5-mC) to the fragment ends. Enzymatic conversion and library construction were then performed using NEBNext Enzymatic Methy-seq Kit from New England Biolabs. Bioinformatic pipelines were developed for the identification, size profiling and methylation analysis of eccDNA molecules from the sequencing results.

To demonstrate that this method could efficiently capture eccDNA, we also performed a parallel test with plasma DNA samples treated with 5-mC-Tn5 only (no exo V treatment). Our results showed that the eccDNA molecules identified in the unit of eccDNA per million mappable reads (EPM) were 40,599 for the exoV+Tn5 sample and 12,807 for the Tn5 only sample. These data demonstrated that the 5-mC-Tn5 transposomes we generated could efficiently linearize the eccDNA molecules for downstream sequencing analyses and that exo V treatment could significantly increase the amount of eccDNA being captured. In other embodiments, alternative measures of eccDNA linearization could also be applied, such as restriction enzyme treatments.

To further demonstrate that this technique could be applied to eccDNA methylation analysis, we compared the methylation levels between small (≤450 bp) and large (>450 bp) eccDNA molecules. The cut-off of 450 bp was applied due to the majority of eccDNA molecules we identified being smaller than 450 bp according to our size profiling data shown in FIGS. 13A-13B.

Figure 13B:
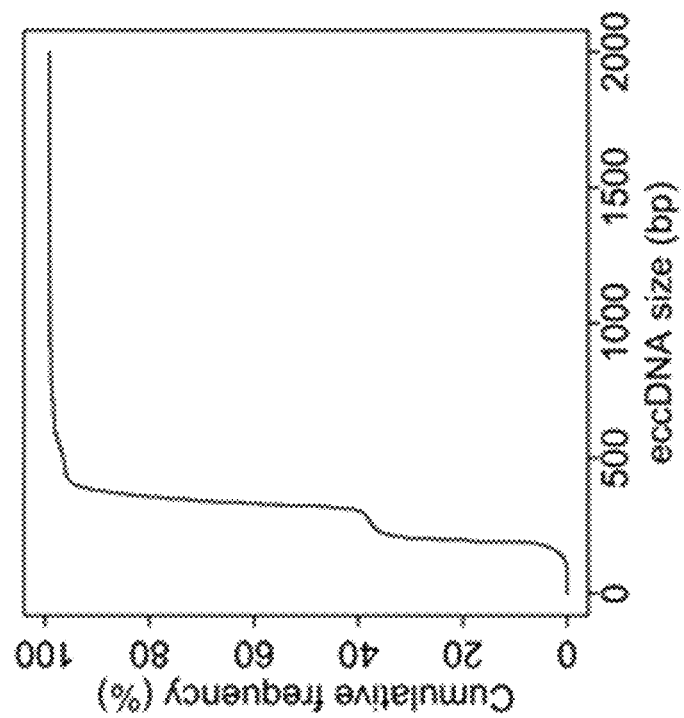
FIGS. 13A and 13B show size profiling and cumulative frequency of eccDNA in human plasma according to embodiments of the present disclosure.
Figure 13A:
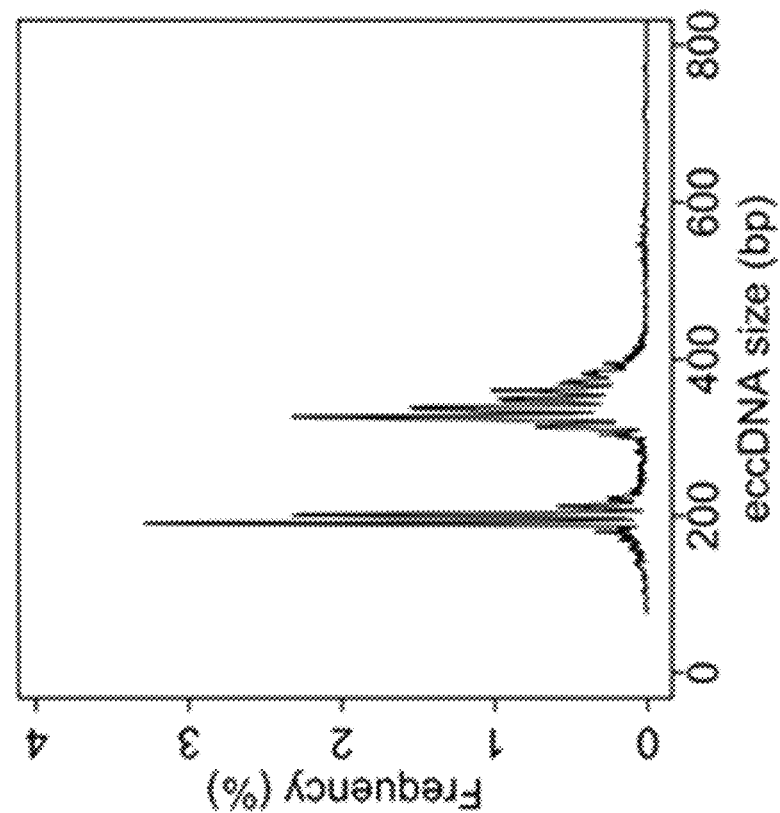

FIGS. 13A-13B show size profiling and cumulative frequency of eccDNA in human plasma according to embodiments of the present disclosure. From the sequencing data, we identified eccDNA molecules and obtained their size information. The sizes of eccDNA peaked at around 202 bp and 338 bp with a sharp 10-bp periodicity, similar to other size profiles herein. The majority of eccDNA molecules were smaller than 450 bp.

In the process of calculating the methylation levels of eccDNA, we have applied the following formula to adjust the results according to the C to T conversion rate in the control genome of lambda DNA:

$$M_{adj}(\%) = \frac{M - (1 - \alpha)}{\alpha} \times 100\%$$

Where $M_{adj}$ is the methylation level post-adjustment; M is the methylation level pre-adjustment and calculated as $$M = \frac{C}{C+T};$$

α is the conversion rate in the spiked-in control genome of lambda DNA.

The methylation level of lambda DNA is an internal control. While processing genomic DNA, we added a small amount of lambda DNA to the sample. These added DNA would proceed with the same experimental flow as the genomic DNA. The reason for using lambda DNA as internal control is that the lambda genome is theoretically entirely unmethylated. If we see that there are residual level of C in lambda DNA that were not converted to T, it means the conversion for lambda DNA, and genomic DNA for that matter, is incomplete. The incomplete conversion of unmethylated C to T in genomic DNA would cause over-estimation of methylation levels. The above formula can be used to adjust this over-estimated methylation level by taking the conversion rate of lambda DNA into account.

The methylation level of small eccDNA molecules (65.2%) was relatively higher than that of the large ones (61.7%). Our data also showed that the remnant linear DNA in this sample exhibited higher methylation level (68.2%) than eccDNA molecules (65%).

Figure 14:
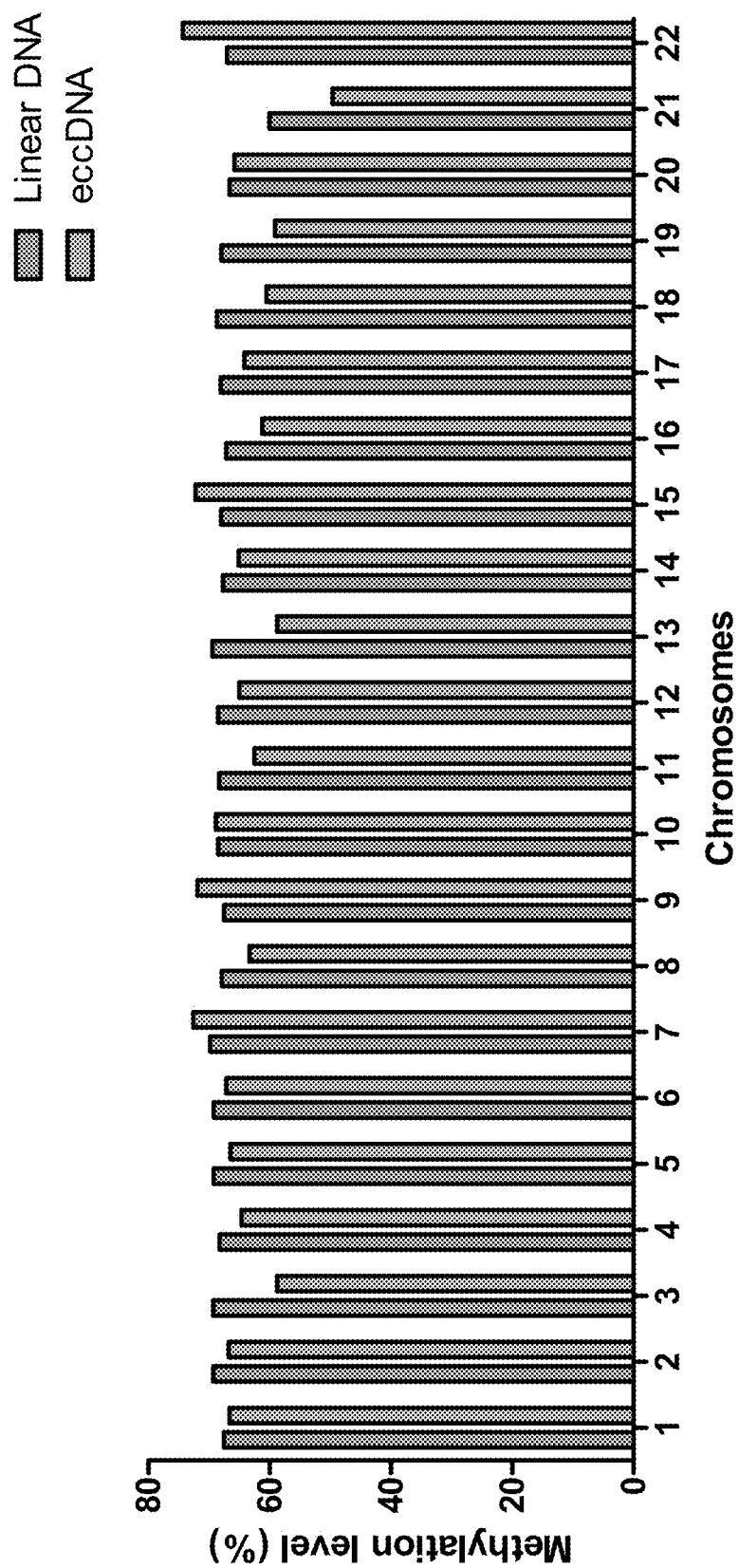
FIG. 14 compares the methylation levels of linear and eccDNA molecules across different chromosomes.

FIG. 14 compares the methylation levels of linear and eccDNA molecules across different chromosomes. In FIG. 14, the methylation levels of eccDNA were comparable to that of linear DNA. Also, by looking at methylation levels across different chromosomes, we could see that eccDNA were of lower methylation levels than linear DNA most of the time.

We also tested whether bisulfite treatment could also facilitate both the identification and methylation analysis of eccDNA. Exo V treatment was coupled with bisulfite treatment for the identification of eccDNA.

Figure 15:
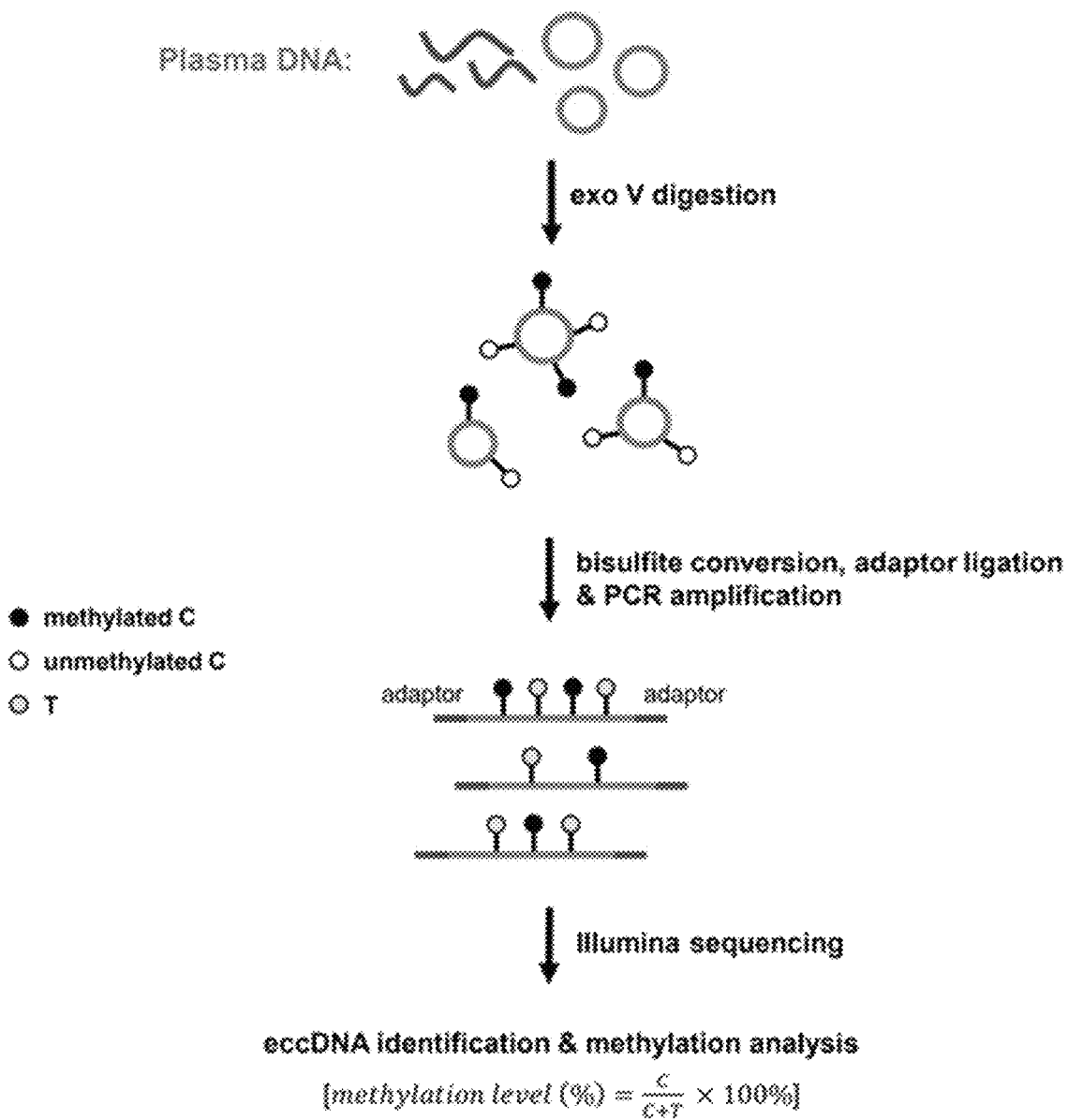
FIG. 15 shows an example workflow of the identification and methylation analysis of eccDNA by bisulfate conversion according to embodiments of the present disclosure.

FIG. 15 shows an example workflow of the identification and methylation analysis of eccDNA by bisulfite conversion according to embodiments of the present disclosure. Plasma DNA was extracted from a pregnant subject and then incubated with exo V to digest the linear DNA in the sample. The remaining DNA was then subjected to bisulfite treatment to convert unmethylated cytosine (C) to uracil and at the same time open up the DNA circles. Single-stranded DNA library construction and Illumina sequencing were then performed, where the unmethylated C-turned-uracil will be represented as T, leaving the methylated C bases unchanged. Bioinformatic pipelines were developed for the identification, size profiling and methylation analysis of eccDNA molecules.

Given the harsh nature of bisulfite treatment and its resultant DNA damage, we hypothesized that bisulfite treatment alone might achieve the conversion of unmethylated cytosine to uracil and tear open circular DNA molecules at the same time. To test this hypothesis, we first investigated whether circular DNA species such as mitochondrial DNA (mtDNA) and plasmid DNA could be linearized by bisulfite treatment. In one experiment, we treated plasma DNA samples either with exo V only or with exo V+bisulfite. In this experiment, the percentages of mtDNA reads in the library were 0.139% for the exo V+bisulfite sample and 0.034% for the exo V only sample, which was a 3.1-fold difference. In another experiment, we added the same amount of pBR322 plasmid DNA to the plasma DNA sample before and after bisulfite treatment. When pBR322 was added before bisulfite treatment, the percentage of pBR322 reads in the library was 31.4%; when added after bisulfite treatment, this percentage dropped to 0.43%, which was a 72-fold difference. Thus, bisulfite treatment could linearize circular DNA species. Our data also suggested that such approaches could potentially be developed into ones that provide the sequence, size and methylation information of eccDNA molecules at the same time.

These new methods we developed could possibly be applied to both tissue and cell-free eccDNA.

5. Method Using Transposases

Accordingly, a method can use a transposase as part of analyzing eccDNA. Such a technique can be used in combination with other methods described herein, e.g., for analysis of eccDNA as well as mtDNA. Downstream analysis can include measurement of properties of the sample using the detection of the circular DNA.

In step 1, a biological sample of an organism can be received. Examples of biological samples are provided herein, such as plasma and serum. The biological sample includes a plurality of extrachromosomal circular DNA (eccDNA) molecules. The eccDNA may be from any number of chromosomes, including the autosomes and/or sex chromosomes. Each of the plurality of eccDNA molecules includes a junction at which nucleotides at two separated genomic locations are immediately adjacent to one another. Junction 1016 is an example of such a junction with regions 1002 and 1006 including such two separated genomic locations that are immediately adjacent to one another.

In step 2, cleaving is performed using a transposase. In some implementations, more than one type of transposase can be used. The transposases can have attached two adapter sequences, e.g., 1012 and 1014 in FIG. 10A.

In step 3, the transposase is used to attaching adapter sequences to both cleaved ends of each of the plurality of eccDNA molecules, thereby forming a set of linearized DNA molecules that each includes the junction and the adapter sequences.

In step 4, for each of the linearized DNA molecules, sequencing of at least both ends of the linearized DNA molecules can be performed to obtain one or more sequence reads. The one or more sequence reads may or may not include the junction. If a read does not include the junction, an eccDNA molecule can still be identified using the directionality of the mapping, as described in table 1. In some embodiments, two sequence reads (one for each end) can be obtained. In other embodiments, a single sequence read of the entire linearized DNA molecule can include both ends, as is described herein. The sequence reads may also include the adapter sequences.

After the sequence reads are obtained, the sequence reads can be mapped to a reference genome, e.g., to see if they map in a reverse orientation. If they do map in a reverse orientation (example criterion), then the correspond linearized DNA molecule can be identified as originally being circular. Accordingly, for each of the linearized DNA molecules, a pair of end sequences for the linearized DNA molecule from the one or more sequence reads can be selected. The pair of end sequences do not include the junction. An example of such end sequences are end sequence 1046 and end sequence 1048 in FIG. 10. A direction of each of the pair of end sequences is reversed to obtain a pair of reversed end sequences. An example of such reversed end sequences are reversed end sequence 1056 and reversed end sequence 1058. The pair of reversed end sequences can then be mapped to a reference genome.

The mapped reversed end sequences can be analyzed to measure a property of the biological sample. Examples of such measurements are provided herein. Such analysis can use a collective value (e.g., count, size, or methylation) of the detected eccDNA. Accordingly, the method can further include identifying (detecting) the linearized DNA molecule as originating from an eccDNA molecule based on the pair of reversed end sequences mapping to the reference genome (other criterion provided in table 1 below), and determining a collective value of the identified eccDNA molecules, wherein analyzing the mapped reversed end sequences to measure the property of the biological sample uses the collective value.

E. Method for Analyzing eccDNA

Figure 16:
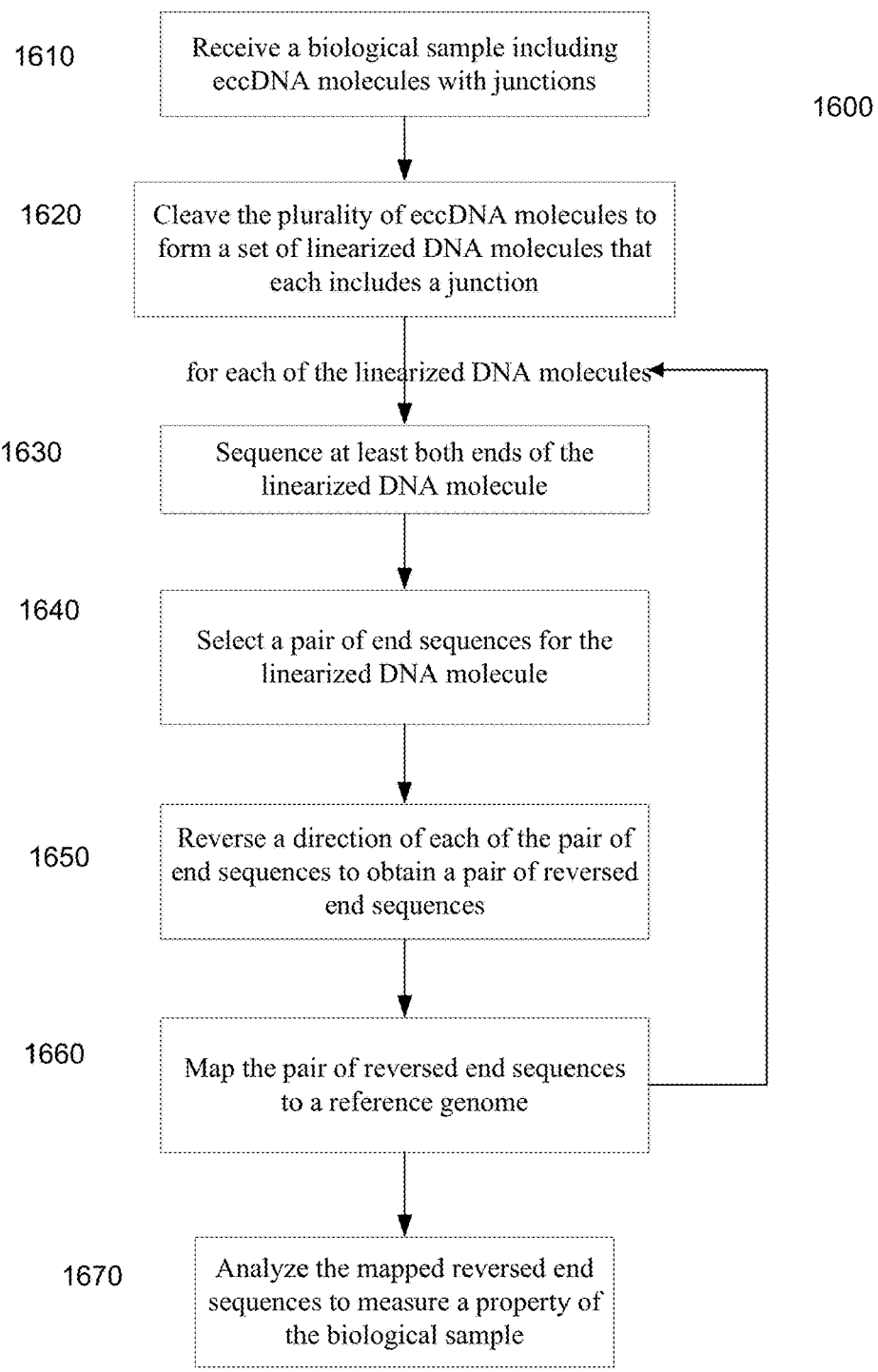
FIG. 16 is a flowchart illustrating a technique for analyzing circular nuclear DNA according to embodiments of the present disclosure.

FIG. 16 is a flowchart illustrating a method 1600 for analyzing circular nuclear DNA according to embodiments of the present disclosure. While method 1600 includes physical steps, such steps may be performed using machinery (e.g., robotics) that is controlled by a computer system. In some implementations, circular nuclear DNA can be analyzed at the same time as linear nuclear DNA. Method 1600 can identify circular nuclear DNA according to one or more criteria and use such circular DNA in determining a property of the sample.

At block 1610, a biological sample of an organism is received. The biological sample includes a plurality of extrachromosomal circular DNA (eccDNA) molecules. The eccDNA may be from any number of chromosomes, including the autosomes and/or sex chromosomes. Each of the plurality of eccDNA molecules includes a junction at which nucleotides at two separated genomic locations are immediately adjacent to one another, e.g., as described for FIGS. 1 and 10A. Two locations are immediately adjacent if they occur in consecutive positions in a sequence read. In any of the embodiments, the eccDNA may be cell-free, e.g., in plasma, serum, and similar samples.

At block 1620, the plurality of eccDNA molecules are cleaved to form a set of linearized DNA molecules that each includes the junction. As examples, the cleaving can be performed using a restriction enzyme or a transposase. Example processes are described in FIGS. 1 and 10A.

At block 1630, each of the linearized DNA molecules can be sequenced at least at both ends of the linearized DNA molecules to obtain one or more sequence reads. The one or more sequence reads may or may not include the junction. If they do, only one or both of the reads may include the junction when paired-end sequencing is performed, while a single read of the entire molecule would include the junction. If a read does not include the junction, an eccDNA molecule can still be identified using the directionality of the mapping, as described in table 1. For paired-end sequencing, various lengths of sequencing can be performed at the ends.

At block 1640, a pair of end sequences for the linearized DNA molecule is selected from the one or more sequence reads. A pair of end sequences may be selected from a single sequence read of the entire DNA molecule. In some embodiments, the pair of end sequences does not include the junction. For example, the pair of end sequences can correspond to a seed as described above, e.g., for FIGS. 2A and 2B. The length of the end sequences can be varied and multiple end sequences can be selected and tried for later mapping steps. If an initially selected sequence read cannot be mapped, then a smaller end sequence can be used.

At block 1650, a direction of each of the pair of end sequences is reversed to obtain a pair of reversed end sequences. The reversal can be accomplished relative to a strand of a reference genome, e.g. by selecting a particular stand of a reference genome to map to. Such a reversal is described for different scenarios for FIGS. 1 and 10A, with one scenario being shown in FIGS. 1 and 10A. The reversal allows the detection of circular DNA as would occur due to a cut at a place other than the junction.

At block 1660, the pair of reversed end sequences are mapped to a reference genome. FIGS. 2A and 2B provide examples for such mapping, as well as FIGS. 1 and 10A. If the pair of reversed end sequences are indeed mapped successfully, the DNA molecule can be identified as circular. Other criteria can be used to identify circular DNA, e.g., as shown in table 1. The existence of a cutting tag (potentially at both ends of a DNA fragment) can be used as a separate or additional criterion.

As part of or after the mapping, the junction can be detected, e.g., for embodiments where a size of the circular DNA molecule is to be determined. The ends of the original linear fragment can be identified based on the nucleotides on either end of the junction. Analyzing a mapped reversed end sequence can include comparing bases in the one or more sequence reads extending past each of the mapped reversed end sequences to the reference genome until a mismatch condition is identified. FIG. 2B provides one example of a mismatch condition. End positions of a linear DNA fragment from which the eccDNA molecule was formed can be identified based on a location of the mismatch conditions in the reference genome. The end positions can be used to determine a size of the linear DNA fragment using the end positions.

At block 1670, the mapped reversed end sequences are analyzed to measure a property of the biological sample. The mapped reversed end sequences can be analyzed to measure a property of the biological sample. Examples of such measurements are provided herein. Such analysis can use a collective value (e.g., count, size, or methylation) of the detected eccDNA. Accordingly, the method can further include identifying the linearized DNA molecule as originating from an eccDNA molecule based on the pair of reversed end sequences mapping to the reference genome (other criterion provided in table 1), and determining a collective value of the identified eccDNA molecules, wherein analyzing the mapped reversed end sequences to measure the property of the biological sample uses the collective value.

Accordingly, the plurality of eccDNA molecules can be detected based on the pair of reversed end sequences mapping to the reference genome. A collective value of the detected eccDNA molecules can be determined, where analyzing the mapped reversed end sequences to measure the property of the biological sample uses the collective value. Example of the collective value include a count (e.g., aligned to a particular region), a size, or a methylation level determined using the detected eccDNA molecules Regarding use of size, a size distribution of the sizes measured for the plurality of eccDNA molecules can be determined and used to measure the property of the biological sample. For example, if the sample is from a pregnant female or from a subject with cancer, the size distribution will shift for a region that has a copy number aberration for the region, as fetal and tumor fragments are statistically shorter than the DNA from fragments from the maternal/healthy cells. An example of such size profiling is provided in section I.C.1.

Regarding use of a count, analyzing the mapped reversed end sequences can include counting a number of the plurality of eccDNA molecules that map to a chromosomal region, where the property of the biological sample is of the chromosomal region. The number can then be used to measure the property of the chromosomal region. In such an example, the property can be a copy number aberration in the chromosomal region, e.g., as described above in section I.C.

Analyzing the mapped reversed end sequences can include measuring a methylation level in the chromosomal region using DNA molecules in the biological sample. The methylation level can be measured using linear DNA molecules (i.e., originally linear) and/or circular DNA molecules (i.e., which get linearized). In various implementations, the methylation level can be determined to exhibit hypermethylation by comparing to a cutoff. The copy number aberration and the methylation density can be used to detect a condition with the organism. As examples, the condition can be fragile X syndrome or the triplet repeat expansion.

As examples, the property is sex or genotypic information for the region. Such genotypic information can be human leukocyte antigen status or blood group. Accordingly, a fragment can be analyzed for detecting a marker (e.g., Y chromosome, allele of a genotype, etc.). Such examples can be considered that a region carries information regarding the property of the biological sample. As other examples, the property is an aberration including a sequence alteration, duplication, expansion, deletion, or an amplification in the biological sample.

The biological sample may be obtained from a subject being screened for cancer. A level of cancer in the organism can be determined based on a chromosomal region having the aberration or at least a specified number (threshold) of aberrant regions. As described above, the inclusion of eccDNA in the determination can increase detection accuracy, e.g., as the chromosome could repair itself after releasing an eccDNA, so that the chromosome copy does not show the aberration, but the total genetic material would.

The biological sample may be obtained from a female pregnant with a fetus. The aberration or a sequence imbalance can be detected in the fetus. For example, an amplified/deleted region can be detected using the eccDNA. As another example, genotypic information can be detected by identifying variants that occur in linear DNA (nuclear or mitochondrial).

When a restriction enzyme is used to cut a particular sequence, a particular sequence spanning the pair of end sequences of at least a portion of the linearized DNA molecules can be identified at a cutting tag, e.g., CCGC as in the example of FIG. 1. When a transposase is used, the specific adapter sequences can be used as a cutting tag.

The sample can include a first tissue type (e.g., maternal/healthy) and a second tissue type (e.g., fetal/tumor). The first tissue type can be homozygous for a first allele at a locus, and the second tissue type can be heterozygous for the first allele and a second allele at the locus. A first number of the mapped reversed end sequences (proxy for circular DNA) that have the first allele at the locus can be determined. A second number of the mapped reversed end sequences that have the second allele at the locus can be determined. A fractional concentration of eccDNA molecules from the second tissue type can be determined using the first number and the second number. The numbers for cell-free linear DNA can also be determined and a collective concentration for both can be determined.

As a further example of the analysis in block 1670, sequence variants relative to a reference genome (or to the subject's constitutional genome, consensus sequence of healthy cells) can be identified in the eccDNA. A number of sequence variants relative to the reference can be determined in the mapped reversed end sequences. A level of cancer can be determined using the number of fragments with sequence variants, e.g., by comparing the number to a threshold. A specific number of sequence variants can be required at any given locus before their contribution is added to the total number of eccDNA with sequence variants. Further, the eccDNA may be specific to tumor cells (e.g., has a variant relative to a reference genome or constitutional genome) or preferentially released from tumor cells (e.g., as being from an amplified region). After depletion of linear DNA using e.g. exo V, the tumor eccDNA would be greatly enriched and improve the detection sensitivity.

II. Simultaneous Dissection of Circulating Linear and Circular Mitochondrial DNA Chiu et al revealed that both particle-associated (e.g., identified via physical filtration step, including intact mitochondria) and free mitochondrial DNA (mtDNA) (e.g., including DNA released during DNA extraction) were present in plasma using real-time quantitative PCR (qPCR) plus filtrations with different pore sizes (Chiu et al. Clin Chem. 2003; 49:719-26). However, Chiu et al's method could not accurately quantify the relative ratio of linear to circular forms regarding cell-free mtDNA because qPCR would amplify both linear and circular DNA bearing the primer annealing sites. Recently, Newell et al. reported the presence of full-length mtDNA in cell-free human plasma by using two long overlapping amplicons (9,239 bp and 11,216 bp, respectively) (Newell et al. Mol Genet Metab. 2018; doi: 10.1016/j.ymgme.2018.10.002). It is not surprising to see that the larger amplicons can be amplified because of the a priori knowledge of co-existence of both particle-associated and free mitochondrial DNA in plasma (Chiu et al. Clin Chem. 2003; 49:719-26). However, such PCR assays targeting amplicons of several thousand kilobases are not able to amplify short cell-free mtDNA molecules, for example, <600 bp. Thus, PCR-based assays lack the ability to simultaneously infer the mitochondrial DNA forms (circular versus linear) in plasma DNA In this disclosure, some embodiments can provide a new approach for simultaneously analyzing the short linear and circular mtDNA molecules. This disclosure allows (1) quantifying the relative quantity between linear and circular forms of cell-free mtDNA molecules in the plasma DNA pool, e.g., to determine a level of disease; and (2) deducing the tissue of origin of linear and circular mtDNA molecules in the plasma DNA pool, e.g., as part of determining whether a non-hematopoietic tissue or a hematopoietic tissue has the sequence variant.

A. Principle of Technology

The linear and circular cell-free mtDNA co-exist in plasma DNA molecules. In order to make the circular cell-free mtDNA amenable to be sequenced, we linearize the circular form of such molecules. There are multiple ways to perform the linearization of circular cell-free mtDNA molecules, for example, but not limited to, sonication and enzyme-mediated cleavage, e.g., as described above. In one example, the enzyme-mediated cleavage involves a restriction enzyme. In another example, the enzyme is a nuclease other than a restriction enzyme (e.g. DNASE1L3 or DNASE1). In yet another example, the enzyme-mediated cleavage involves a transposase.

Figure 17:
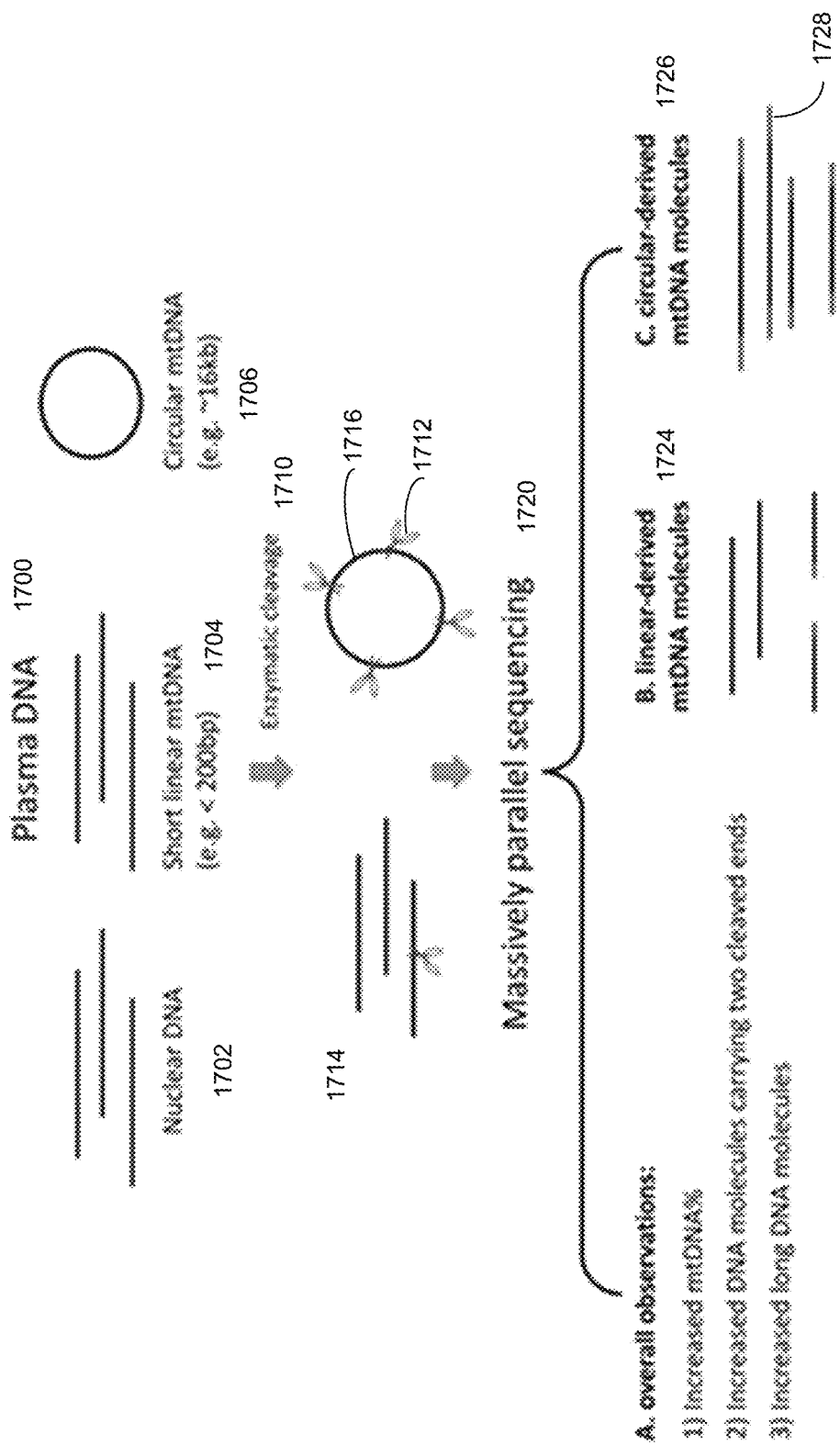
FIG. 17 shows an example technique for differentiating the cell-free circular-derived and linear-derived mtDNA molecules in plasma according to embodiments of the present disclosure.

FIG. 17 shows an example technique for differentiating the cell-free circular-derived and linear-derived mtDNA molecules in plasma according to embodiments of the present disclosure. The plasma DNA molecules comprise a mixture of short linear DNA and circular DNA. As shown, plasma DNA 1700 includes nuclear DNA 1702, short linear mtDNA 1704, and circular mtDNA 1706.

At step 1710, enzymatic cleavage is performed. Scissors 1712 (red) represent the restriction enzyme cutting sites. Normally the circular DNA in plasma is not able to be directly sequenced, e.g., using the Illumina sequencing platform. To make the circular DNA in plasma amenable to be sequenced effectively, we create nicks in the circular DNA. On the basis of artificial cleavage of circular DNA molecules (via restriction enzymes, other nuclease, transposase or physical methods such as sonication), we can linearize those circular DNA molecules to form pieces of relatively short linear DNA.

Accordingly, as shown in FIG. 17, to differentiate the short linear DNA and circular mtDNA, enzymatic cleavage is used. Because the majority of short linear mtDNA would be expected to be less than 200 bp (Lo et al., Sci Transl Med. 2010; 2:61ra91; Jiang et al., Proc Natl Acad Sci USA. 2015; 112:E1317-E1325) and circular mtDNA would expect to be around 16.5 kb, an intended selection of restriction enzyme would allow for making most cutting events preferentially occurring in the circular mtDNA. For example, if we choose a 4-bp cutter (e.g., a restriction enzyme that cuts at a specific 4-base sequence), each fragment with <200 bp would, on average, have less than one such enzymatic cleavage site. This is because one would expect such a 4-base recognition site to occur every once in every 256 bp (with 256 being $4^4$). The probability of having two cut sites due to a random chance would be only 1/65536, which is very much lower than the probability of being cut for an intact circular mtDNA. Accordingly, if a DNA fragment had two cutting tags corresponding to the 4-base sequence of the restriction enzyme, then that DNA fragment could be identified as originating from circular mtDNA. The particular cutting tag can be chosen to occur with at least a specified spacing between cutting sites for a reference mitochondrial genome.

As we know the sequence of the mitochondrial genome, one could select a restriction enzyme (e.g. BfaI) that would have a sufficient number of cleavage sites in the proposed circular mtDNA molecules. In our choice for restriction enzymes to use, we also consider the distribution of restriction enzyme sites in the mitochondrial genome such that most the cleaved fragments would have a length suitable to the sequencing platform being used. Such sequencing platforms include, but not limited to, the Illumina sequencing-by-synthesis platform, the Pacific Biosciences Single Molecule, Real-Time (SMRT) system, nanopore sequencing, and semiconductor sequencing (e.g. Ion Proton and the GenapSys Gene Electronic Nano-Integrated Ultra-Sensitive (GENIUS)), etc.

Accordingly, the resulting short linear DNA molecules can then be analyzed by various sequencing platforms. Sequencing 1720 (e.g., massively parallel sequencing) can provide sequence reads for the linear-derived mtDNA molecules 1724 and the circular-derived mtDNA molecules 1726. If using a restriction enzyme to cleave the circular DNA, the larger circular DNA 1716 (e.g. intact circular mtDNA of ~16.5 kb in size) would bear many more cleavage sites in comparison with a spontaneously occurring short linear DNA 1714. Thus, through treating plasma DNA with a restriction enzyme, we can utilize the principle that a plasma DNA molecule carrying two cleaved ends (illustrated by a black line with two red ends 1728, corresponding to cutting tags) would have a much higher likelihood of being artificially derived from a circular DNA molecule, when compared with those molecules that have no cleaved ends or one cleaved end (illustrated by a black line without red ends or a single red end).

In some implementations, following restriction enzyme treatment of the circular mtDNA, each of the resulting linear DNA molecule derived from such enzymatic cleavage must bear two enzyme cleaved ends. Such an end signature can allow differentiating such artificially produced molecules from spontaneously occurring linear mtDNA in plasma. In summary, circular-derived mtDNA would be expected to have two cleaved ends while spontaneously produced linear-derived mtDNA would be expected to have no cleaved ends or occasionally have one cleaved end. We called this new technology Topologic Analysis of Mitochondrial DNA (TopM).

Based on this analysis, the relative quantity of linear and circular DNA forms can be simultaneously determined. In this cleavage-based assay, one cannot completely rule out the existence of "super-long" cell-free linear DNA (>2000 bp) which could bear a considerable probability to produce fragments carrying two cleaved ends. However, according to a priori knowledge of cell-free plasma DNA, the probability of having such a "super-long" cell-free linear DNA is very low because the predominant cell-free DNA molecules in a linear form are reported to be <200 bp (Jiang and Lo. Trends Genet 2016; 32: 360-371).

In some embodiments, the restriction enzyme can be selected to meet one or more of the following criteria:
1) The restriction enzyme recognition site should be at least 4 bp;
2) No star activity (Star activity is the relaxation or alteration of the specificity of restriction enzyme mediated cleavage of DNA that can occur under reaction conditions that differ significantly from those optimal for the enzyme);
3) Methylation insensitive;
4) At least 70% of distances between two cutters in circular mtDNA should be within a specific range, e.g., from 50 to 600 bp, 100 bp to 600 bp, 150 bp to 600 bp, 200 bp to 600 bp, 300 bp to 1000 bp, 500 bp to 2000 bp, 100 bp to 4000 bp, or other combinations, e.g., which are suited for sequencing;
5) The expected sequencing coverage of the mitochondrial genome would be greater than 80%. In other words, 80% of the circular mitochondrial genome can be covered at least once after the restriction enzyme digestion plus sequencing steps, even with a constraint on the length of the sequence reads.

"Methylation insensitive" means that the enzyme can cut both methylated and unmethylated DNA. Many restriction enzymes are sensitive to the DNA methylation states. Cleavage may be blocked when the recognition site is methylated. Thus, methylation insensitive enzymes may be preferable.

Figure 18:
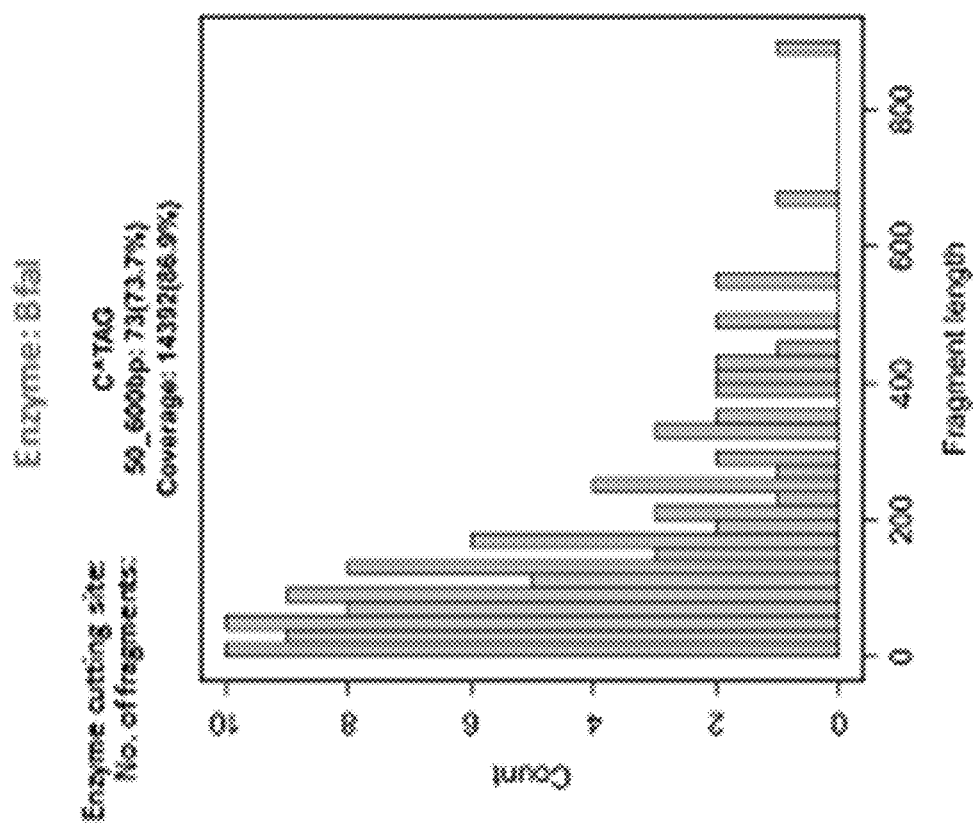
FIG. 18 illustrates the use of the BfaI restriction enzyme to demonstrate a number of principles.

FIG. 18 illustrates the use of the BfaI restriction enzyme to demonstrate a number of principles. BfaI can cut DNA with CTAG motif inside the sequence. The cutting sites are C^TA G and G AT^C. FIG. 18 shows an example of in silico analysis for selecting a restriction enzyme. The x-axis indicates the in silico predicted length of DNA molecules after treatment of the circular mitochondrial genome using BfaI. The y-axis indicates the frequency of a particular fragment length. The length of a DNA molecule is dependent on where the cutting tags exist in the mitochondrial genome, with the length being the distance between two cutting tags. This simulation is for intact circular mtDNA by in silico cutting of the mtDNA genome at enzyme recognition sites.

B. Percentage of mtDNA Between the Enzymatically Cleaved and Untreated Plasma DNA To illustrate the ability to detect circular DNA and to show that circular mtDNA exist in appreciable quantities, we analyzed samples that were enzymatically treated and untreated. We also show the ability to determine a ratio between circular and linear DNA to represent the abundance of circular mtDNA for further applications, such as deduction of tissue origin and diagnosis of diseases.

1. Pregnancy

For sample collection and plasma DNA preparation, we collected 15 plasma DNA samples from 15 pregnant women. Each plasma DNA sample was divided into two aliquots for experimental assays with and without restriction enzyme digestion. Women with singleton pregnancies were recruited from the Department of Obstetrics and Gynecology of the Prince of Wales Hospital, Hong Kong with written informed consent and institutional ethics committee approval. Maternal peripheral blood was collected in EDTA-containing tubes, which were subsequently centrifuged at 1,600 g for 10 min at 4° C. The plasma portion was recentrifuged at 16,000 g for 10 min at 4° C. to obtain cell-free plasma that was stored at −80° C. till further analysis. Plasma DNA was extracted from 4 to 10 mL of plasma using the QIAamp DSP DNA Blood Mini Kit (Qiagen). The plasma DNA was concentrated with a Speed-Vac Concentrator (Savant DNA120; Thermo Scientific) into a 75-µL final volume per sample. Although the following analysis used pregnancy samples, the analysis is equally applicable to samples from non-pregnant subjects.

For sequencing and alignment, we used massively parallel paired-end sequencing for both assays with and without restriction enzyme digestion. The sequenced pair-end reads were aligned to a reference genome database that included all autosomes (chr1, chr2, . . . , and chr22), the sex chromosomes, as well as a mitochondrial genome using SOAP2 (Li et al., Bioinformatics. 2009; 25:1966-7). Various alignment techniques can be used. Such a compiled reference database including both genomes can reduce the influence of homologous regions existing between the nuclear and mitochondrial genomes. For example, some implementations can only keep the uniquely mapped results. Those reads aligned to multiple regions or to both nuclear and mitochondrial genomes with the same mapping quality can be discarded. In one implementation, we allowed up to two nucleotide mismatches for each read, although other numbers of mismatches can be used. As further example criteria, only paired-end reads with both ends aligned to the same chromosome with the correct orientation, spanning an insert size of no more than a specified size (e.g., 600 bp), were used for downstream analyses. After alignment, the chromosome origin, as well as length for each sequenced fragment, could be determined.

We sequenced 15 pregnant samples without treatment of the restriction enzyme (BfaI). We obtained a median of 26 million uniquely mapped paired-end reads (range: 18-40 million) using massively parallel sequencing (Illumina). The median mapping rate was 82% (range: 67-83%). The median number of sequenced mtDNA fragments was 660 per sample (range: 320-1477).

For the treated samples, prior to sequencing, we used the restriction enzyme (BfaI) to digest the 15 matched plasma DNA samples. Plasma DNA was digested with BfaI (New England Biolabs) under the following conditions: 10 units BfaI (1 µl), 1× CutSmart buffer (5 µl) and DNA in the 50 µl reaction volume. The reaction was incubated at 37 degree Celsius for 2 hours, then heat-inactivated at 80° C. for 20 minutes. The enzymatically cleaved plasma DNA samples were subjected to end-repair, A-tailing, and sequencing adaptor ligation. The adaptor-ligated plasma DNA samples were then sequenced using the Illumina platform. The skilled person will appreciate the various sequencing platforms and preparation techniques that can be used.

Figure 19B:
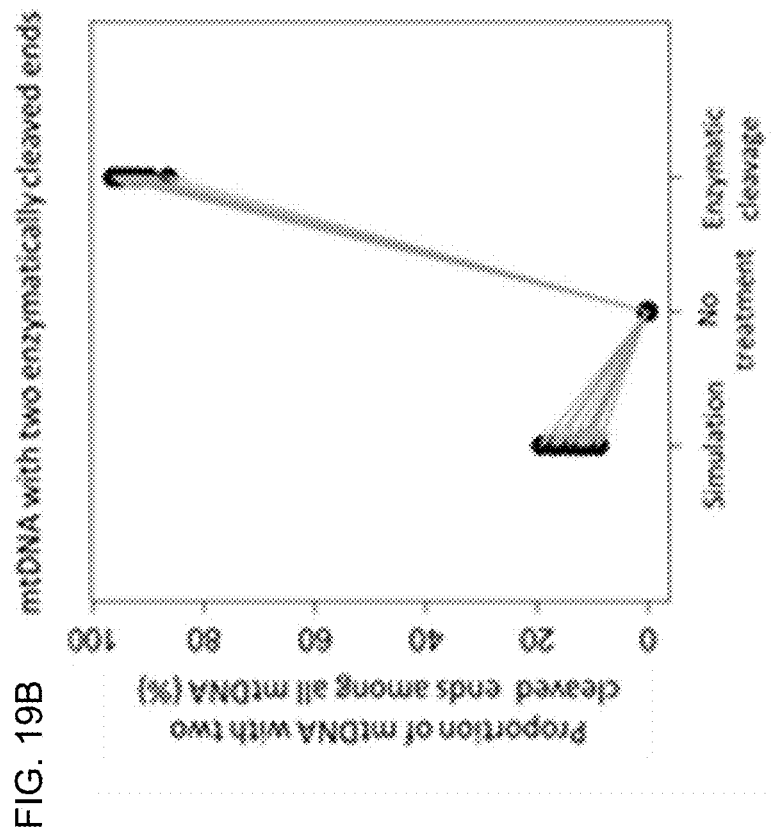
FIGS. 19A and 19B show the comparison of plasma mtDNA metrics for plasma DNA with and without restriction enzyme (BfaI) digestion according to embodiments of the present disclosure.
Figure 19A:
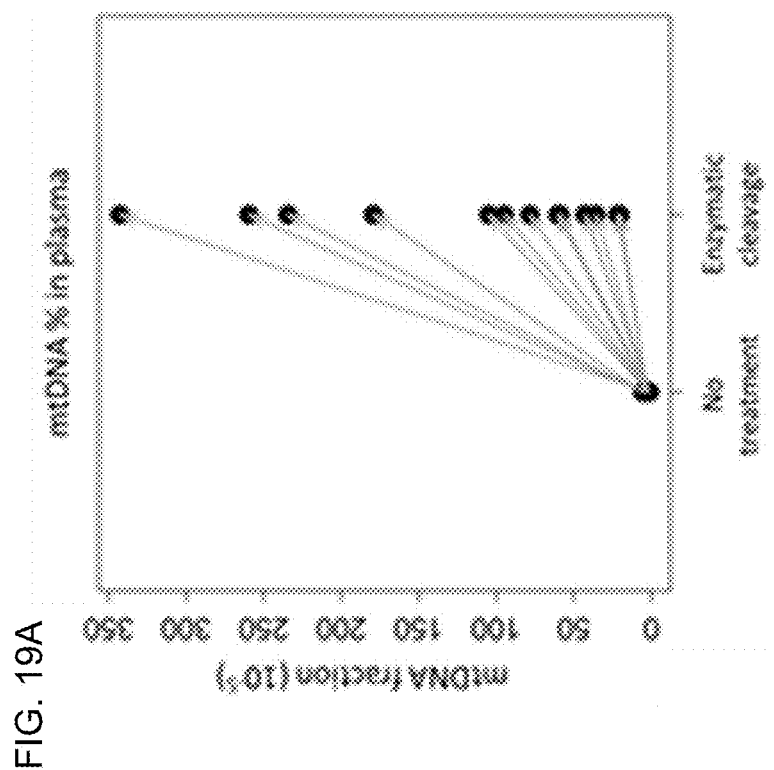

FIGS. 19A and 19B show the comparison of plasma mtDNA metrics for plasma DNA with and without restriction enzyme (BfaI) digestion according to embodiments of the present disclosure. The lines indicate measurements for different portions (treated and untreated) obtained from a same sample.

FIG. 19A shows the proportion of mtDNA fragments in the total plasma DNA molecules. The total plasma DNA molecules include mtDNA molecules and nuclear DNA molecules. With no treatments, all samples provided about the same percentage of mtDNA, which was near zero. But, the percentage of mtDNA in the treated samples having undergone enzymatic cleavage increases dramatically, with different samples having different percentages of mtDNA fragments. This results shows that much of the mtDNA in a plasma sample is circular mtDNA, and enzymatic cleavage enables detection of such circular mtDNA molecules.

FIG. 19B shows the proportion of mtDNA fragments with two enzymatically cleaved ends in the total plasma mtDNA molecules. The horizontal axis shows: Simulation: in silico cleavage on plasma DNA; No treatment: Plasma DNA without enzymatic cleavage; Enzymatic cleavage: plasma DNA with enzymatic cleavage.

For the group of plasma DNA samples treated with BfaI, we obtained a median of 24 million uniquely mapped paired-end fragments (range: 14-30 million). The median mapping rate was 79% (range: 73-81%). The median number of sequenced mtDNA fragments was 9,777 (range: 1,725-37,650). The proportion of mtDNA fragments among the total plasma DNA molecules in the plasma DNA samples treated with BfaI was on average 17× higher than that of plasma DNA samples without BfaI treatment (FIG. 11A). The proportion of mtDNA fragments with two cleaved ends among all mtDNA was above 80%, which was much higher than that of samples without restriction enzyme treatment (<1%) and the prediction using in silico cutting using a computer program (<20%). These results suggested that the fragments with two cleaved ends would most likely have originated from intact circular mtDNA molecules that were not able to be sequenced in the plasma DNA samples without restriction enzyme treatment.

Figure 20:
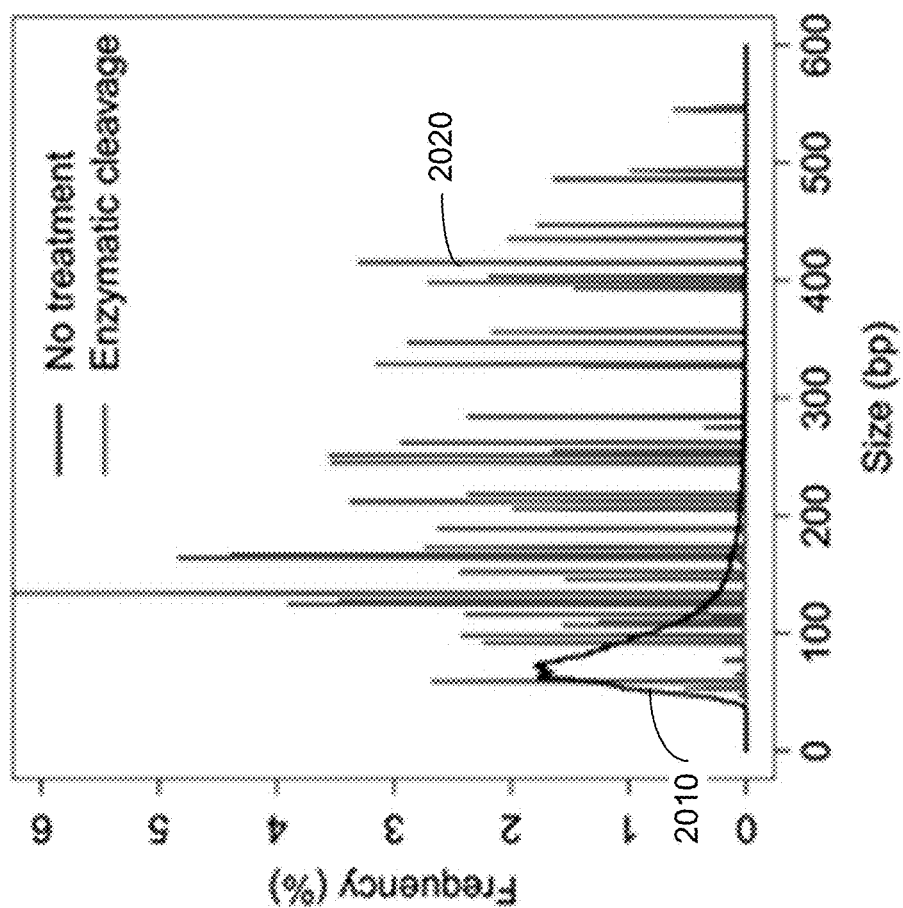
FIG. 20 shows size profiles of sequenced mtDNA fragments under the different treatments.

FIG. 20 shows size profiles of sequenced mtDNA fragments under the different treatments. No treatment 2010 (black) corresponds to plasma DNA without restriction enzyme treatment. Enzymatic cleavage 2020 (red) corresponds to plasma DNA with restriction enzyme treatment. FIG. 20 showed that there were more long mtDNA fragments in plasma DNA treated by enzymatic cleavage in comparison with plasma DNA without the treatment of restriction enzyme. FIG. 20 further provides evidence that that the fragments with two cleaved ends would be derived from intact circular mtDNA molecules that were not able to be sequenced in the plasma DNA samples without restriction enzyme treatment.

Figure 21B:
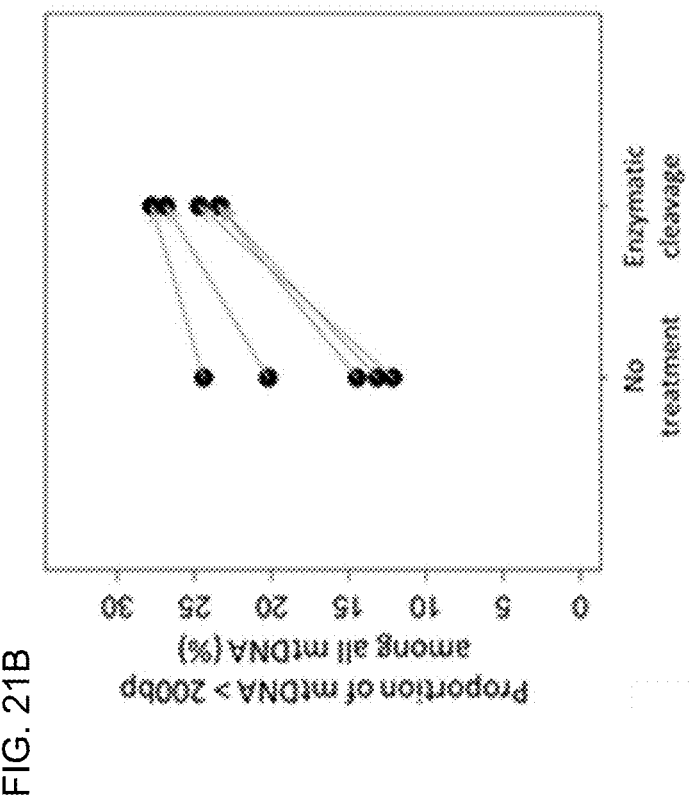
FIGS. 21A and 21B show the proportion of mtDNA>200 bp among all autosomes and among all mtDNA
Figure 21A:
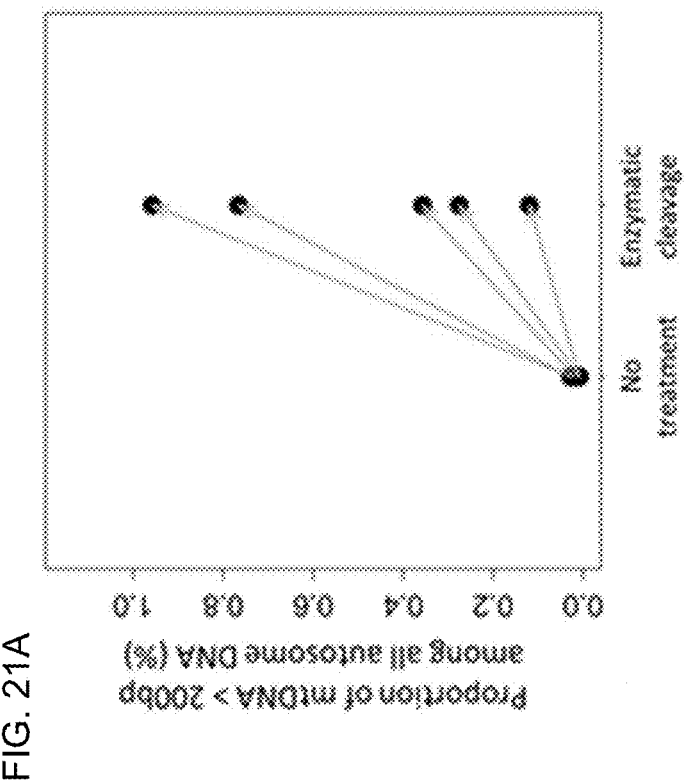

FIGS. 21A and 21B show the proportion of mtDNA>200 bp including autosome DNA and among all mtDNA. The lines indicate different portions (treated and untreated) obtained from a same sample. FIG. 21A shows that the proportion of long mtDNA (>200 bp) among all DNA in plasma DNA samples with enzymatic cleavage (median: 36.49%; range: 33.17-42.58) was 5.9 times higher than that of plasma samples without the treatment of restriction enzyme (median: 6.21%; range: 1.76-18.44). The increase is expected based on those cutting tags being more than 200 bp apart. And, the proportion of long mtDNA (>200 bp) among all mtDNA also increases, which again shows that DNA fragments from cleavage of circular mtDNA is being detected.

Figure 22:
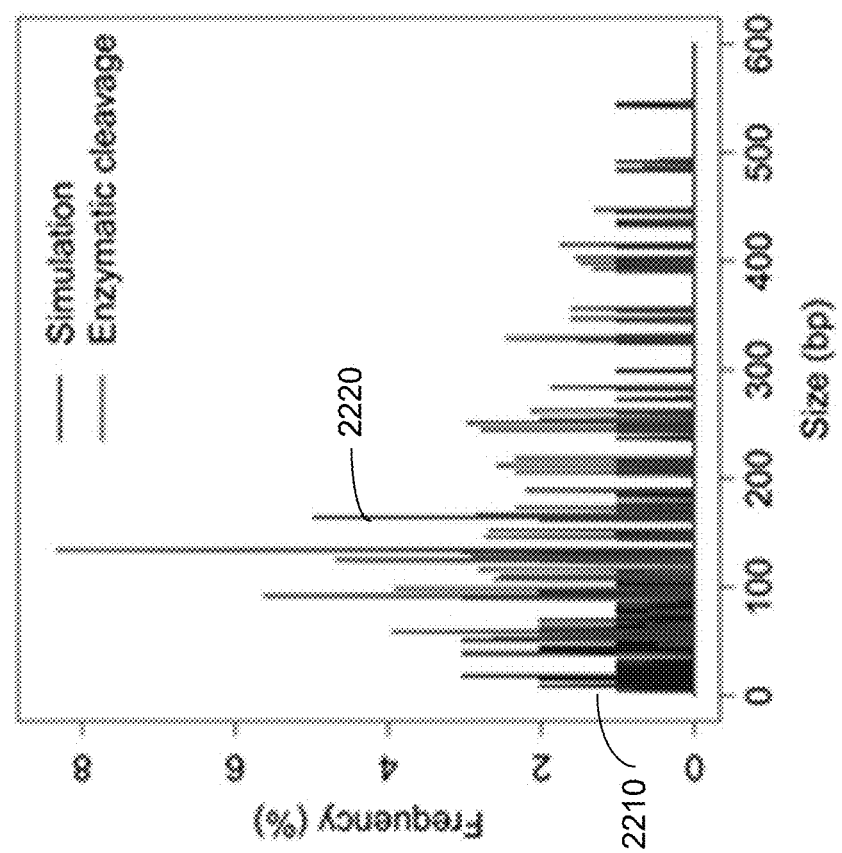
FIG. 22 shows the size profiles of mtDNA fragments with two cleaved ends for the enzymatic cleavage 2020 in FIG. 20 and simulation results in FIG. 18.

FIG. 22 shows the size profiles of mtDNA fragments with two cleaved ends for the enzymatic cleavage 2020 in FIG. 20 and simulation results in FIG. 18. The measured results of enzymatic cleavage 2220 correlated well with the size profile 2210 of fragments predicted by in silico cutting of the circular mitochondrial genome in FIG. 18. Accordingly, the size profiles of mtDNA fragments with two cleaved ends correlated with the size profile of fragments predicted by in-silico cutting of the circular mitochondrial genome.

There is a theoretical possibility that "super-long" linear mtDNA (e.g. >2000 bp) that, if present, might contribute cleaved molecules to the population of mtDNA fragments bearing two restriction enzyme-associated cleaved ends. However, the possibility of such a scenario would be relatively low based on a number of lines of evidence listed below:

1) There is no obvious long-tail distribution in the size distribution of plasma mtDNA molecules without the treatment of restriction enzyme (FIG. 20).
2) In a sequencing experiment in which plasma DNA was sequenced using the Pacific Biosciences SMRT technology, we obtained approximately 850,977 sequences of plasma DNA. This sequencing technology was chosen for this experiment because it could generate sequence reads that were much longer than those generated by technologies such as the sequencing-by-synthesis technology from Illumina. Amongst the Pacific Biosciences reads, we identified 24 mtDNA fragments. However, not a single one of these were longer than 1000 bp (FIG. 23).

Figure 23:
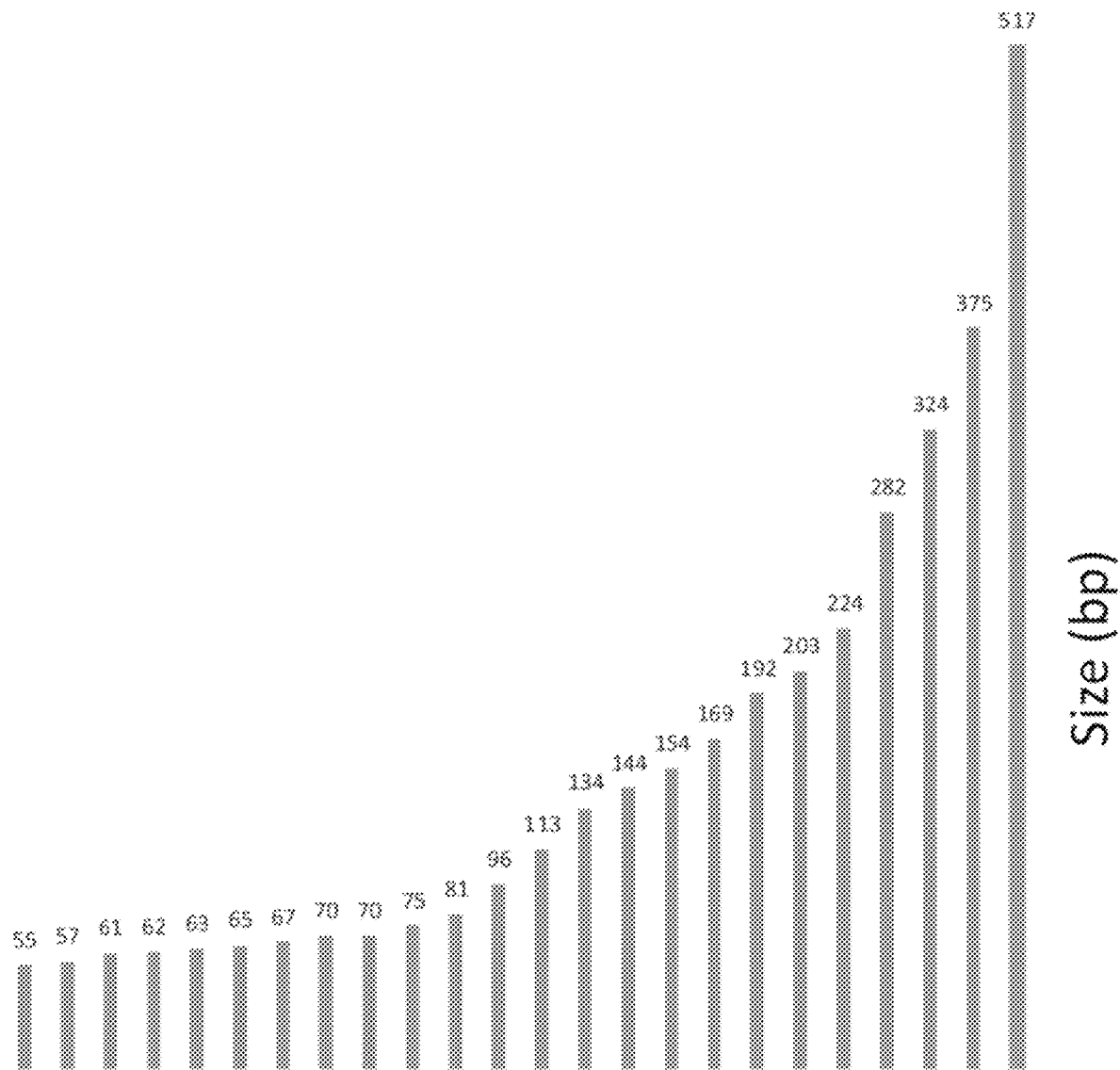
FIG. 23 shows MtDNA fragments in plasma DNA without the treatment of restriction enzyme sequenced by Pacific Biosciences Single Molecule, Real-Time (SMRT) sequencing platform.

FIG. 23 shows mtDNA fragments in plasma DNA without the treatment of restriction enzyme sequenced by Pacific Biosciences SMRT sequencing platform. As mentioned above, 24 mtDNA fragments were identified. The length of each of the DNA fragments is provided in FIG. 23. Since the length of the linear mtDNA fragments are limited, long linear mtDNA would not contribute significantly to the population of mtDNA fragments bearing two restriction enzyme-associated cleaved ends.

Figure 24A:
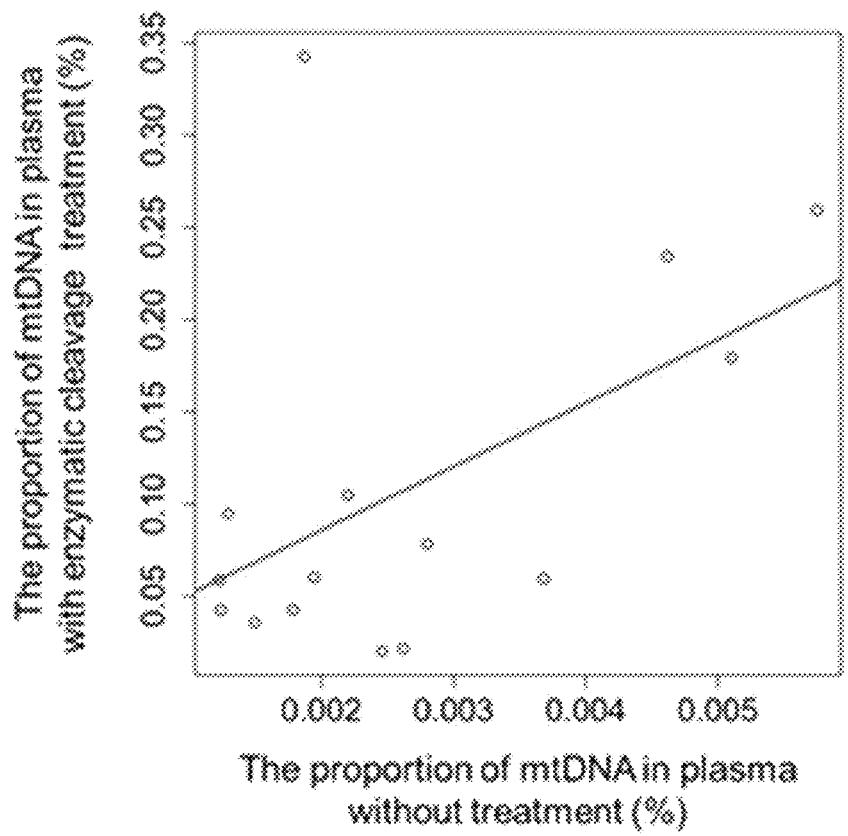
FIG. 24A shows a correlation between the proportion of mtDNA in plasma with and without enzymatic cleavage treatment according to embodiments of the present disclosure.

FIG. 24A shows a correlation between the proportion of mtDNA in plasma with and without enzymatic cleavage treatment according to embodiments of the present disclosure. To get the two data points that comprise a single point on the plot, we divided the samples into at least two aliquots each before conducting assays. Different aliquots were treated and untreated, thereby providing the different measurements. The vertical axis corresponds to the proportion of mtDNA for all DNA (nuclear and mitochondrial) for a treated sample, and the horizontal axis corresponds to the proportion of mtDNA for all DNA (nuclear and mitochondrial) without treatment. This correlation demonstrates that the linear mtDNA amount can still be reflected in the new assay with enzymatic digestion.

Figure 24B:
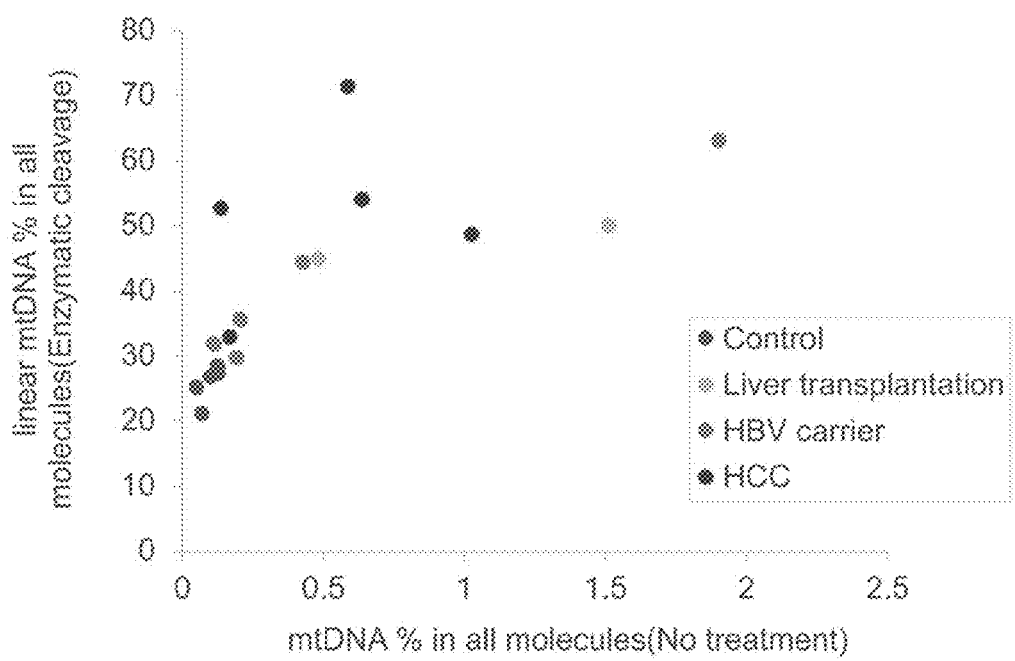
FIG. 24B shows the proportion of linear-derived mtDNA in all DNA (nuclear and mitochondrial) in plasma DNA with enzymatic treatment correlated with that of all mtDNA in all plasma DNA (nuclear and mitochondrial) without treatment according to embodiments of the present disclosure.

FIG. 24B shows the proportion of linear-derived mtDNA in all DNA (nuclear and mitochondrial) in plasma DNA with enzymatic treatment correlated with that of all mtDNA in all plasma DNA (nuclear and mitochondrial) without treatment (r=0.5, p-value=0.05). Although the proportion was much higher for the treated samples, a higher proportion in treated samples resulted in the corresponding untreated sample likely having a higher proportion. These results indicate that the dosage of spontaneously occurring linear mtDNA fragments (i.e., fragments that are present naturally or spontaneously, and not created by artificial enzyme digestion) in a plasma DNA sample with restriction enzyme treatment could still allow the monitoring of the relative quantity of the original mtDNA present in the blood circulation.

In the above description, we have used BfaI as an example of a restriction enzyme that can be used. Other examples of restriction enzymes include BsaJI, BseDI, BssECI, SecI, Aci, AluI, MaeI and XspI. In other embodiments, one can use restriction enzymes that are not 4-base cutters, e.g. 6-base cutters. In yet other embodiments, one can use a combination of restriction enzymes. In yet other embodiments, one can used nucleases other than a restriction endonuclease, e.g. DNASE1L3 (Serpas et al. Proc Natl Acad Sci USA 2019; 116: 641-649). In other embodiments, one can also use a transposase such as Tn5, Mu, Tn7 or Ty1. In yet other embodiments, one can use non-enzymatic method to open the circular mitochondrial DNA, e.g. physical methods such as sonication, repeated freeze-thawing, repeated heating/cooling cycles, etc.

2. Cancer Analysis (e.g., HCC)

We previously reported that the increase of cell-free mtDNA molecules was associated with patients with hepatocellular carcinoma (HCC) compared with healthy controls, HBV carriers, and subjects suffering from cirrhosis (Jiang et al., Proc Natl Acad Sci USA. 2015; 112:E1317-E1325). Thus, we reasoned that TopM would find its utility in the context of patients with hepatocellular carcinoma (HCC).

We sequenced plasma samples from 5 HBV carriers and 5 HCC patients. We prepared three aliquots of plasma DNA for each case, respectively, to conduct three types of assays: (1) sequencing without treatment with a restriction enzyme; (2) sonication prior to sequencing (sonication); and (3) restriction enzyme digestion prior to sequencing (enzymatic cleavage). For the assay involving sonication, plasma DNA (60 μl) was sheared with a focused-ultrasonicator (Covaris S220). The following settings were used: peak incident power 175 W, duty factor 10%, 200 cycles per burst, and treatment time of 120 seconds, although other settings may be used.

Figure 25A:
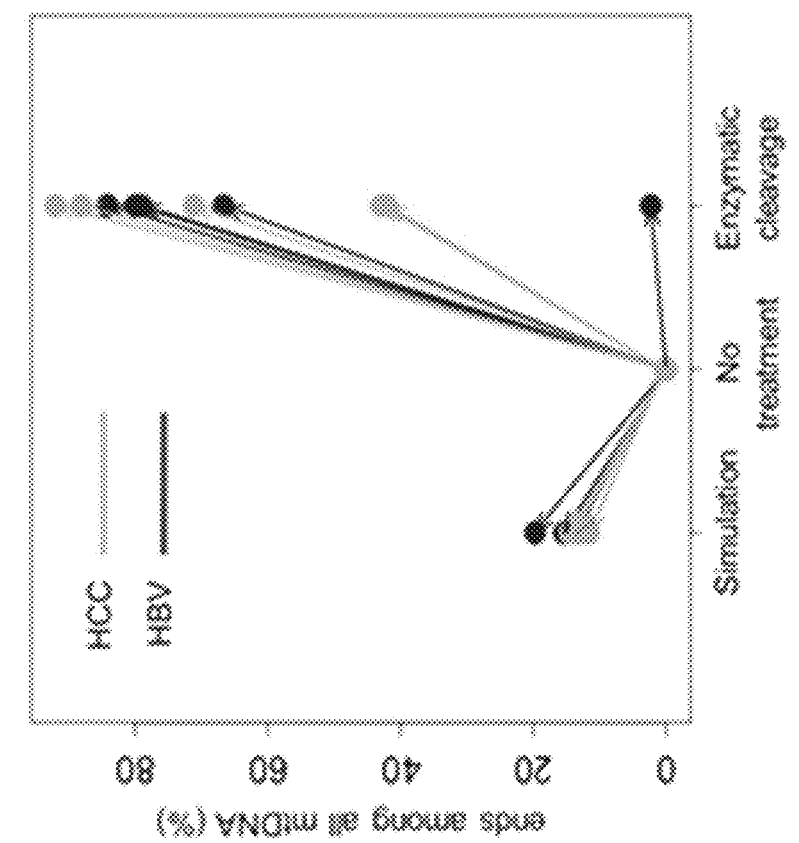
FIGS. 25A and 25B show a comparison of plasma mtDNA metrics for plasma DNA of HBV and HCC samples with and without restriction enzyme digestion.
Figure 25B:
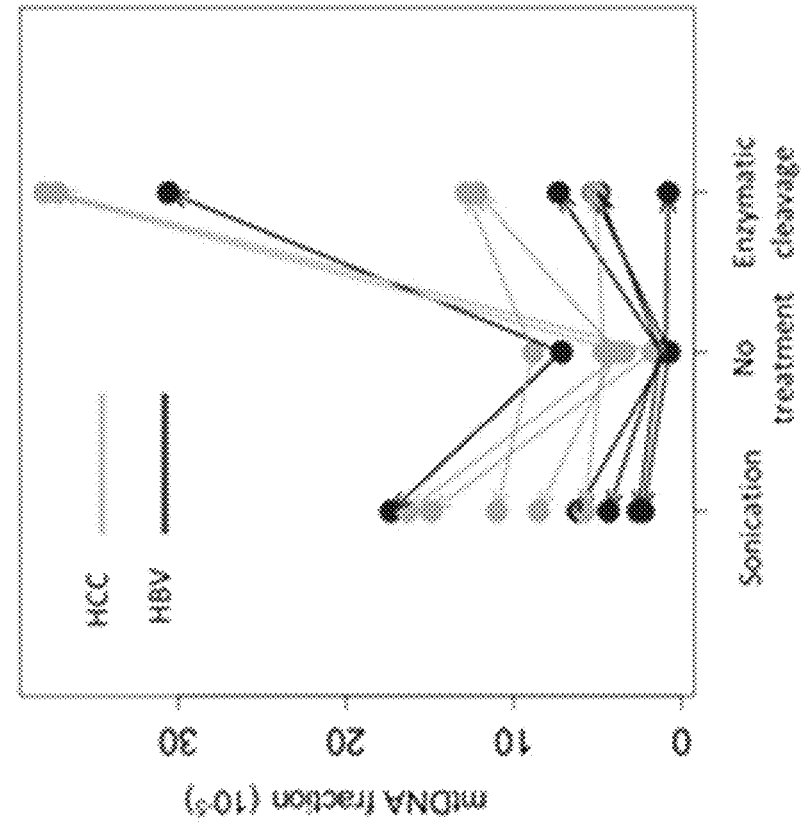

FIGS. 25A and 25B shows a comparison of plasma mtDNA metrics for plasma DNA of HBV and HCC samples with and without restriction enzyme digestion. FIG. 25A shows the proportion of mtDNA fragments in the total plasma DNA molecules. The total plasma DNA molecules include mtDNA molecules and nuclear DNA molecules. The different columns correspond to different aliquots of the same sample, where the left column corresponds to an aliquot where sonication-based shearing of plasma DNA was performed before sequencing (sonication), the center column corresponds to plasma DNA without enzymatic cleavage (no treatment), and the right column corresponds to plasma DNA subjected to restriction enzyme treatment (enzymatic cleavage). The lines connect the data points for the three aliquots.

FIG. 25B shows the proportion of mtDNA fragments with two enzymatically cleaved ends in the total plasma mtDNA molecules. The left column corresponds to a simulation of in silico cleavage on plasma DNA. The other columns are similar to FIG. 25A. The simulation was performed by in silico cutting of the mtDNA at BfaI enzyme recognition sites in plasma samples. This simulation retained linear DNA and thus mimicked results that did not reduce linear DNA, e.g., with exonuclease treatments. The enzymatic cleavage data did use such an enzyme treatment, thereby providing a baseline of mtDNA carrying two enzymatic cleaved ends in plasma DNA. In other words, the linear plasma DNA was subjected to further in silico cutting to determine the resulting size profile, illustrating how the linear fragments carrying one enzyme sites would affect the size profile.

Compared with the fraction of mtDNA of plasma DNA without the treatment of restriction enzyme (median: $2.5 \times 10^{-3}$%; range: $7.4 \times 10^{-4}$% to $8.8 \times 10^{-3}$%), the fraction of mtDNA of both plasma DNA samples treated with sonication prior to sequencing (median: $7.3 \times 10^{-3}$%; range: $2.3 \times 10^{-1}$% to 0.017%) and plasma DNA samples treated with enzymatic cleavage (median: $9.8 \times 10^{-3}$%; range: $7.8 \times 10^{-4}$% to 0.037%) was found to be significantly increased (p-value: 0.02 and 0.03, respectively) (FIG. 25A). Such an increase of mtDNA in plasma DNA samples after the shearing of the circular mtDNA molecules was observed in both HBV and HCC subjects.

As shown in FIG. 25B, the proportion of mtDNA fragments having two cleaved ends was greatly increased in plasma DNA samples with enzymatic cleavage (median: 75.1%; range: 2.3%-92.0%) in comparison with samples without restriction enzyme treatment (median: 0%; range: 0%-0.25%) (p-value: $4.4 \times 10^{-5}$) and simulation conditions (median: 14.0%; range: 11.6%-19.7%) (p-value: 0.0003).

On the other hand, HBV has a circular genome. Indeed, the enzymatic or sonicated shearing made HBV fragments more readily detectable in HCC patients who were positive for HBV infection (Table 7) compared with the condition of no treatment. These results suggested that physical shearing or enzymatic cleavage of plasma DNA would be a generic tool to assess the contribution of circular DNA present in a plasma DNA sample, even for subjects that have cancer or a viral infection, which may have a circular genome.

TABLE 7

The number of HBV DNA fragments detected across different library preparations.

| | | Numbers of HBV DNA fragments in plasma sample | | |
|---|---|---|---|---|
| Groups | Samples | No treatment | Sonication | Enzymatic cleavage |
| HBV | GM3001 | 0 | 0 | 0 |
| | GM3383 | 0 | 1 | 0 |
| | GM3405 | 0 | 2 | 1 |
| | GM3411 | 0 | 0 | 0 |
| | GM3428 | 0 | 0 | 0 |
| HCC | TBR1007 | 2 | 12 | 8 |
| | TBR1105 | 0 | 10 | 0 |
| | TBR1124 | 9 | 1146 | 778 |
| | TBR1258 | 0 | 4 | 4 |
| | TBR995 | 18 | 14520 | 6798 |

3. Tagmentation

As described above, transposases may also be used instead of restriction enzymes to perform the cutting of circular DNA.

Figure 26B:
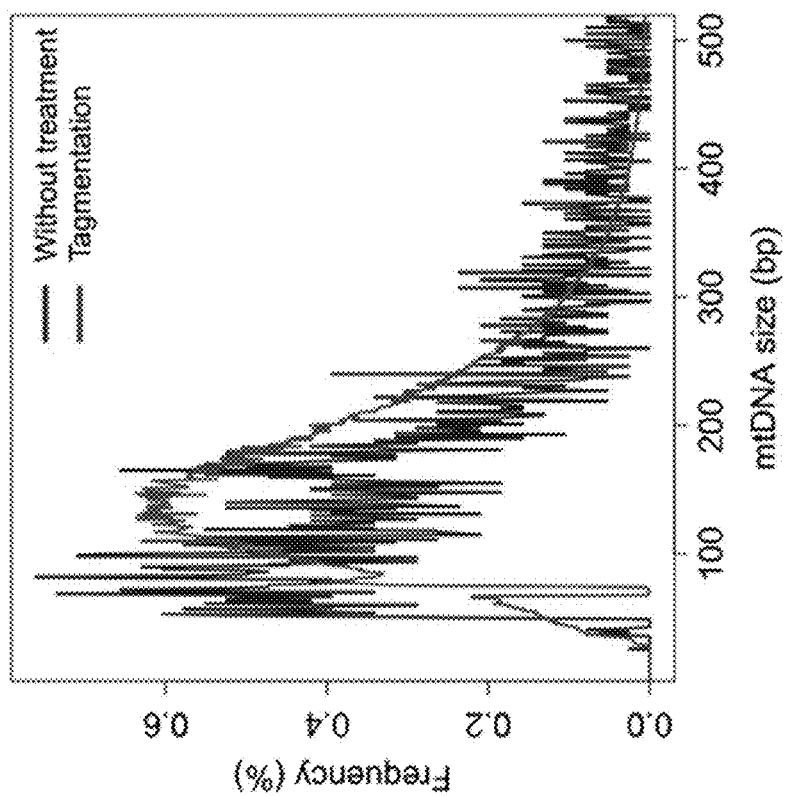
FIG. 26B shows a size profile of mtDNA fragments between samples with and without Tn5 tagmentation.
Figure 26A:
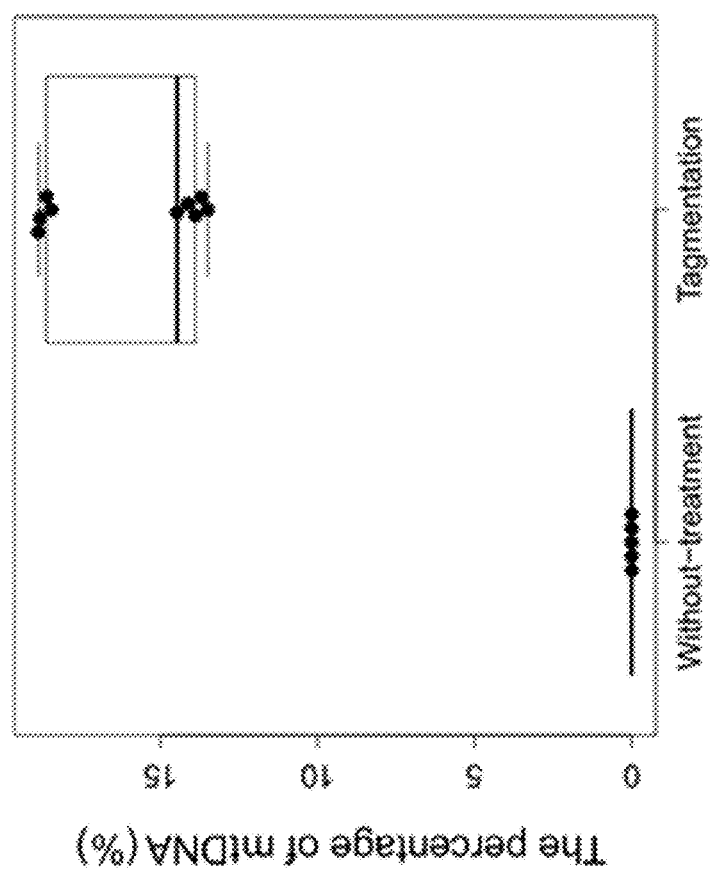
FIG. 26A shows the percentage of mtDNA between samples with and without Tn5 tagmentation.

FIG. 26A shows the percentage of mtDNA between samples with and without Tn5 tagmentation. FIG. 26A shows that the percentage of mtDNA in samples with Tn5 tagmentation (mean: 16.1%; range: 13.5-18.9%) is dramatically elevated compared with those without Tn5 tagmentation (mean: 0.0012%; range: 0.001-0.002%) (P-value=0.003). This data is consistent with the restriction enzyme data, illustrating that tagmentation can be used in a similar manner.

FIG. 26B shows a size profile of mtDNA fragments between samples with and without Tn5 tagmentation. FIG. 26B shows that the size profile of mtDNA molecules with Tn5 treatment has a peak to the right of the peak for the size profile of mtDNA molecules without Tn5 treatment, suggesting that there are more long mtDNA molecules present in mtDNA molecules with Tn5 treatment. Taken together, the increased quantity of mtDNA as well as the lengthening of mtDNA in samples with Tn5 tagmentation likely suggests that Tn5 opened up the circular mtDNA and made those linearized mtDNA molecules amenable to be sequenced.

C. Targeted Capture Assay and Molecular Barcode Strategy for Plasma mtDNA Analysis Even though the artificial shearing of plasma DNA could increase the proportion of mtDNA fragments in the plasma DNA pool, the mtDNA reads are still the minority in the total sequencing reads because of the much smaller size of the mitochondrial genome compared with that of the nuclear genome. It would be suboptimal to detect the nucleotide variants, including single nucleotide variants, small inserts/deletions, structural variations such as rearrangement, in mitochondrial genome (i.e. variant analysis) for cell-free mtDNA when the fractional concentration of such nucleotide variants is extremely low.

One embodiment to substantially improve the number of mtDNA in the sequencing result is to use target capture enrichment. Thus, we designed a set of hybridization probes targeting the mitochondrial genome.

Figure 27:
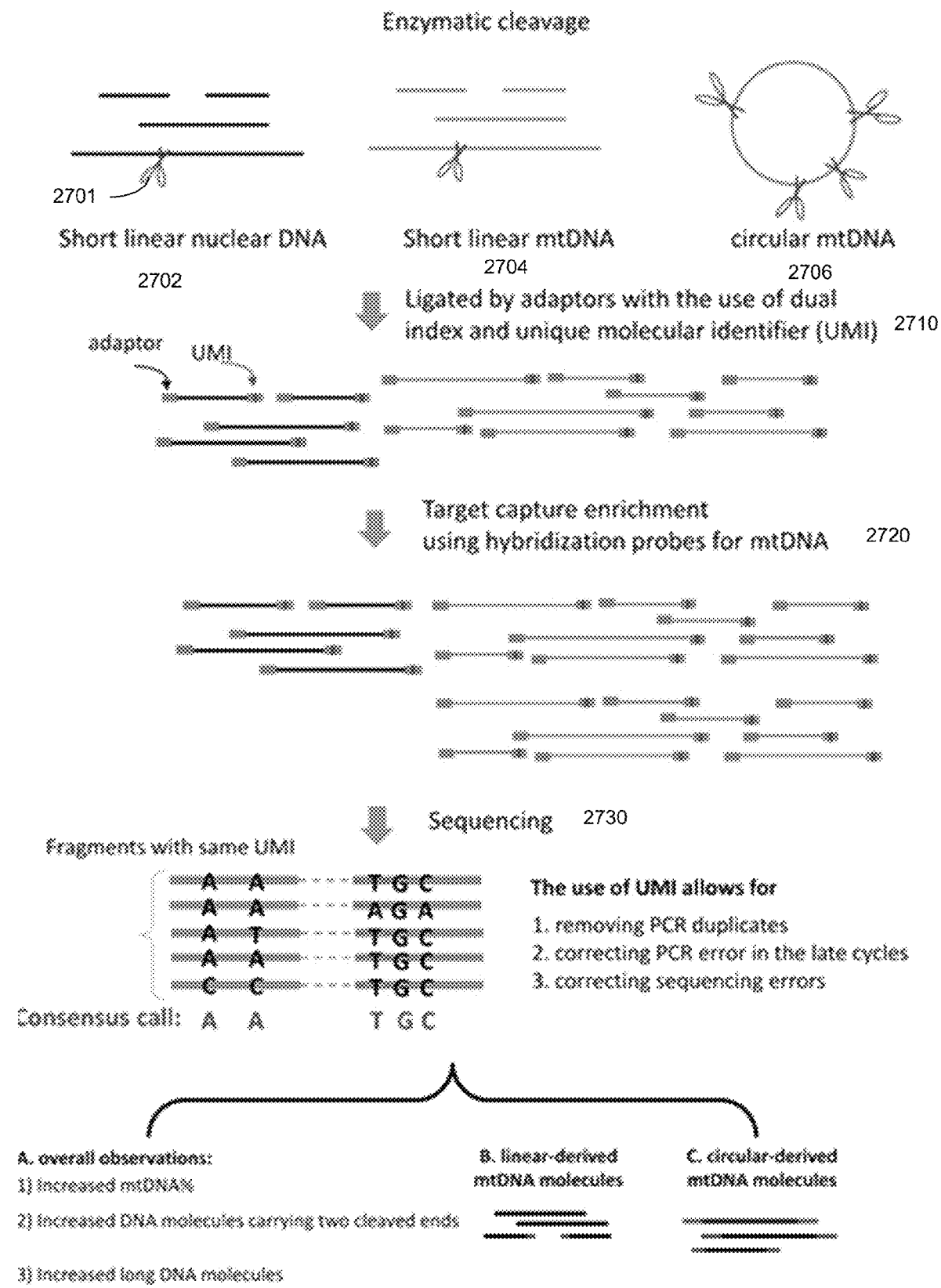
FIG. 27 shows targeted capture based TopM analysis according to embodiments of the present disclosure.

FIG. 27 shows targeted capture based TopM analysis according to embodiments of the present disclosure. Short linear nuclear DNA 2702, short linear mtDNA 2704, and circular mtDNA 2706 undergo enzymatic cleavage. Scissors 2701 (red) represent the restriction enzyme cutting sites.

At step 2710, adaptors and unique molecular identifiers (UMIs) can be ligated to the DNA molecules. Adaptors can be ligated to both ends for performing paired-end sequencing. The UMI may only be added to one of the ends, and may be part of an adaptor. Thus, the UMI may be a unique sequence of a specified number of bases that can differentiate the different molecules from each other.

At step 2720, target capture enrichment may be performed, e.g., using hybridization probes for mtDNA. In some implementations, after the probes hybridize to the mtDNA, the mtDNA can be amplified, e.g., using the probes or other primers. The amplification be performed using PCR or other suitable amplification procedure. In other implementations, the probes can just be used to capture the mtDNA, thereby increasing the mtDNA concentration in the sample. As shown, the number of mtDNA molecules is increased relative to the amount of nuclear DNA molecules.

At step 2730, sequencing is performed. A consensus sequence can be determined for each template DNA molecule using reads that have the same UMI, thereby indicating the reads originate from a same template molecule. The UMIs can be used to remove amplification (e.g., PCR) duplicates, correct errors in the late cycles of amplification, and correct sequencing errors. The consensus sequence can provide such corrections.

As shown in FIG. 27, an extra step of target capturing was introduced before sequencing so that the mtDNA abundance in the sequencing library would be greatly increased. By amplifying mitochondrial DNA in the cell-free DNA, a proportion of mtDNA molecules relative to nuclear DNA molecules is thereby increased. The number of DNA molecules carrying two cleaved ends is also increased, as well as the number of long DNA molecules, e.g., greater than 200 bases.

Another feature in the capturing design was to incorporate unique molecular identifiers (UMIs). Each DNA molecule before capturing would be tagged by an adaptor with a UMI. In the sequencing result, the sequenced fragments having the identical UMI would be deemed as PCR replicates. All the sequenced fragments carrying the same UMI were collapsed to form a single consensus sequence to represent the original molecule present in the plasma DNA pool. This process would allow us to remove PCR bias and minimize sequencing errors as well as PCR errors introduced in the late cycles. This approach would thus improve the accuracy of TopM analysis and making it suited for variant calling at an extremely low mutant fraction.

Accordingly, embodiments can attach molecular identifiers to the linearized mitochondrial DNA molecules and to the plurality of linear mitochondrial DNA molecules. A consensus sequence can be determined for a group of mitochondrial DNA molecules that have a same molecular identifier, and the consensus sequence can be used as a single sequence read for downstream analysis, e.g., as described in flowcharts below.

Figure 28:
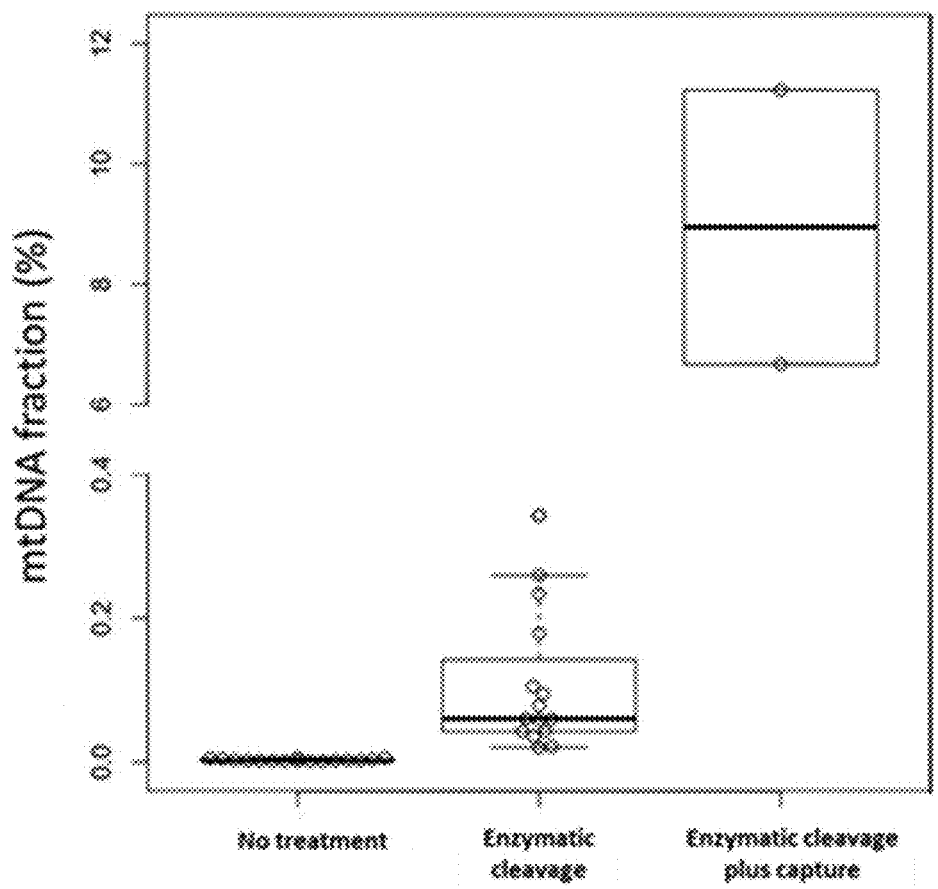
FIG. 28 shows that enzymatic cleavage plus target enrichment improves the detection of mtDNA fragments according to embodiments of the present disclosure.

FIG. 28 shows that enzymatic cleavage plus target enrichment improves the detection of mtDNA fragments according to embodiments of the present disclosure. As shown in FIG. 28, the target enrichment based TopM analysis indeed improved the detecting ability (i.e. 80 times more mtDNA than non-targeted version) of the mtDNA fragments.

D. Example of Liver Transplantation for Determining Level of Disease

Using a sex-mismatched transplantation model, Lo et al. demonstrated the presence of donor-specific DNA in the plasma of kidney and liver transplant recipients (Lo et al., Lancet. 1998; 2:1329-30). Liver transplantation is an attractive model for studying the biology of tissue-specific cell-free DNA molecules by making use of genetic signatures including single nucleotide polymorphism (SNP) differences. We applied targeted capture based TopM analysis to plasma DNA of patients who received liver transplantation.

Figure 29:
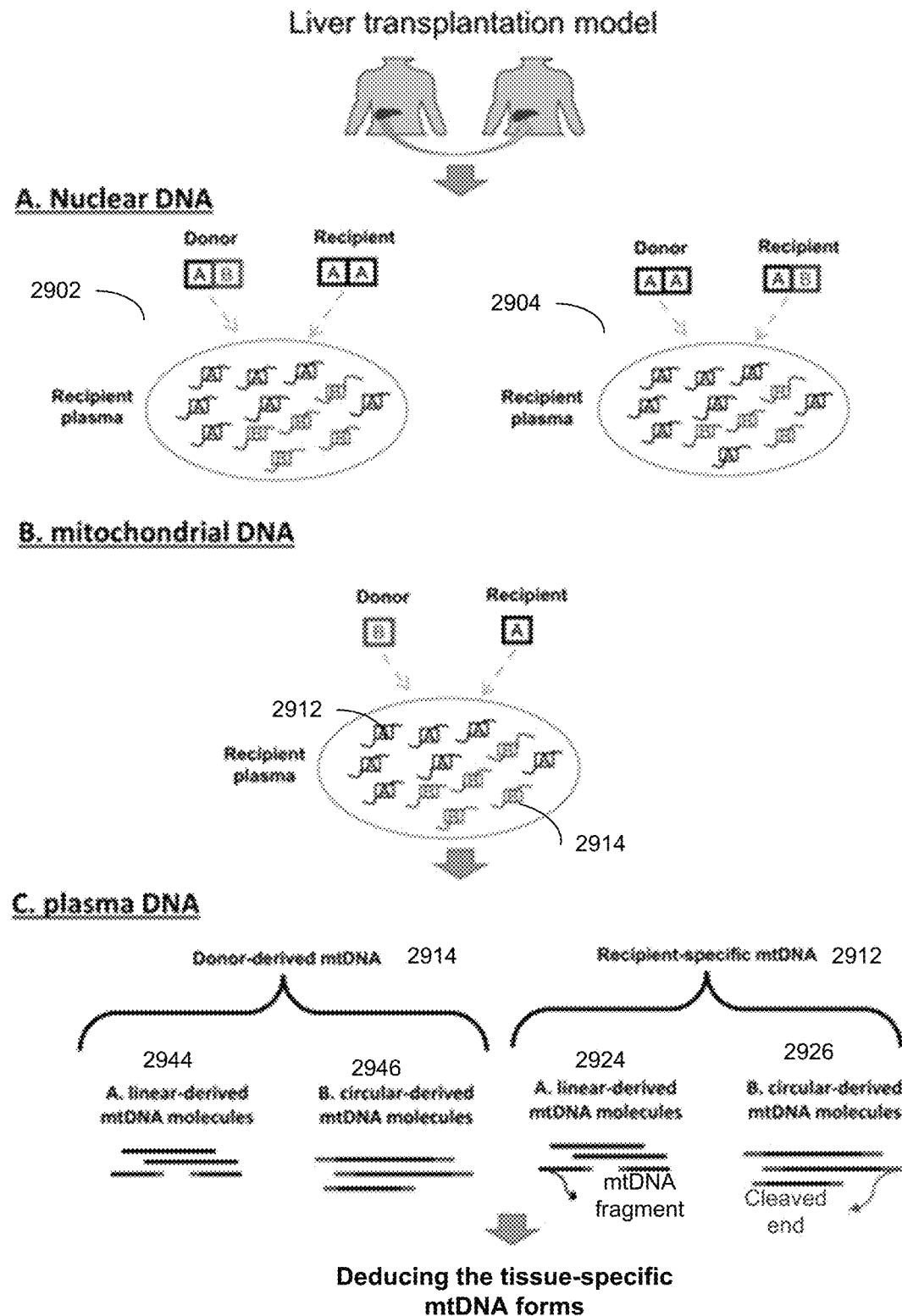
FIG. 29 shows an example technique illustrated using a liver transplant model for analyzing linear and circular mtDNA according to embodiments of the present disclosure.

FIG. 29 shows an example technique illustrated using a liver transplant model for analyzing linear and circular mtDNA according to embodiments of the present disclosure. A donor-specific allele can be used with certain measurements to confirm results, e.g., existence of circular mtDNA and accuracy of measurement. However, techniques for measuring linear and circular mtDNA may be used outside of the transplant application, such as for other diseases (e.g., cancer) besides transplant failure. Results show that subjects with an organ having a disorder/condition (including a transplanted organ) have a reduced amount of circular mtDNA relative to linear mtDNA compared to healthy controls due to increased cell death.

For the nuclear DNA and the mtDNA, "A" and "B" represent two different nucleotide variants. As shown in FIG. 29, for plasma nuclear DNA analysis, the liver DNA fraction in plasma could be deduced by using informative SNP sites for which the recipient was homozygous (AA) and the donor was heterozygous (AB), as shown for scenario 2902 and not scenario 2904. In scenario 2902, the liver DNA fraction could be defined as the proportion of plasma nuclear DNA bearing a donor-specific allele (B) times a constant factor of 2.

For plasma mtDNA analysis, we made use of the genomic sites in the mitochondrial genome where both the recipient and donor appeared to be homoplasmic (i.e., appeared to generally be the same) but they had different nucleotides at such genomic sites. The sites showing donor-specific and recipient-specific variants, being referred to as mitochondrial informative variants, would be of particular interest and importance. On the basis of plasma mtDNA fragments covering these mitochondrial informative variants, plasma mtDNA fragments could be divided into donor-specific mtDNA fragments 2914 and recipient-specific mtDNA fragments 2912. Donor-specific mtDNA fragments 2914 were further classified into circular-derived mtDNA 2946 and linear-derived mtDNA 2944 (i.e. spontaneously occurring linear DNA), depending on whether such a fragment carried two enzymatically cleaved ends or not. Similarly, recipient-specific mtDNA 2912 fragments were further classified into circular-derived mtDNA 2926 and linear-derived mtDNA 2924, depending on whether such a fragment carried two enzymatically cleaved ends or not.

In this analysis, we attempted to address the following points:
 a) the relative contribution of mtDNA from liver tissues and non-liver tissues (predominantly of hematopoietic origin).
 b) the relative quantity of linear-derived (fragment without cleaved ends or a single cleaved end) and circular-derived (two cleaved ends) for liver-derived DNA molecules and hematopoietically-derived DNA molecules.
 c) the use of plasma mtDNA mutations in the linear and circular forms could be used as biomarkers for cancer detection.

In some implementations for (c), linear mtDNA may be mainly derived from liver, e.g., if the liver has a tumor. Tumor cells disproportionately undergo apoptosis, which can cause the circular mtDNA to become linear, thereby enriching the linear DNA with tumor-derived DNA molecules. Circular mtDNA may be mainly derived from blood cells (perhaps related with aging).

As another example, circular mtDNA mutations can be used correct the background noise when the sample is plasma or serum. For instance, variants identified from circular mtDNA would be more likely associated with blood lineage cells. Thus, we can use these variants from circular mtDNA as baseline mutations. Any mutations not overlapped with those baseline mutations would increase the likelihood of being originated from other organs, e.g., one having a tumor, such as liver in this example. As yet another example, we can use circular mtDNA to filter the potential false positives (mutations derived from hematopoietic cells) or focus on those mutations only present in linear mtDNA but absent in circular mtDNA. Such implementation for (c) does not require a transplanted organ for the analysis.

As an example to test this model, we sequenced plasma DNA samples from two liver transplant subjects with the use of a median of 226 million paired-end reads (range: 130-267 million). In the capture design, we also designed hybridization probes targeting 1000 SNPs on autosomes for estimating the donor's DNA contribution in plasma DNA of the recipient. We prepared two aliquots of plasma DNA from each liver transplant subject. One aliquot of plasma DNA was used for target capture enrichment of mtDNA (without the treatment of restriction enzyme prior to capturing). The other aliquot of plasma DNA was used for enzymatic cleavage treatment followed by the target capture enrichment of mtDNA. DNA samples extracted from donor's archived formalin-fixed, paraffin-embedded (FFPE) liver tissues and the recipient's white blood cells were also subject to the enzymatic cleavage treatment followed by the target capture enrichment of mtDNA. Through sequencing the donor's and recipient's white blood cells, we obtained the genotypes in the nuclear DNA and also identified the mitochondrial informative variants. There were 563 and 297 informative SNPs (nuclear DNA) for the liver transplant cases TBR1453 and TBR1574, respectively. There were 41 and 29 mitochondrial informative variants for the liver transplant cases TBR1453 and TBR1574, respectively.

FIG. 30 shows a table 3000 illustrating statistics for liver transplant cases according to embodiments of the present disclosure. Capture indicates only target capture enrichment of mtDNA. Ez+capture indicates the enzymatic cleavage treatment followed by the target capture enrichment of mtDNA The liver DNA fraction (nuclear DNA) was found to be 38.9% and 15.8% for liver transplant cases TBR1453 and TBR1574, respectively. Notably, for plasma DNA samples treated with only target capture enrichment of mtDNA (labeled by "capture"), 94.5% and 87.47% of the mtDNA fragments were found to originate from the donor. As this process did not involve enzymatic cleavage, the results indicated that the liver was the predominant source shedding spontaneously linearized mtDNA fragments into plasma. Tumor cells would similarly be expected to be the predominant source shedding spontaneously linearized mtDNA fragments into plasma. On the other hand, because the circular mtDNA molecules were not likely to be sequenced by the Illumina sequencing protocol, we had not presented data for the circular forms of mitochondrial DNA in this analysis ("NA" in table 3000).

For plasma DNA samples treated with the enzymatic cleavage followed by the target capture enrichment of mtDNA, the proportion of mtDNA in the total plasma DNA molecules was found to be 3.63% for TBR1453 and 4.57% for TBR1574. These figures were higher than the matched plasma DNA samples without the enzymatic cleavage treatment (i.e. TBR1453: 1.52% and TBR1574: 0.49%). By enzymatically cutting plasma DNA for TBR1453, the recipient's mtDNA contribution dramatically increased up to 51.03% from the level of 5.5% in the matched sample without restriction enzyme treatment. These results indicated that a considerable proportion of circular mtDNA was of hematopoietic origin. A similar pattern was also observed in the liver transplant case TBR1574. The recipient's mtDNA contribution increased up to 80.50% from the level of 0.49% in the matched sample without restriction enzyme treatment. Taken together, we concluded that the majority of hematopoietically-derived mtDNA molecules were of the circular configuration, while the majority of spontaneously occurring linear mtDNA fragments in plasma were derived from the liver.

According to the principle shown in FIG. 29, we could further analyze the relative amounts of the linear and circular forms for the recipient's mtDNA and the donor's mtDNA by taking advantage of the presence of enzymatically cleaved ends.

FIGS. 31A and 31B show an analysis of linear and circular mtDNA molecules in the plasma of liver transplant cases according to embodiments of the present disclosure. For the recipient's mtDNA of case TBR1453, the linear and circular mtDNA fractions were 10.0% and 41.03%, respectively. For the donor's mtDNA of case TBR1453, the linear and circular mtDNA fractions were 47.54% and 1.43%, respectively. These results indicated that the majority of hematopoietically-derived mtDNA would be circular while the majority of liver-derived mtDNA would be linear. Again, the similar distribution in the amounts of linear and circular mtDNA was observed in the liver transplant case TBR1574. For the recipient's mtDNA of the liver transplant case TBR1574, the linear and circular mtDNA fractions were 29.37% and 51.13%, respectively. For the donor's mtDNA of the liver transplant case TBR1574, the linear and circular mtDNA fractions were 19.0% and 0.5%, respectively.

On the basis of these results, we hypothesize that the conventional whole-genome random sequencing would predominantly quantify the linear mtDNA, and the mtDNA fraction would be expected to correlate with liver DNA fraction. We analyzed plasma DNA samples from 14 liver transplant cases with a shallow sequencing depth (median: 21 million paired-end reads; range: 16-26 million). The liver contribution in the x-axis was quantified by the liver-specific methylation marker via droplet digital PCR (ddPCR) assay (Gai et al., Clin Chem. 2018; 64:1239-1249).

Figure 32:
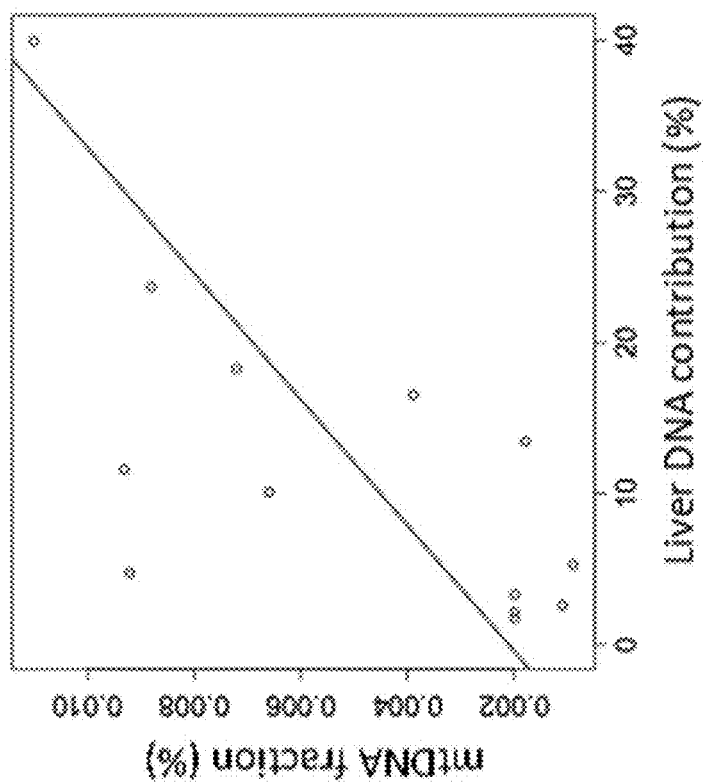
FIG. 32 shows the correlation of mtDNA fraction (determined by sequencing without enzyme treatment) and liver DNA fraction (determined by methylation analysis using ddPCR) according to embodiments of the present disclosure.

FIG. 32 shows the correlation of mtDNA fraction (determined by sequencing without enzyme treatment) and liver DNA fraction (determined by methylation analysis using ddPCR) according to embodiments of the present disclosure. The mtDNA fraction on the vertical axis is the percentage of all DNA, i.e., linear mtDNA and linear nuclear DNA. The liver DNA fraction on the horizontal axis is measured using liver-specific methylation markers (Gai et al., Clin Chem. 2018; 64:1239-1249) in linear nuclear DNA fragments. In one embodiment, the liver DNA fraction in patients with liver transplantation would be determined by the donor-specific alleles, e.g., as explained for FIG. 29. Indeed, the mtDNA fraction correlated with liver DNA contribution (FIG. 32, r=0.7, p-value=0.005). Thus, the linear mtDNA abundance can be used for reflecting the liver DNA contribution (or other transplanted or diseased organ) to the plasma DNA pool in a noninvasive way.

As cell death phenomena (e.g. apoptosis and necrosis) have been postulated to be a key mechanism for the release of plasma DNA, the concentration (relative or absolute concentrations) of linear mtDNA in plasma would represent a rapid method for monitoring liver cell death, which would be related to a number of disorders, e.g. cancer (such as hepatocellular carcinoma or liver metastases from cancer originated from other sites), inflammation (e.g. hepatitis due to viral (such as HBV or hepatitis C virus) or non-viral (such as alcohol-related or fatty liver diseases or autoimmune or drug related (such as paracetamol)) causes) or cirrhosis). The higher the amount of linear mtDNA in plasma DNA, the higher degree of severity in liver cell death would be, and the lower the amount of circular mtDNA. While the data shown here were presented as a percentage, the amount of linear and circular mtDNA can be provided in various ways. For example, one could convert such a percentage value into an absolute concentration (e.g. ng per ml) by multiplying the total concentration of plasma DNA. Such analysis of relative abundance between linear mtDNA and circular mtDNA to determine a level of disease/condition/disorder can be used for such detection in other organs as well, as such organs experiencing cell death will have similar behavior.

In some embodiments, the proportion of circular mtDNA would reflect the other organ DNA damage. Because the proportion of circular mtDNA was mainly derived from hematopoietic cells, the reduction of the proportion of circular mtDNA would indicate the release of some other organ's DNA into the plasma DNA.

FIG. 33 shows the difference in the quantity of linear and circular mtDNA between healthy controls and liver transplant patients according to embodiments of the present disclosure. As shown in table 3300, the percentage of mtDNA with two cleaved ends (i.e. circular mtDNA) in liver transplant patients (52%) was shown to be lower than that in healthy controls (73%). In addition, the linear mtDNA in liver transplant patients was higher than that of healthy controls. These results suggested that an increased liver DNA damage, leading to the release of more liver-derived DNA into blood circulation. Such a dynamic tracing of linear and circular mtDNA molecules in plasma DNA might allow us to assess the health status of a patient including organ rejection, inflammation, metabolic changes or disorders, immune related damage, oncology and so on.

E. Linearity and Circularity of mtDNA in HCC Patients and Non-HCC Subjects

We tested the diagnostic potential of a relative abundance of linear and circular mtDNA in differentiating HCC patients from non-HCC subjects. In these example experiments, we used enzymatic cleavage followed by a target enrichment protocol, although other techniques may be used, e.g., non-target enrichment or cleavage using transposases or other cleaving techniques. We sequenced 5 plasma DNA samples from HCC patients and 5 plasma DNA samples from HBV carriers with a median of 28.6 million sequenced fragments (range: 14.1-57.1 million). The median depth of the mitochondrial genome was 2,690× (range: 1,018-5,336×), which was on average 5 times higher than the sequenced results without enzymatic cleavage (median: 512×; range: 243-3,022×). The plasma mtDNA molecules without enzymatically cleaved ends were deemed as linear mtDNA while the plasma DNA molecules with two enzymatically cleaved ends were deemed as circular mtDNA. Those mtDNA with one cleaved end were also regarded as the linear mtDNA derived from a fragment carrying an enzymic recognition site or those carrying one cleaved end at DNA ends by chance.

Figure 34:
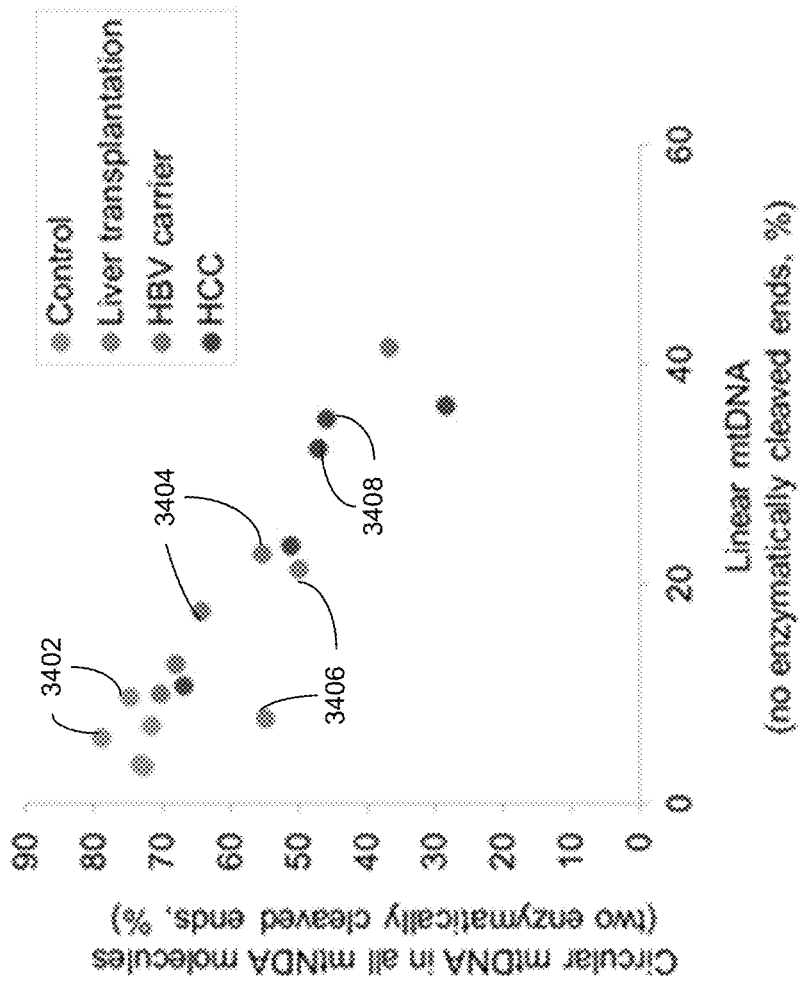
FIG. 34 shows the proportion of linear and circular mtDNA molecules among all mtDNA molecules according to embodiments of the present disclosure.

FIG. 34 shows the proportion of linear and circular mtDNA molecules among all mtDNA molecules according to embodiments of the present disclosure. The vertical axis is the percentage of circular mtDNA molecules (determined as two enzymatically cleaved ends) out of all mtDNA molecules. The horizontal axis is the percentage of linear DNA (determined as no enzymatically cleaved ends). The data points correspond to these two values. Different classifications of subjects are marked in different colors: healthy controls 3402 are light green, liver transplantation 3406 are dark green, HBV carriers 3404 are blue, and HCC subjects 3408 are red.

As shown in FIG. 34, the proportion of linear mtDNA was found to be significantly higher (p-value: 0.03) in plasma DNA of HCC patients (mean: 27.49%; range: 10.64-36.18%) than that in plasma DNA of non-HCC patients including healthy controls, liver transplant cases and HBV carriers (mean: 13.53%; range: 3.28-41.52%). In contrast, the proportion of circular mtDNA was found to be lower in the plasma DNA of HCC patients (mean: 47.99%; range: 28.46-66.96%) than that in the plasma DNA of non-HCC patients, including healthy controls, liver transplant cases and HBV carriers (mean: 64.33%; range: 36.89-79.02%). Combined analysis of circular and linear mtDNA as shown in FIG. 34 allow differentiating HCC from non-HCC subjects. The sensitivity and specificity were 80% and 92%, respectively, if we used below criteria as a determination of cancer:

a. circular mtDNA %<50% (where 50% is an example of a cutoff);

b. linear mtDNA %>21% (where 21% is an example of a cutoff).

Figure 35A:
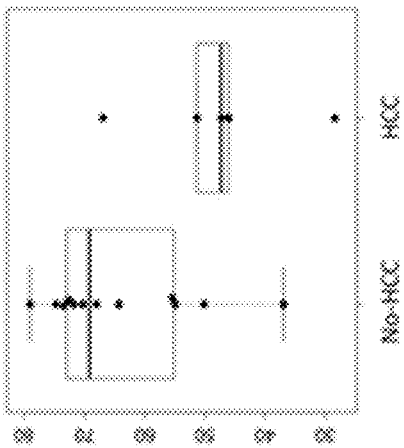
FIGS. 35A-35C show the difference between HCC and non-HCC subjects for the percentage of mtDNA in all molecules (35A), linear mtDNA in all mtDNA molecules (35B), and circular mtDNA in all mtDNA molecules (35C).
Figure 35B:
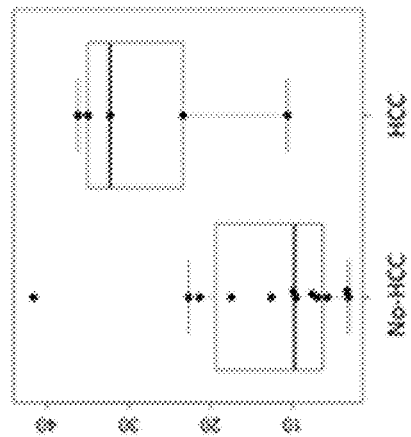
Figure 35C:
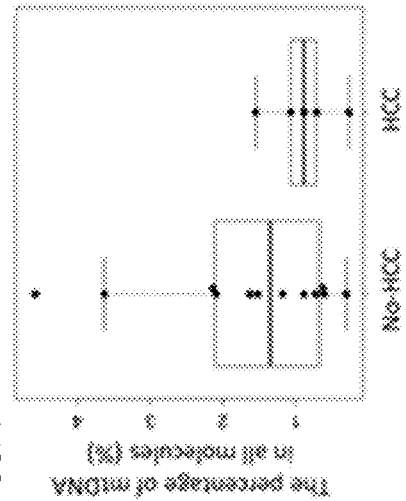

FIGS. 35A-35C show the difference between HCC and non-HCC subjects for the percentage of mtDNA in all molecules (35A), linear mtDNA in all mtDNA molecules (35B), and circular mtDNA in all mtDNA molecules (35C). Cleavage techniques (e.g., using restriction enzyme or transposase) were used in all three plots. FIG. 35A shows poor discrimination between no-HCC and HCC using the percentage of all mtDNA among all DNA molecules.

However, the percentage of linear or circular mtDNA among mtDNA molecules provides good discrimination. FIG. 35B shows the percentage of linear mtDNA (determined as no enzymatically cleaved ends) among all mtDNA (i.e., linear and circular) for no-HCC and HCC subjects. Such values use the determination of circular DNA so that the percentage can be determined among all mtDNA. FIG. 35B shows the percentage of circular mtDNA (determined as no enzymatically cleaved ends) among all mtDNA (i.e., linear and circular) for no-HCC and HCC subjects.

F. Pregnancy

The analytical approach for differentiating the linear-derived or circular-derived mtDNA molecules in plasma could be applied to pregnancies, besides just instances of organ disorders. To illustrate the concepts involved, we used a pregnancy model involving surrogacy. Surrogacy is a form of assisted reproductive treatment (ART) in which a woman carries a child within her uterus on behalf of another person. If one obtains the egg donor's and surrogate mother's white blood cells, we could genotype nuclear DNA and mtDNA for the egg donor and the surrogate mother.

Figure 36:
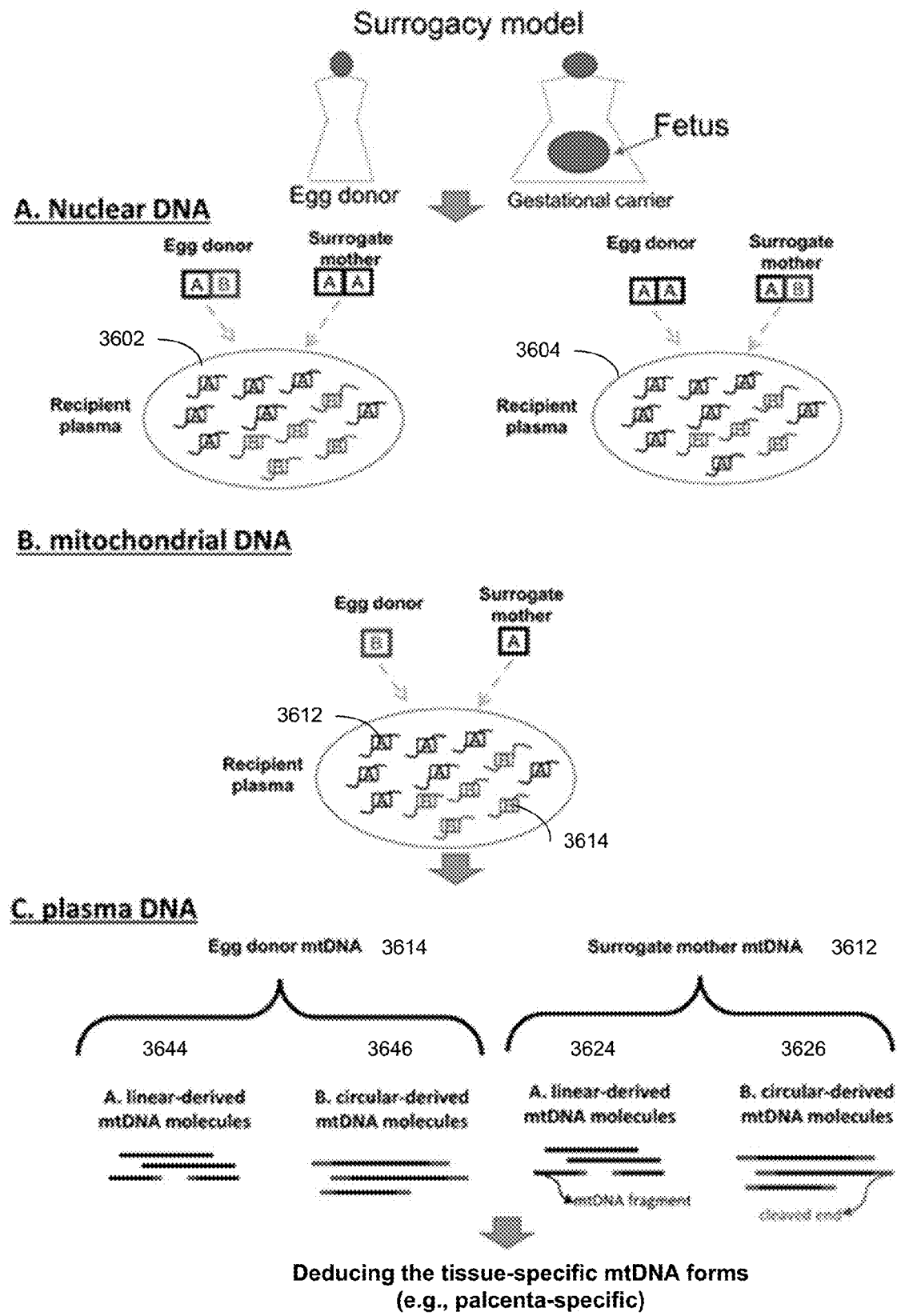
FIG. 36 shows an example technique using a surrogacy model for analyzing linear and circular mtDNA according to embodiments of the present disclosure.

FIG. 36 shows an example technique using a surrogacy model for analyzing linear and circular mtDNA according to embodiments of the present disclosure. A donor-specific allele can be used with certain measurements to confirm results, e.g., existence of circular mtDNA and accuracy of measurements. However, techniques for measuring linear and circular mtDNA may be used outside of the transplant application, such as for fetal diseases. For example, a fetus having a disorder/condition would have a reduced amount of circular mtDNA relative to linear mtDNA compared to healthy controls due to increased cell death.

For the nuclear DNA and the mtDNA, "A" and "B" represent two different nucleotide variants. As shown in FIG. 36, using such genotypic information, we can infer the fetal DNA fraction making use of nuclear plasma DNA and nuclear DNA genotype information of the egg donor and the surrogate mother, as shown for scenario 3602 but not for scenario 3604. On the other hand, by making use of the egg donor specific variants in mtDNA, we could further detect the egg donor associated mtDNA molecules 3614 carrying such specific variants, representing the placental/fetal mtDNA because mtDNA is inherited from the biological mother. Similarly, we can also further detect the surrogate mother-specific mtDNA molecules 3612 using those mtDNA fragments covering the surrogate mother-specific variants in the mtDNA.

According to whether both ends of an mtDNA fragment carry restriction enzyme cutting ends or not, the circular-derived molecules 3626 and 3646 and linear-derived mtDNA molecules 3624 and 3644 could be identified. TopM would allow us to reveal the form of mtDNA in the plasma DNA of pregnant women and deduce its relative proportions, which could not be achieved before. Such techniques can be useful for monitoring pregnancy-associated disorders if such mitochondrial disorders would alter the relative proportion of linear and circular mtDNA molecules. We would predict that spontaneously occurring linear mtDNA (e.g., due to cell death) derived from the placental tissues would add to the population of linear mtDNA (e.g., derived from the liver and other organs) of a pregnant surrogate female subject. A problematic surrogacy would have relatively high amounts of linear mtDNA (relative to circular mtDNA) compared to a healthy surrogacy. For example, a ratio of linear mtDNA to circular mtDNA can be compared to a cutoff value that discriminates between healthy and problematic pregnancies.

In a similar manner, the detection of fetal mitochondrial DNA in the plasma of pregnant women would also be useful for monitoring the success of mitochondrial gene therapy or mitochondrial replacement therapy (Zhang et al. Reprod Biomed Online 2017; 34: 361-368). An elevated level in the linear mtDNA relative to circular mtDNA can reflect problems in such therapy. Since fetal derived mtDNA in maternal plasma is mainly linear, the linear mtDNA could be monitored to reflect the fetal mtDNA status. This could be done as part of mutation loading, which is described below.

In various embodiments, a ratio of linear to circular mtDNA molecules can be used to detect changes in amounts of fetal mitochondrial DNA using a ratio of linear mtDNA to circular mtDNA as a proxy, monitor the success of a surrogate pregnancy (e.g. as mentioned above), or monitor the success of mitochondrial gene therapy or mitochondrial replacement therapy.

G. Variant Analysis

Figure 37:
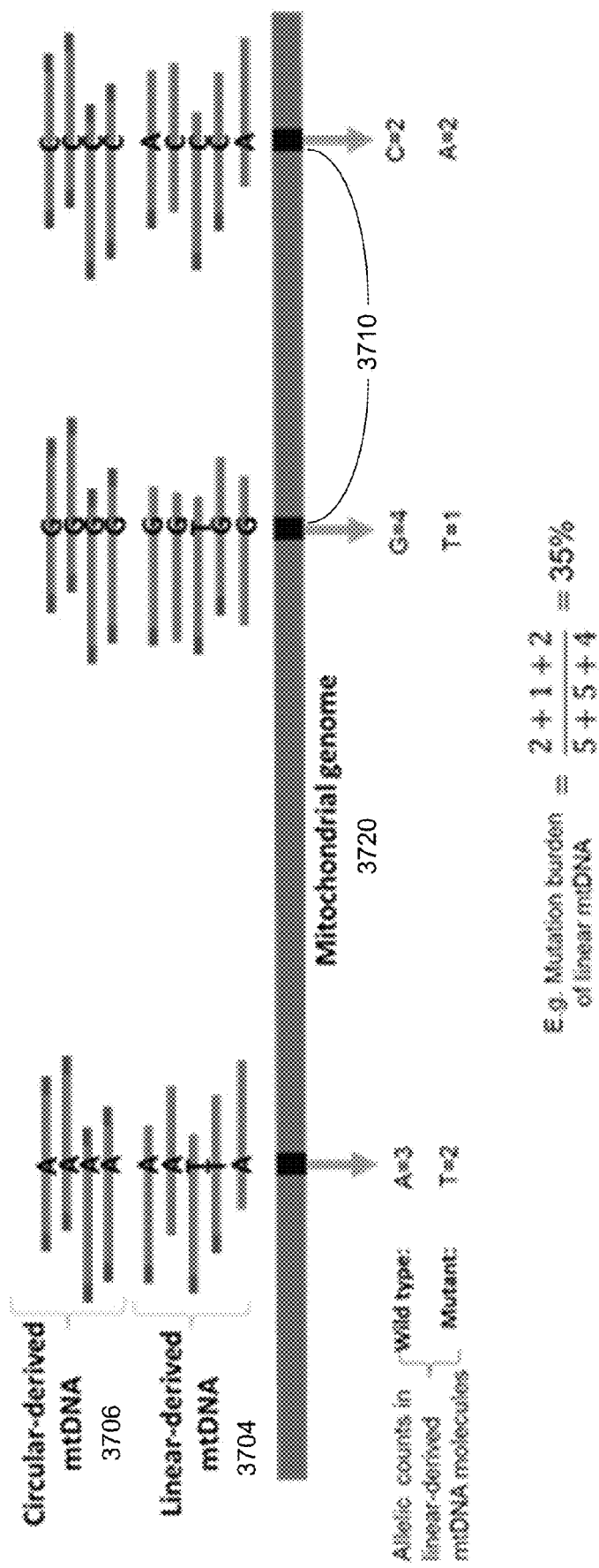
FIG. 37 shows an example of mutation burden calculation for linear mtDNA molecules according to embodiments of the present disclosure.

The mtDNA analysis for liver transplantation model revealed that the linear and circular mtDNA molecules can have markers (e.g., donor-specific alleles) for the different tissue of origin, and that linear and circular mtDNA molecules more likely to come from diseased and healthy tissue, respectively. Therefore, the mtDNA variant identification on linear mtDNA and circular mtDNA can reveal the variants associated with different tissues. For example, the variants identified from linear mtDNA would be more likely associated with liver cells or other diseased cells (e.g. for detection and/or monitoring of liver cancers, or disorders involving hepatocytes) whereas the variants identified from circular mtDNA would be more likely associated with blood lineage cells, which are predominant in plasma or serum (e.g. for assessing clonal hematopoiesis associated with aging (Greaves et al. PLoS Genet. 2014; 10:e1004620;). Particular variants in linear mtDNA (or the amounts of variants) can be used to identify an existence of diseased tissue FIG. 37 shows an example of mutation burden calculation for linear mtDNA molecules according to embodiments of the present disclosure. As shown, there were loci 3710 in the mitochondrial genome 3720 across which variants were present in linear-derived mtDNA 3704 but absent in circular-derived mtDNA 3706. Accordingly, the variants occurred at a different rate in linear-derived mtDNA 3704 compared to circular-derived mtDNA 3706. In other instances, variants may occur in circular-derived mtDNA 3706 at a higher rate than in linear-derived mtDNA 3704.

A rate of variants in linear-derived mtDNA 3704 can reflect the mutation burden from the diseased tissue (e.g., liver in examples above) because the diseased tissue mainly released mtDNA in a linear form. In this example, the mutation burden was defined by the total number of reads carrying variants divided by the total number of linear mtDNA being analyzed. As shown in FIG. 37, variants present in linear mtDNA but absent in circular-derived mtDNA were able to be identified by analyzing the loci that had a lower variant rate in circular-derived mtDNA 3706. In this particular example, the variant rate was zero, i.e., homozygous (all the same allele) in circular-derived mtDNA 3706. Accordingly, the mutation burden can be restricted to loci where the circular-derived mtDNA 3706 are homozygous. But, the variant rate does not need to be zero for circular-derived mtDNA 3706.

The unique variants present in linear mtDNA in comparison with the circular mtDNA would reflect the de novo variants or tissue-specific haplogroups of mtDNA (Grandhi et al, Hum Mol Genet. 2017; 26:2912-2922; Samuels et al, PLoS Genet. 2013; 9:e1003929). The term 'haplotype' can refer to mutations occurring in one mtDNA genome. The different mutations in different haplotypes can occur in the same circular mitochondrial genome or among different circular mitochondrial genomes. The combination of mutations in a circular mitochondrial genome may reflect the tissue specificity. Embodiments thus open up new possibilities for cell-free mtDNA based molecular diagnostics applications by being able to identify mutations in linear mtDNA fragments from diseased tissue.

The variants in the linear mtDNA would typically be of non-hematopoietic origin since the majority of spontaneously occurring linear mtDNA fragments in plasma is from non-hematopoietic tissue. If the variants occurred in circular-derived mtDNA 3706, then it can be determined that hematopoietic tissue include the variant. In either case, the number of loci having a variant or the number of sequence reads having a variant can be used to determine a mutational load. The mutation load can be compared to a threshold to determine if a disease (e.g., cancer) is present. In some implementations, only loci with one than N (e.g., 1, 2, 3, etc.) variant reads are used to determine the mutational load, e.g., so as to avoid instances of sequencing error. Then, whether the linear or circular mtDNA has the variants can be used to determine whether the disease has a non-hematopoietic origin or hematopoietic origin. Further, tissue specific variants in a biological sample could be used to deduce the mtDNA origin.

In some embodiments, TopM analysis would be useful for monitoring immune or auto-immune reactions of mitochondrial transplantation (e.g. the transplantation of autogeneic mitochondria for the amelioration of myonecrosis (Masuzawa et al, Am J Physiol Heart Circ Physiol. 2013; 304: H966-82)). For example, myonecrosis would release more mtDNA from muscle tissues, leading to the increase of mtDNA in plasma DNA. The specific pattern would be that the relative amount of linear DNA would increase and relative amount circular DNA would decrease. For a variant analysis, the muscle-specific mtDNA variants would increase in plasma DNA. Such analysis would apply to other tissues.

In the context of studying cell-free molecules, tracing the dynamics regarding the relative ratio between linear and circular mtDNA molecules and mutation profiles in linear and circular mtDNA molecules, as well as the differential mutation profiles between linear and circular mtDNA molecules would provide a new diagnostic avenue for mitochondria associated diseases including but not limited to cancers, autoimmunology, myonecrosis, cardioprotection, organ damage, and aging.

H. Methods of Using Circular mtDNA and Linear mtDNA

Measurements of circular mtDNA and linear mtDNA can be used for various purposes. For example, existence of diseased tissue can be identified from elevated amounts of linear mtDNA relative to circular mtDNA. As another example, sequence variants predominantly appearing in linear mtDNA or circular mtDNA can be used identify sequence variants in non-hematopoietic tissue or hematopoietic tissue. Various preparation protocols can be used, e.g., as described for FIGS. 17 and 27.

1. Determining a Level of Disease

Measurements of relative amounts of circular mtDNA and linear mtDNA can be used for various purposes, e.g., as described above. For example, diseased tissue would release more linear mtDNA due to increased cell death, thereby causing a parameter including a ratio of linear mtDNA to circular mtDNA to increase/decrease (depending on formulation of the parameter) relative to a subject that does not have diseased tissue. In contrast, circular mtDNA generally result from blood cells, and thus would occur at a relatively constant background rate. Such diseased tissue can include, as examples, transplanted organs, cancer, and inflammation, as well as others described herein. In some embodiments, if the amount of circular DNA is elevated, blood cells can be identified as being diseased.

Figure 38:
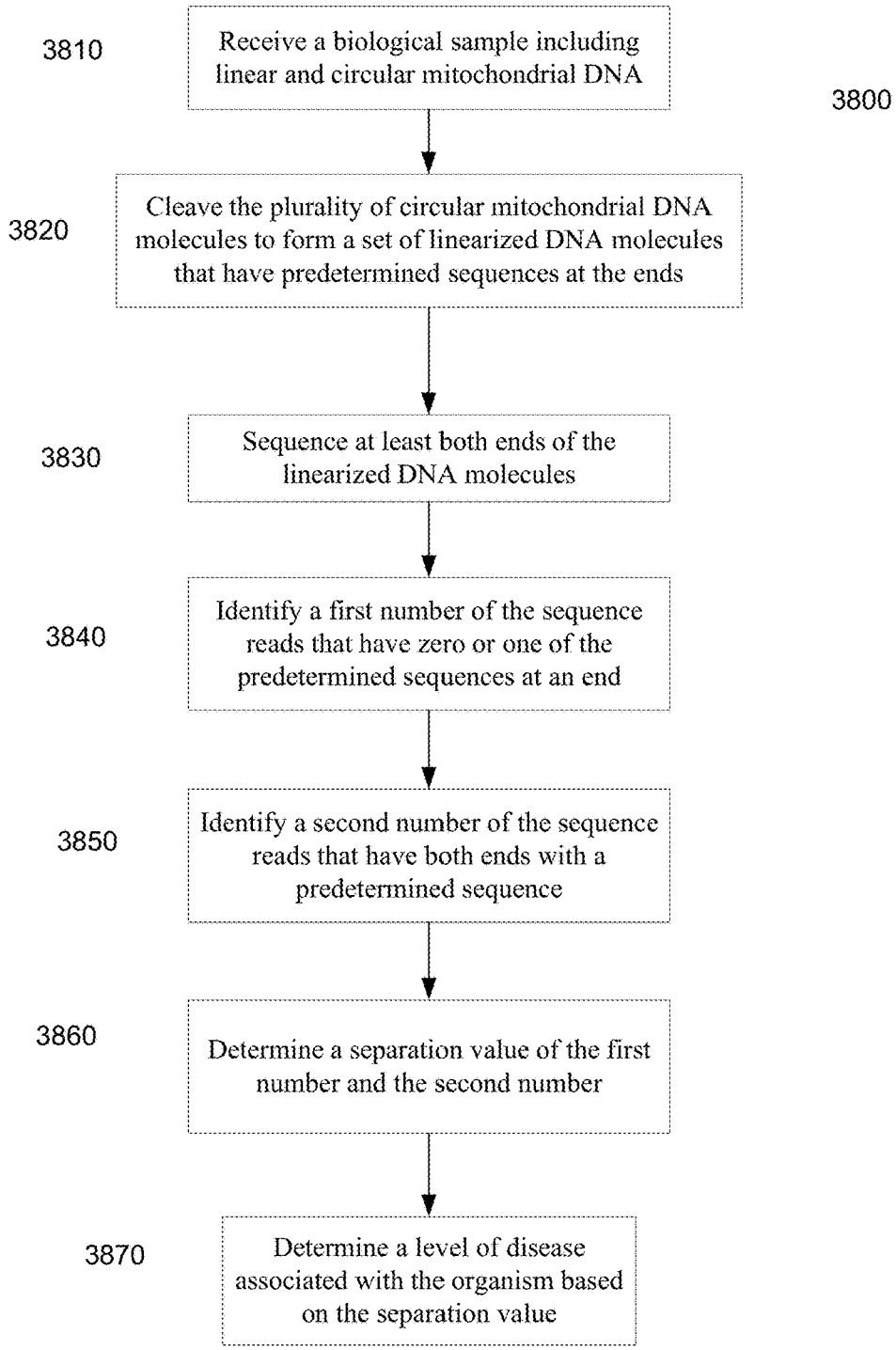
FIG. 38 is a flowchart illustrating a method 3800 for analyzing circular mitochondrial DNA (mtDNA) and linear mtDNA according to embodiments of the present disclosure.

FIG. 38 is a flowchart illustrating a method 3800 for analyzing circular mitochondrial DNA (mtDNA) and linear mtDNA according to embodiments of the present disclosure. Method 3800 can determine a level of disease from the analysis. As with other methods, physical steps may be performed using machinery (e.g., robotics) that is controlled by a computer system. In some implementations, circular mtDNA can be analyzed at the same time as linear mtDNA. Method 3800 can identify circular nuclear DNA according to one or more criteria and use a relative abundance of circular DNA relative to linear mtDNA in determining the level of disease.

At block 3810, a biological sample of an organism is received. The biological sample includes cell-free DNA, which includes linear mitochondrial DNA and circular mitochondrial DNA. The biological sample may be purified, e.g., to separate out a predominantly cell-free portion, such as plasma. Other pre-processing steps may be performed as well.

At block 3820, a plurality of the circular mitochondrial DNA molecules are cleaved to form a set of linearized mitochondrial DNA molecules that have predetermined sequences at the ends. The circular mitochondrial DNA molecules may be intact, and thus include the entire mitochondrial genome. In other instances, the circular mitochondrial DNA molecules may be only part of the mitochondrial genome, and thus have a junction, e.g., as described for nuclear DNA in section I.

As described herein, the cleaving can be performed in various ways, e.g., using restriction enzymes or transposases in combination with adapter sequences. The restriction enzyme can preferably cut DNA at a particular motif, resulting in linearized DNA molecules having predetermined sequences at the end. When using a transposase, after cleaving the plurality of eccDNA molecules, adapter sequences can be attached to both cleaved ends of each of the plurality of eccDNA molecules, thereby forming the set of linearized DNA molecules that have predetermined sequences (adapter sequence) at the end.

At block 3830, at least both ends of the set of the linearized DNA molecules and of a plurality of linear mitochondrial DNA molecules are sequenced to obtain sequence reads. For paired-end sequencing, two reads can be obtained: one for each end of a DNA molecule. For single molecule sequencing, the sequence read can be for the entire DNA molecule. The distinction between which molecules are linear or linearized (i.e., initially circular) can be determined by identifying whether predetermined sequences (e.g., a cutting tag) are at the ends of the DNA molecule.

The sequence reads corresponding to mtDNA can be identified by alignment to a reference mitochondrial genome, e.g., so as to distinguish from nuclear DNA. The alignment can be performed in stages (e.g., initially identifying ones that align to the reference mitochondrial genome), and then determining whether that subset aligns to a reference nuclear genome. As described above, those reads aligned to multiple regions or to both nuclear and mitochondrial genomes with the same mapping quality can be discarded.

At block 3840, a first number of the sequence reads that have zero or one of the predetermined sequences at an end are identified. In some embodiments, any one of the criteria of zero or one of the predetermined sequences at an end can be used. For example, only the number of sequence reads that have zero of the predetermined sequences at an end can be counted to determine the first number. As another example, only the number of sequence reads that have one of the predetermined sequences at an end can be counted to determine the first number. In yet another example, the two numbers can be summed to obtain a total number of sequence reads that match either criteria. Such sequence reads can be identified as corresponding to linear mtDNA At block 3850, a second number of the sequence reads that have both ends with a predetermined sequence are identified. As described in FIGS. 27, 29, and 36, linearized DNA molecules would have the predetermined sequences (e.g., as a result of restriction enzymes or transposases) at both ends. Accordingly, the second number of the sequence reads can be identified as corresponding to circular mtDNA.

At block 3860, a separation value (e.g., a ratio) between the first number and the second number is determined. Various separation values may be used, e.g., a percentage of the mtDNA fragments that are from a linear mtDNA molecule or a percentage that are from circular mtDNA. As further examples, the separation value may be the first number divided by the second number, or the second number divided by the first number. Accordingly, the separation ratio value can include a ratio of the first number and the second number.

At block 3870, a level of disease associated with the organism is determined based on the ratio. The level can be considered a classification as described herein. The level of disease may be a level of cancer, e.g., where the organism is being screened for cancer. The level of disease may be of a particular organ, e.g., the liver. For instance, the level of disease of the liver is determined to be cancer, HBV, or no disease. In another example, the level of disease is whether a transplanted organ is being rejected.

In another example, the organism is a female pregnant with a fetus, where the level of disease is of the fetus or of the pregnancy. If the fetus has a disease, the increased cell death in the fetus would increase the number of linear mtDNA molecules. An example disease is Kearns Sayre syndrome, which is a rare inborn error of metabolism that is characterized by progressive external ophthalmoplegia (PEO), pigmentary retinitis and an onset before the age of 20 years. Common additional features include deafness, cerebellar ataxia and heart block. Another example is maternally inherited diabetes and deafness (MIDD). Such diseases are mainly caused by mutations in a mitochondrial genome.

Determining the level of disease can include comparing the ratio to a reference value and determining the level of disease based on the comparison. The reference value can be determined based on cohorts of subjects that have a known level of the diseased, e.g., as shown in FIGS. 34 and 35. The reference value (e.g., a cutoff value) can be selected to optimize a specificity and sensitivity to predicting the level of disease. Thus, the reference value can be determining using a training set of samples that all have the disease, do not have the disease, or a combination of both. Accordingly, the reference value can be determined based on reference separation values determined from samples of subjects having a known level of disease.

Block 3870 can be performed using other feature(s) besides the separation value between the first number and the second number. For example, multiple separation values can be used. As mentioned above, the first number can be defined in various ways, e.g., depending on the number of predetermined sequences at an end. One separation value can be determined where the first number is defined using zero predetermined sequences. A second separation value can be determined where a third number is defined using zero predetermined sequences, where the separation value is determined between the second number and the first number. The feature(s) can be used to train a machine learning model.

2. Detecting Mutations in mtDNA from Non-Hematopoietic Tissue

Measurements of sequence variants in circular mtDNA and linear mtDNA can be used for various purposes, e.g., as described above. For example, sequence variants predominantly appearing in linear mtDNA or circular mtDNA can be used identify sequence variants in non-hematopoietic tissue or hematopoietic tissue, respectively. Such information can be used in various ways. For instance, a non-hematopoietic tumor can have more mutations in linear mtDNA than occur in healthy cells, and such a non-hematopoietic tumor would contribute predominantly linear mtDNA to plasma relative to circular mtDNA. Thus, if the number of sequence variants in linear mtDNA is above a threshold (e.g., indicating cancer), then the tumor can be identified as being non-hematopoietic tissue. And, if the number of sequence variants in circular mtDNA is above a threshold, the tumor can be determined to be of hematopoietic origin.

Figure 39:
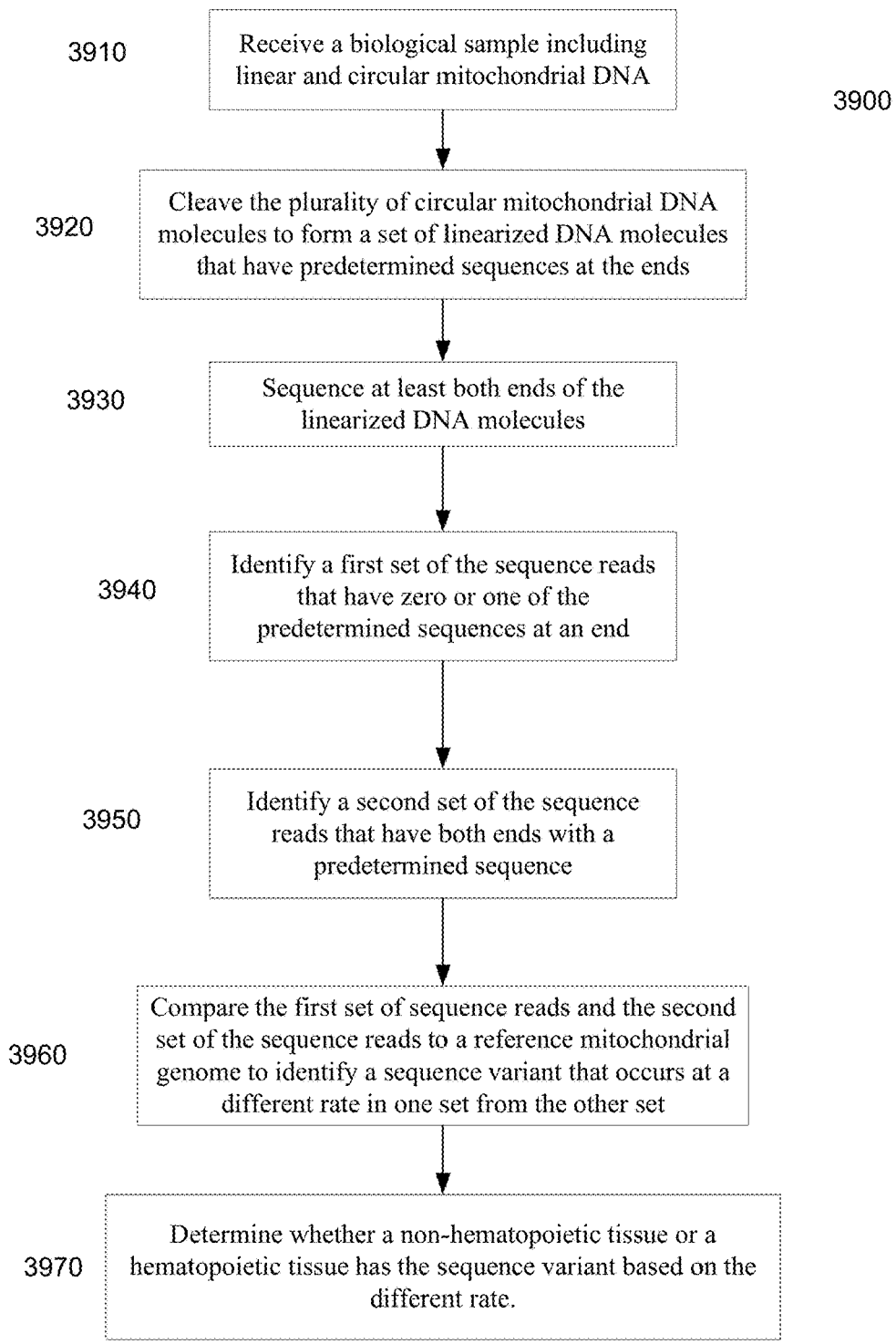
FIG. 39 is a flowchart illustrating a method 3900 for analyzing circular mitochondrial DNA according to embodiments of the present disclosure.

FIG. 39 is a flowchart illustrating a method 3900 for analyzing circular mitochondrial DNA according to embodiments of the present disclosure. Method 3900 can use techniques described in section II.G. Method 3900 can determine a tissue source of sequence variants in mitochondrial DNA.

At block 3910, a biological sample of an organism is received. The biological sample includes cell-free DNA, which includes linear mitochondrial DNA and circular mitochondrial DNA. Block 3910 may be performed in a similar manner as block 3810 of FIG. 38.

At block 3920, a plurality of the circular mitochondrial DNA molecules are cleaved to form a set of linearized mitochondrial DNA molecules that have predetermined sequences at the ends. Block 3920 may be performed in a similar manner as block 3820 of FIG. 38.

At block 3930, at least both ends of the set of the linearized DNA molecules and of a plurality of linear mitochondrial DNA molecules are sequenced to obtain sequence reads. Block 3930 may be performed in a similar manner as block 3830 of FIG. 38.

At block 3940, a first set of the sequence reads that have zero or one of the predetermined sequences at an end is identified. Block 3940 may be performed in a similar manner as block 3840 of FIG. 38.

At block 3950, a second set of the sequence reads that have both ends with a predetermined sequence is identified. Block 3950 may be performed in a similar manner as block 3850 of FIG. 38.

At block 3960, the first set of sequence reads and the second set of the sequence reads are compared to a reference mitochondrial genome to identify a sequence variant that occurs at a different rate in one set from the other set. In some embodiments, the first set of sequence reads can be compared to a reference mitochondrial genome to identify a first set of sequence variants at a first set of loci. The second set of sequence reads can be compared to the reference mitochondrial genome to determine whether the first set of sequence variants occur in the second set of sequence reads. In some embodiments, the reference mitochondrial genome can correspond to the subject, e.g., as determined from healthy cells. Such a reference mitochondrial genome can be referred to as a constitutional mitochondrial genome.

At block 3970, it is determined whether a non-hematopoietic tissue or a hematopoietic tissue has the sequence variant based on the different rate. As an example, the different rate can be a percentage between a first rate (amount) for the first set of sequence reads (likely from a non-hematopoietic tissue) and a second rate (amount) for the second set of sequence reads. Variants in non-hematopoietic tissue can occur in transplanted tissue, e.g., in the live example described above or an egg donor, such that the non-hematopoietic tissue may be fetal.

In some embodiments, it can be determined whether the non-hematopoietic tissue has a sequence variant based on a first amount of the first set of sequence reads (i.e., for linear mtDNA) having the sequence variant and a second amount of the second set of sequence reads (i.e., for circular mtDNA) having the sequence variant, e.g., that the first amount is greater than the second amount. The second amount can be zero, indicating that circular mitochondrial DNA is homozygous in the biological sample. Loci where the circular mitochondrial DNA is homozygous may be a criterion for identifying loci that may have a variant in the linear mitochondrial DNA To determine that the non-hematopoietic tissue has the sequence variant, it can be required that the first amount is greater than a first threshold and that the second amount is less than a second threshold (e.g., one if a homozygosity is required). The first threshold can be the same or different, and can be a percentage sequence reads. In various embodiments, the genomic sites being analyzed are required to be covered at least, but not limited to, 5, 10, 20, 30, 40, 50, 60, 70, 80, 90, 100, 200, 300, 400, 500, 1000, 2000, 3000, 4000, 5000, 10000 sequence reads. The percentage of sequence reads carrying variant alleles in linear mtDNA molecules could be, for example but not limited to, greater than 1%, 2%, 3%, 4%, 5%, 10%, 20%, 30%, 40% and 50%, whereas the percentage of sequence reads carrying variant alleles in circular mtDNA molecules could be, for example but not limited to, less than 1%, 2%, 3%, 4%, 5%, 10%, 20%, 30%, 40% and 50%. The thresholds can be used to determine that a variant is more prevalent in linear mtDNA than in circular mtDNA, e.g., as opposed to just the first amount being higher than the second amount. Variants identified from linear mtDNA would be more likely associated with liver cells (e.g. for detection and/or monitoring of liver cancers, or disorders involving hepatocytes) whereas the variants identified from circular mtDNA would be more likely associated with blood lineage cells.

In some embodiments, an amount of mutations can be compared to a threshold to detect a disease (e.g., cancer). The amount of mutations can be required to be in the linear mtDNA and/or the circular mtDNA. For example, it can be determined that the non-hematopoietic tissue has a disease (e.g., cancer) based on the first amount being greater than a threshold (cutoff). The threshold can be determined based on measurements in a cohort of healthy subjects and/or based on measurements in a cohort of subjects having the disease.

In other embodiments, it can be determined that the hematopoietic tissue has the sequence variant based on the second amount being greater than the first amount. Similar thresholds can be used to require that the second amount be sufficiently greater than the first amount, e.g., so that a desired statistical accuracy is obtained. In some embodiments, it can be determined that the hematopoietic tissue is diseased (e.g., hematopoietic cancer) based on the second amount being greater than a threshold. The threshold can be determined based on measurements in a cohort of healthy subjects and/or based on measurements in a cohort of subjects having the disease.

I. Level of Disease and Treatment

Some embodiments may further include treating the subject for the disease/condition responsive to the classification being that the subject has the condition, thereby improving the condition (e.g., to remove the condition or reduce severity). Treatment can be provided according to a determined level of the disease/disorder, the identified variants, and/or the tissue of origin (e.g., hematopoietic or non-hematopoietic). For example, an identified variant can be targeted with a particular drug or chemotherapy. The tissue of origin can be used to guide a surgery or any other form of treatment. And, the level of disorder can be used to determine how aggressive to be with any type of treatment.

Various treatments can be performed. Treatment may include any suitable therapy, including drug, chemotherapy, radiation, immunotherapy, hormone therapy, stem cell transplant, or surgery, including any treatment described in a reference mentioned herein. Information on treatments in the references are incorporated herein by reference. The treatment may be targeted, e.g., using precision medicine tailored to the specific properties of the disease, e.g., a particular genetic composition of a tumor. Based on the determined level of condition, a treatment plan can be developed to decrease the risk of harm to the subject. Methods may further include treating the subject according to the treatment plan.

Biological samples can be obtained at various time points and analyzed independently at those time points, or in conjunction with the measurements and classifications at the other time points. Examples of such time points include before and after treatment of cancer (e.g. targeted therapy, immunotherapy, chemotherapy, surgery), different time points following the diagnosis of cancer, before and after progression of cancer, before and after development of metastasis, before and after increased severity of disease, or before and after development of complications As mentioned above, machine learning models can be used to determine a level of a disease. Example models could include, but not limited to, linear regression, logistic regression, neural networks such as deep recurrent neural network, Bayes classifier, hidden Markov model (HMM), linear discriminant analysis (LDA), k-means clustering, density-based spatial clustering of applications with noise (DBSCAN), decision tree (e.g., random forest), and support vector machine (SVM).

The model may include a supervised learning model. Supervised learning models may include different approaches and algorithms including analytical learning, artificial neural network, backpropagation, boosting (meta-algorithm), Bayesian statistics, case-based reasoning, decision tree learning, inductive logic programming, Gaussian process regression, genetic programming, group method of data handling, kernel estimators, learning automata, learning classifier systems, minimum message length (decision trees, decision graphs, etc.), multilinear subspace learning, naive Bayes classifier, maximum entropy classifier, conditional random field, Nearest Neighbor Algorithm, probably approximately correct learning (PAC) learning, ripple down rules, a knowledge acquisition methodology, symbolic machine learning algorithms, subsymbolic machine learning algorithms, support vector machines, Minimum Complexity Machines (MCM), random forests, ensembles of classifiers, ordinal classification, data pre-processing, handling imbalanced datasets, statistical relational learning, or Proaftn, a multicriteria classification algorithm.

III. Example Systems

Figure 40:
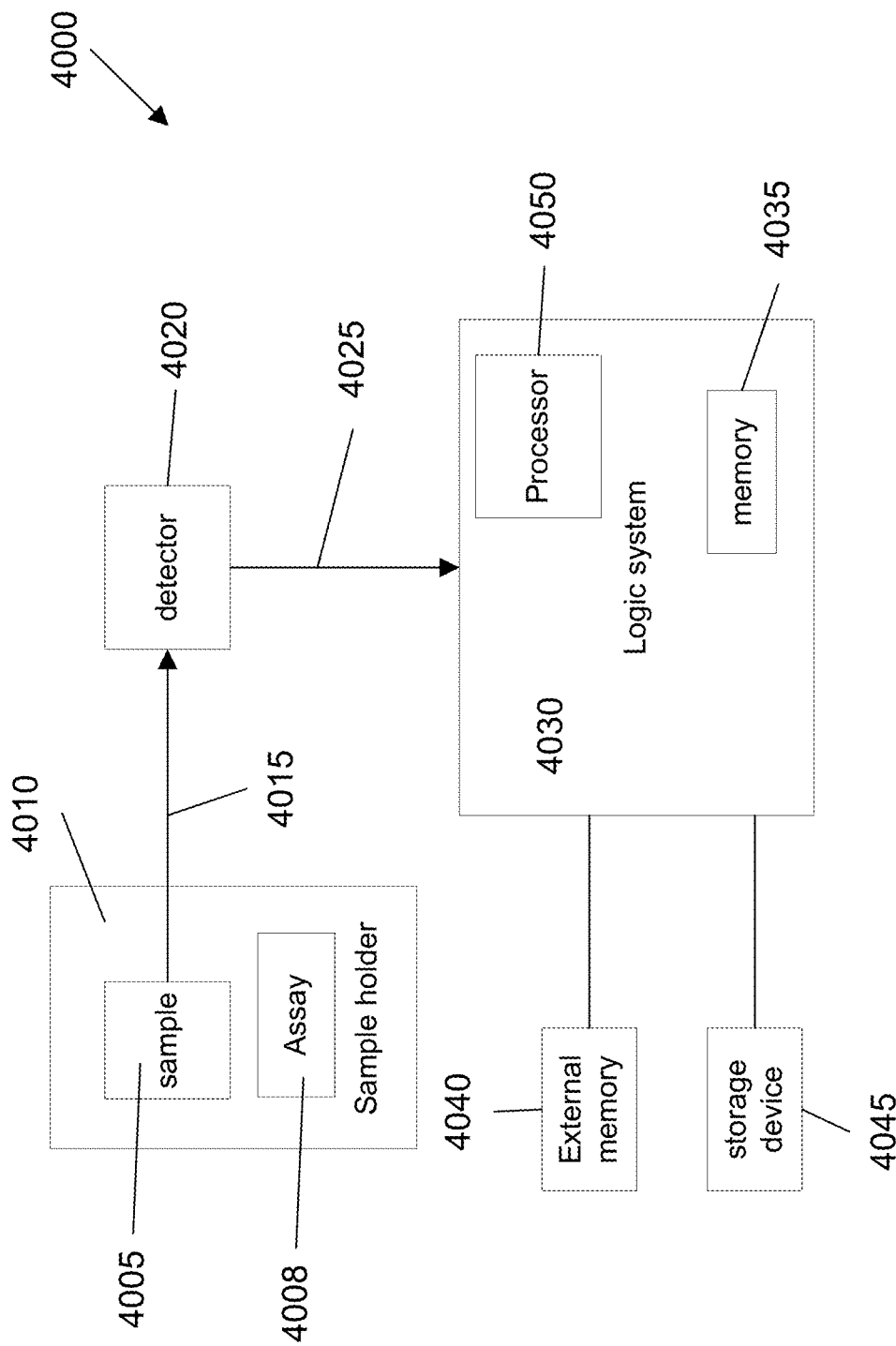
FIG. 40 illustrates a system according to embodiments of the present disclosure.

FIG. 40 illustrates a measurement system 4000 according to an embodiment of the present disclosure. The system as shown includes a sample 4005, such as cell-free DNA molecules within a sample holder 4010, where sample 4005 can be contacted with an assay 4008 to provide a signal of a physical characteristic 4015. An example of a sample holder can be a flow cell that includes probes and/or primers of an assay or a tube through which a droplet moves (with the droplet including the assay). Physical characteristic 4015 (e.g., a fluorescence intensity, a voltage, or a current), from the sample is detected by detector 4020. Detector 4020 can take a measurement at intervals (e.g., periodic intervals) to obtain data points that make up a data signal. In one embodiment, an analog-to-digital converter converts an analog signal from the detector into digital form at a plurality of times. Sample holder 4010 and detector 4020 can form an assay device, e.g., a sequencing device that performs sequencing according to embodiments described herein. A data signal 4025 is sent from detector 4020 to logic system 4030. Data signal 4025 may be stored in a local memory 4035, an external memory 4040, or a storage device 4045.

Logic system 4030 may be, or may include, a computer system, ASIC, microprocessor, etc. It may also include or be coupled with a display (e.g., monitor, LED display, etc.) and a user input device (e.g., mouse, keyboard, buttons, etc.). Logic system 4030 and the other components may be part of a stand-alone or network connected computer system, or they may be directly attached to or incorporated in a device (e.g., a sequencing device) that includes detector 4020 and/or sample holder 4010. Logic system 4030 may also include software that executes in a processor 4050. Logic system 4030 may include a computer readable medium storing instructions for controlling system 4000 to perform any of the methods described herein. For example, logic system 4030 can provide commands to a system that includes sample holder 4010 such that sequencing or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

Any of the computer systems mentioned herein may utilize any suitable number of subsystems. Examples of such subsystems are shown in FIG. 41 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 41 are interconnected via a system bus 75. Additional subsystems such as a printer 74, keyboard 78, storage device(s) 79, monitor 76 (e.g., a display screen, such as an LED), which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk) or Blu-ray disk, flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the disclosure. However, other embodiments of the disclosure may be directed to specific embodiments relating to each individual aspect, or specific combinations of these individual aspects.

The above description of example embodiments of the present disclosure has been presented for the purposes of illustration and description. It is not intended to be exhaustive or to limit the disclosure to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

What is claimed is:

1. A method comprising:
   receiving a biological sample of an organism, the biological sample including a plurality of extrachromosomal circular DNA (eccDNA) molecules, wherein each of the plurality of eccDNA molecules includes a junction at which nucleotides at two separated genomic locations are immediately adjacent to one another;
   cleaving the plurality of eccDNA molecules to form a set of linearized DNA molecules that each includes the junction, the set of linearized DNA molecules comprising at least 1,000 linearized DNA molecules;
   for each of the set of linearized DNA molecules:
   sequencing at least both ends of the linearized DNA molecule to obtain one or more sequence reads;
   selecting a pair of end sequences for the linearized DNA molecule from the one or more sequence reads, the pair of end sequences not including the junction;
   reversing a direction of each of the pair of end sequences to obtain a pair of reversed end sequences; and
   mapping the pair of reversed end sequences to a reference genome; and
   analyzing the mapped reversed end sequences to measure a property of the biological sample.

2. The method of claim 1, further comprising:
   detecting the plurality of eccDNA molecules based on the pair of reversed end sequences mapping to the reference genome; and
   determining a collective value of the detected eccDNA molecules, wherein analyzing the mapped reversed end sequences to measure the property of the biological sample uses the collective value.

3. The method of claim 2, wherein the collective value includes a count, a size, or a methylation level determined using the detected eccDNA molecules.

4. The method of claim 1, wherein, for each of the linearized DNA molecules, the one or more sequence reads include the junction.

5. The method of claim 4, wherein analyzing a mapped reversed end sequence includes:
   comparing bases in the one or more sequence reads extending past each of the mapped reversed end sequences to the reference genome until a mismatch condition is identified; and
   identifying end positions of a linearized DNA molecule from which the eccDNA molecule was formed based on a location of the mismatch condition in the reference genome.

6. The method of claim 5, wherein analyzing the mapped reversed end sequence further includes:
   determining a size of the linearized DNA molecule using the end positions.

7. The method of claim 6, wherein analyzing the mapped reversed end sequences further includes:
   determining a size distribution of the sizes measured for the plurality of eccDNA molecules; and
   using the size distribution to measure the property of the biological sample.

8. The method of claim 1, wherein analyzing the mapped reversed end sequences includes:
   counting a number of the plurality of eccDNA molecules that map to a chromosomal region, where the property of the biological sample is of the chromosomal region; and
   using the number to measure the property of the chromosomal region.

9. The method of claim 8, wherein the property is a copy number aberration in the chromosomal region, the method further comprising:
   measuring a methylation density in the chromosomal region using DNA molecules in the biological sample; and
   using the copy number aberration and the methylation density to detect a condition with the organism.

10. The method of claim 9, wherein the methylation density is determined to exhibit hypermethylation by comparing to a cutoff, and wherein the condition is fragile X syndrome or a triplet repeat expansion.

11. The method of claim 8, wherein the property of the chromosomal region is that the chromosomal region carries information regarding the property of the biological sample or has an aberration including a sequence alteration, duplication, expansion, deletion or an amplification in the biological sample.

12. The method of claim 11, wherein the biological sample is obtained from a subject being screened for cancer, further comprising:
identifying a level of cancer in the organism based on the chromosomal region having the aberration.

13. The method of claim 11, wherein the biological sample is obtained from a female pregnant with a fetus, and wherein the aberration is in the fetus.

14. The method of claim 11, wherein the property is sex or genotypic information.

15. The method of claim 1, wherein the biological sample includes a first tissue type and a second tissue type, wherein the first tissue type is homozygous for a first allele at a locus, and wherein the second tissue type is heterozygous for the first allele and a second allele at the locus, the method further comprising:
determining a first number of the mapped reversed end sequences that have the first allele at the locus;
determining a second number of the mapped reversed end sequences that have the second allele at the locus; and
determining a fractional concentration of eccDNA molecules from the second tissue type using the first number and the second number.

16. The method of claim 1, further comprising:
determining a number of sequence variants in the mapped reversed end sequences; and
determining a level of cancer using the number of sequence variants.

17. The method of claim 1, further comprising:
prior to cleaving the plurality of eccDNA molecules, reducing linear DNA in the biological sample by exonuclease digestion.

18. The method of claim 1, wherein the plurality of eccDNA molecules are cell-free.

19. The method of claim 1, wherein cleaving the plurality of eccDNA molecules includes:
digesting, with a restriction enzyme, the plurality of eccDNA molecules to form the set of linearized DNA molecules.

20. The method of claim 19, wherein the restriction enzyme cuts a particular sequence, the method further comprising:
identifying the particular sequence spanning the pair of end sequences of at least a portion of the linearized DNA molecules.

21. The method of claim 19, wherein the restriction enzyme cuts at least a 4-bp sequence.

22. The method of claim 1, wherein cleaving the plurality of eccDNA molecules includes:
cleaving, using a transposase, the plurality of eccDNA molecules; and
attaching, using the transposase, adapter sequences to both cleaved ends of each of the plurality of eccDNA molecules, thereby forming the set of linearized DNA molecules.

23. A method comprising:
receiving a biological sample of an organism, the biological sample including a plurality of extrachromosomal circular DNA (eccDNA) molecules, wherein each of the plurality of eccDNA molecules includes a junction at which nucleotides at two separated genomic locations are immediately adjacent to one another;
digesting, with a restriction enzyme, the plurality of eccDNA molecules to form a set of linearized DNA molecules that each includes the junction, the set of linearized DNA molecules comprising at least 1,000 linearized DNA molecules; and
for each of the set of linearized DNA molecules:
sequencing at least both ends of the set of linearized DNA molecules to obtain one or more sequence reads;
selecting a pair of end sequences for the linearized DNA molecule from the one or more sequence reads, the pair of end sequences not including the junction; and
reversing a direction of each of the pair of end sequences to obtain a pair of reversed end sequences.

24. A method comprising:
receiving a biological sample of an organism, the biological sample including a plurality of extrachromosomal circular DNA (eccDNA) molecules, wherein each of the plurality of eccDNA molecules includes a junction at which nucleotides at two separated genomic locations are immediately adjacent to one another;
cleaving, using a transposase, the plurality of eccDNA molecules;
attaching, using the transposase, adapter sequences to both cleaved ends of each of the plurality of eccDNA molecules, thereby forming a set of linearized DNA molecules that each includes the junction and the adapter sequences, the set of linearized DNA molecules comprising at least 1,000 linearized DNA molecules; and
for each of the set of linearized DNA molecules:
sequencing at least both ends of the set of linearized DNA molecules to obtain one or more sequence reads;
selecting a pair of end sequences for the linearized DNA molecule from the one or more sequence reads, the pair of end sequences not including the junction; and
reversing a direction of each of the pair of end sequences to obtain a pair of reversed end sequences.

25. The method of claim 24, wherein the transposase comprises a Tn5 transposase.

* * * * *